United States Patent
Capobianco et al.

(10) Patent No.: US 10,501,413 B2
(45) Date of Patent: Dec. 10, 2019

(54) INHIBITORS OF THE NOTCH TRANSCRIPTIONAL ACTIVATION COMPLEX AND METHODS FOR USE OF THE SAME

(71) Applicants: UNIVERSITY OF MIAMI, Miami, FL (US); UNIVERSITY OF MARYLAND, BALTIMORE, Baltimore, MD (US)

(72) Inventors: Anthony J. Capobianco, Miami, FL (US); Alex Mackerell, Jr., Baltimore, MD (US); Mark Spyvee, Hampstead, NH (US)

(73) Assignees: UNIVERSITY OF MIAMI, Miami, FL (US); UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 15/560,743

(22) PCT Filed: Mar. 23, 2016

(86) PCT No.: PCT/US2016/023691
§ 371 (c)(1),
(2) Date: Sep. 22, 2017

(87) PCT Pub. No.: WO2016/154255
PCT Pub. Date: Sep. 29, 2016

(65) Prior Publication Data
US 2018/0086700 A1    Mar. 29, 2018

Related U.S. Application Data

(60) Provisional application No. 62/136,895, filed on Mar. 23, 2015.

(51) Int. Cl.
| | | |
|---|---|---|
| C07D 207/444 | (2006.01) | |
| A61K 31/4015 | (2006.01) | |
| A61K 31/426 | (2006.01) | |
| C07D 277/54 | (2006.01) | |
| C07D 277/36 | (2006.01) | |

(52) U.S. Cl.
CPC ...... *C07D 207/444* (2013.01); *A61K 31/4015* (2013.01); *A61K 31/426* (2013.01); *C07D 277/36* (2013.01); *C07D 277/54* (2013.01)

(58) Field of Classification Search
CPC .................................................. C07D 207/444
USPC ........................................................ 514/369
See application file for complete search history.

(56) References Cited

U.S. PATENT DOCUMENTS 7,879,893 B2    2/2011 Olsen et al.
2014/0329867 A1    11/2014 Radtke et al.

FOREIGN PATENT DOCUMENTS

| WO | WO-200949423 A1 | 4/2009 |
| WO | WO-2009/064486 A9 | 7/2009 |
| WO | WO-2014/062811 A2 | 4/2014 |

OTHER PUBLICATIONS

King, Med. Chem., Principle and Practice (1994), pp. 206-208.*
International Preliminary Report on Patentability, for International Application No. PCT/US2016/023691, dated Sep. 26, 2017.
International Search Report and Written Opinion of the International Searching Authority, for International Application No. PCT/US2016/023691, dated Jun. 21, 2016.
Moellering et al. "Direct inhibition of the NOTCH transcription factor complex" Nature, Nov. 12, 2009 (Nov. 12, 2009), vol. 462, p. 182-188; p. 186, para 1-4.
Astudillo et al. "The small molecule IMR-1 inhibits the Notch transcriptional activation complex to suppress tumorigenesis" Cancer Research, Apr. 13, 2016 (Apr. 13, 2016); entire document.
Beharry et al., "Novel benzylidene-thiazolidine-2, 4-diones inhibit Pim protein kinase activity and induce cell cycle arrest in leukemia and prostate cancer cells," Mol. Cancer Ther., 8:1473-1483 (2009).
Espinoza et al., "Notch inhibitors for cancer treatment", Pharmacology & Therapeutics, 139:95-110 (2013).
Extended European Search Report, which includes the supplementary European search report and the European search opinion, for European Patent Application No. 16769567.5, dated Aug. 24, 2018.
Russell et al., "Selective small molecule inhibitors of the potential breast cancer marker, human arylamine N-acetyltransferase 1, and its murine homologue, mouse arylamine N-acetyltransferase 2", Bioorganic & Medicinal Chemistry, 17:905-918 (2009).
Wu et al., "Anticancer Activity of 5-Benzylidene-2-Phenylimino-1, 3-Thiazolidin-4-one (BPT) Analogs", Medicinal Chemistry, vol. 2, No. 6, pp. 597-605 (2006).
Yap et al., "Small-Molecule Inhibitors of the ERK Signaling Pathway: Towards Novel Anticancer Therapeutics", ChemMedChem, 6:38 (2011).

* cited by examiner

*Primary Examiner* — Taofiq A Solola
(74) *Attorney, Agent, or Firm* — Marshall, Gerstein & Borun LLP

(57) ABSTRACT

Disclosed herein are inhibitors of the Notch transcriptional activation complex, and methods for their use in treating or preventing diseases, such as cancer. The inhibitors described herein can include compounds of Formula (I) and pharmaceutically acceptable salts thereof: Formula (I), wherein the substituents are as described.

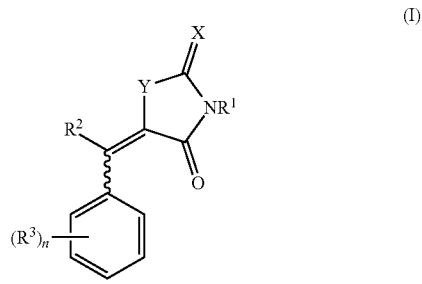

16 Claims, 13 Drawing Sheets

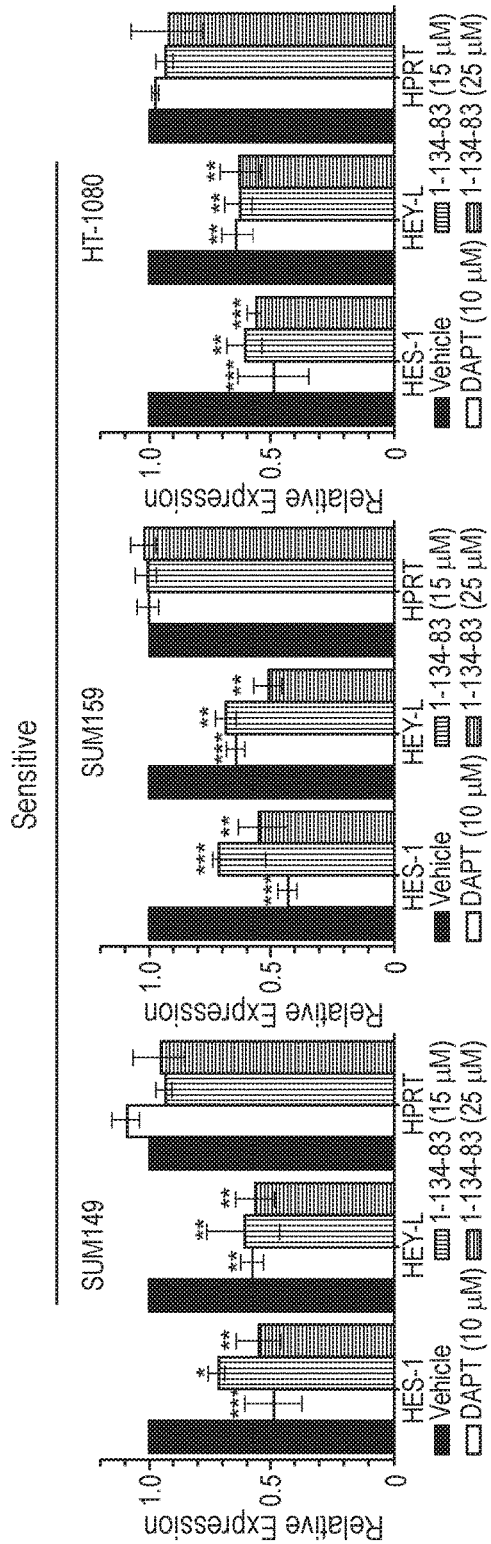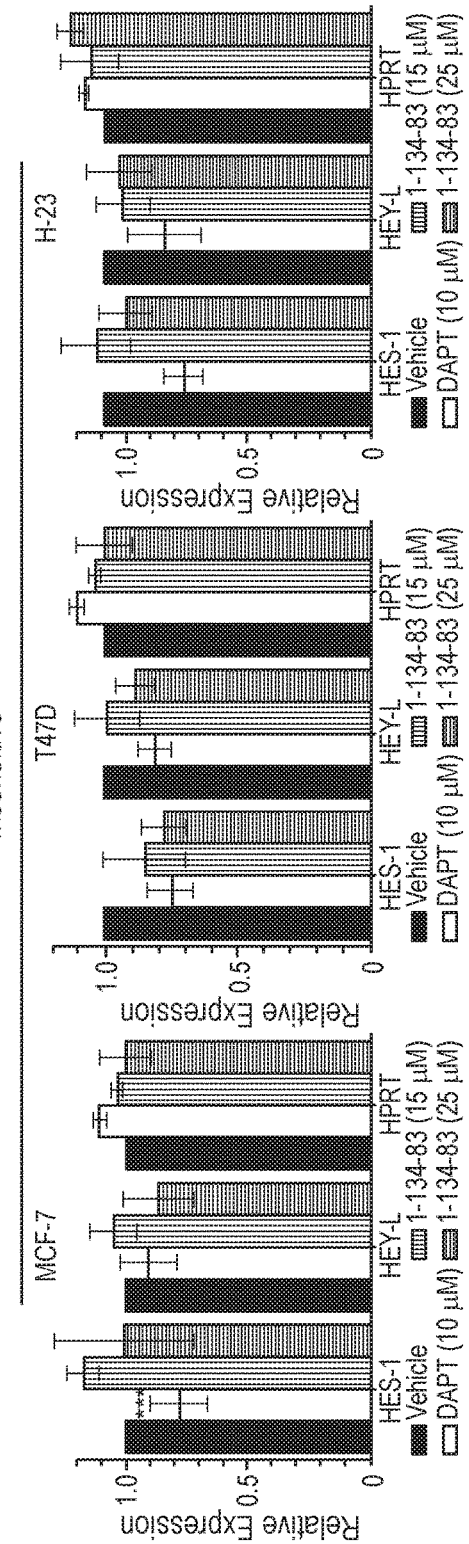
FIG. 3A
FIG. 3B

INHIBITORS OF THE NOTCH TRANSCRIPTIONAL ACTIVATION COMPLEX AND METHODS FOR USE OF THE SAME

CROSS-REFERENCE TO RELATED APPLICATION

This application is filed pursuant to 35 U.S.C. § 371 as a U.S. National Phase Application of International Application No. PCT/US2016/023691 (filed on Mar. 23, 2016), claiming the benefit under 35 U.S.C. § 119(e) of U.S. Provisional Patent Application Ser. No. 62/136,895 filed Mar. 23, 2015, the disclosures of which are each hereby incorporated herein by reference.

STATEMENT OF GOVERNMENT SUPPORT

This invention was made with government support under grant numbers NCI R01CA083736-12A1 and NCI R01CA125044-02, each awarded by the National Institutes of Health. The Government has certain rights in the invention.

BACKGROUND OF THE INVENTION

Field of the Invention

The present disclosure relates to inhibitors of the Notch transcriptional activation complex, and methods of using the inhibitors to decrease Notch target gene transcription and to treat and prevent diseases, such as cancer.

Description of Related Technology

The Notch pathway, a highly conserved cell signaling system present in most multicellular organisms, is widely used in development to govern cell fate specification, and to balance proliferative capacity and differentiation state. Notch drives a context-dependent cellular response by initiating and maintaining a transcriptional cascade. Notch mediates this transcriptional response by directing the formation of a core Notch transcriptional activation complex ("NTC"), which is composed of the DNA binding protein CSL, the intracellular domain of Notch ("NICD") and the co-activator protein Mastermind ("MAML1").

In the adult, the Notch pathway is restricted to small populations of progenitor and stem cells of regenerating tissues, such as the colon and brain. However, in many human cancers, the Notch pathway becomes reactivated. The deregulation of the Notch pathway underlies many aspects of cancer physiology, depending on cell type and context. Aberrant Notch activity has been demonstrated to play a role in the initiation and maintenance of the neoplastic phenotype, as well as playing a central role in cancer stem cells, which may underlie a role in metastasis and resistance to therapy.

Current compounds that regulate the Notch pathway include small molecule inhibitors that target the presenilin-dependent γ-secretase, an enzyme complex that is responsible for ligand-induced cleavage and activation of Notch, and monoclonal antibodies that inhibit ligand-receptor interactions. However, there are currently no small molecule inhibitors that directly target the intracellular Notch pathway or the assembly of the transcriptional activation complex.

Thus, there is a need for antineoplastic therapeutics capable of directly targeting the Notch transcriptional activation complex for the treatment and prevention of diseases, such as cancer.

SUMMARY OF THE INVENTION

One aspect of the invention provides a method of inhibiting the Notch transcriptional activation complex ("NTC") in a cell, comprising contacting the cell with a compound of Formula (I), or a pharmaceutically acceptable salt thereof, in an amount effective to inhibit the NTC:

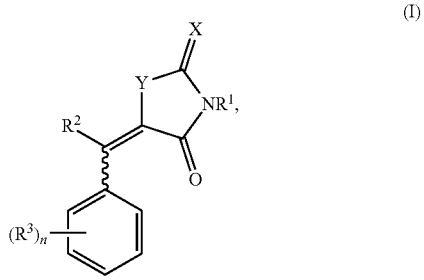

wherein

⁓ represents a bond that results in the adjacent double bond being in either the E or Z configuration;

n is 0, 1, 2, 3, or 4;

X is O or S;

Y is O, S, NH, or $NC_{1-3}$ alkyl;

$R^1$ is selected from the group consisting of H, $C_{1-6}$ alkyl, $C_{1-6}$ alkenyl, $C_{0-6}$ alkylene-$COR^9$, NH-aryl, NH—(C=O)-aryl, $C_{0-6}$alkylene-cycloalkyl, $C_{0-6}$alkylene-heterocycloalkyl, $C_{0-6}$ alkylene-heterocycloalkenyl, $C_{0-6}$ alkylene-aryl, $C_{1-6}$ alkylene-$SO_2R^5$, $C_{1-6}$ alkylene-$R^5$, and $C_{0-6}$ alkylene-heteroaryl;

$R^2$ is H or $C_{1-3}$ alkyl;

each $R^3$ is independently selected from the group consisting of $OR^4$, $COOR^4$, $NO_2$, halo, $SO_2R^5$, $C_{1-6}$ alkyl, $C_{1-6}$ alkenyl, $C_{0-6}$ alkylene-cycloalkyl, $C_{0-6}$ alkylene-aryl, $C_{0-6}$ alkylene-heteroaryl, and (C=O)N($R^7$)$_2$;

$R^4$ is selected from the group consisting of H, $C_{1-6}$ alkyl, $C_{1-6}$ alkenyl, $C_{1-6}$ alkynyl, $C_{0-6}$ alkylene-(C=O)$R^8$, $C_{1-6}$ alkylene-N($R^6$)$_2$, $C_{1-6}$ alkylene-CN, $C_{0-6}$ alkylene-aryl, $C_{0-6}$ alkylene-heteroaryl, $C_{1-6}$ alkylene-O-aryl, $C_{1-6}$ alkylene-S-aryl, $C_{1-6}$ alkylene-$NR^6$-aryl, and $C_{1-6}$ alkylene-$NR^6$-heteroaryl;

$R^5$ is OH, N($R^6$)$_2$, NH(C=O)$C_{1-3}$ alkyl, or NH(C=O)aryl;

each $R^6$ is independently H, $C_{1-3}$ alkyl;

each $R^7$ is independently H, $C_{1-3}$ alkyl, $SO_2H$; or $SO_2(C_{1-3}$ alkyl);

$R^8$ is $C_{1-6}$ alkyl, aryl, $OC_{1-6}$ alkyl, or N($R^6$)$_2$;

$R^9$ is OH, N($R^6$)$_2$, $NHSO_2R^6$, $SO_2N(R^6)_2$, and when n is 2 or 3, two adjacent $R^3$ groups, together with the carbon atoms to which they are attached, can form a fused heterocycloalkyl group, a fused aryl group, or a fused heteroaryl group.

In some cases, $R^2$ is H. In some embodiments, $R^2$ is $C_{1-3}$ alkyl. In various embodiments, X is O. In some cases, X is S. In some embodiments, Y is NH or $NC_{1-3}$ alkyl. In various cases, Y is O. In some cases, Y is S.

In some embodiments, the compound of Formula (I) comprises Formula (Ia), or a pharmaceutically acceptable salt thereof:

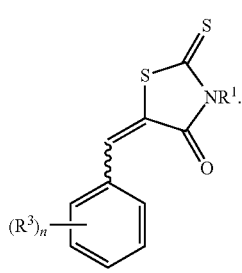

(Ia)

In some embodiments, $R^1$ is $C_{1-6}$ alkyl, $C_{1-6}$ alkenyl, $C_{0-6}$ alkylene-$COR^9$, $C_{0-6}$ alkylene-cycloalkyl, $C_{0-6}$ alkylene-heterocycloalkenyl, $C_{1-6}$ alkylene-$SO_2R^5$, or $C_{1-6}$ alkylene-$R^5$. In various embodiments, $R^1$ is NH-aryl, NH—(C=O)-aryl, $C_{0-6}$ alkylene-heterocycloalkyl, $C_{0-6}$ alkylene-aryl, or $C_{0-6}$ alkylene-heteroaryl. In some cases, $R^1$ is H. In some cases, n is 0. In various cases, n is 1. In some embodiments, n is 2. In various embodiments, n is 3. In some embodiments, at least one $R^3$ is $OR^4$. In some of these cases, $R^4$ is H, $C_{1-6}$ alkyl, $C_{1-6}$ alkenyl, or $C_{1-6}$ alkynyl. In some of these cases, $R^4$ is $C_{1-6}$ alkylene-(C=O)$R^8$, and $R^8$ is $C_{1-6}$ alkyl, or aryl. In some embodiments, $R^4$ is $C_{1-6}$ alkylene-(C=O)$R^8$ and $R^8$ is $OC_{1-6}$ alkyl or $N(R^6)_2$. In some cases, $R^4$ is $C_{1-6}$ alkylene-$N(R^6)_2$, $C_{1-6}$ alkylene-CN, $C_{0-6}$ alkylene-cycloalkyl, $C_{0-6}$ alkylene-aryl, $C_{0-6}$ alkylene-heteroaryl, $C_{1-6}$ alkylene-O-aryl, $C_{1-6}$ alkylene-S-aryl, $C_{1-6}$ alkylene-$NR^6$-aryl, and $C_{1-6}$ alkylene-$NR^6$-heteroaryl. In some embodiments, at least one $R^3$ is selected from the group consisting of halo, $C_{1-6}$ alkyl, $C_{1-6}$ alkenyl, $C_{0-6}$ alkylene-aryl, and $C_{0-6}$ alkylene-heteroaryl. In various embodiments, at least one $R^3$ is selected from the group consisting of COOH, $NO_2$, $SO_2R^5$, and (C=O)$N(R^7)_2$. In various cases, n is 2 or 3, and each $R^3$ is $OR^4$ or halo. In some embodiments, one $R^3$ is OH, and one $R^3$ is $OC_{1-6}$ alkyl or halo. In some of these cases, n is 2, and the other $R^3$ is $OC_{1-6}$ alkyl.

In some embodiments, the compound of Formula (I) or Formula (a) comprises a compound of Formula (Ib), or a pharmaceutically acceptable salt thereof:

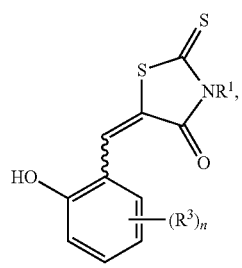

(Ib)

wherein n is 1 or 2.

In some embodiments, n is 1, $R^3$ is $OC_{1-6}$ alkyl, and $R^3$ is para to the hydroxyl substituent. In some cases, two adjacent $R^3$ groups, together with the carbon atoms to which they are attached form a fused heterocycloalkyl group, a fused aryl group, or a fused heteroaryl group. The various cases, the fused group is a dioxole, a dihydrofuran, or a phenyl.

In any of the embodiments disclosed herein, the ⌇ can represent a bond that results in the adjacent double bond being in the Z configuration.

Another aspect of the disclosure relates to a method of inhibiting the Notch transcriptional activation complex in a cell, comprising contacting the cell with a compound, or a pharmaceutically acceptable salt thereof selected from a compound listed in Table 1, a compound listed in Table 2, or a mixture thereof, in an amount effective to inhibit the NTC. In some cases, the compound inhibits MAML1 recruitment to the Notch transcriptional activation complex. In various cases, the contacting occurs in vivo. In some embodiments, the contacting comprises administering to a patient in need thereof. In various embodiments, the patient suffers from a disease associated with deregulation of the Notch transcriptional activation complex.

Yet another aspect of the disclosure relates to a method of treating a disease associated with deregulation of the Notch transcriptional activation complex in a patient, comprising administering to the patient a therapeutically effective amount of a compound, or a pharmaceutically acceptable salt thereof, selected from the group consisting of (i) a compound of Formula (I), as previously described herein; (ii) a compound of Formula (Ia), as previously described herein; (iii) a compound of Formula (Ib), as previously described herein; (iv) a compound listed in Table 1; (v) a compound listed in Table 2; and (vi) or a combination thereof. In any of these embodiments, the ⌇ in Formula (I), (Ia), and (Ib) can represents a bond that results in the adjacent double bond being in the Z configuration. In some of these embodiments, the compounds listed in Table 1 and Table 2 are in the Z configuration.

In some embodiments, the disease is Tetralogy of Fallot ("TOF") or Alagille syndrome. In various embodiments, the disease is cancer. For example, the cancer can be selected from the group consisting of T-cell acute lymphoblastic leukemia ("T-ALL"), B-cell acute lymphoblastic leukemia ("B-ALL"), breast cancer, medulloblastoma, colorectal cancer, non-small cell lung carcinoma ("NSCLC"), melanoma, cerebral autosomal-dominant ateriopathy with sub-cortical infarcts and leukoencephalophathy ("CADASIL"), chronic lymphocytic leukemia ("CLL"), hepatocellular carcinoma ("HCC"), myelomonocytic leukemia ("CMML"), pancreatic ductal adenocarcinoma ("PDAC"), multiple sclerosis ("MS"), head and neck squamous cell carcinoma ("HNSCC"), renal cell adenocarcinoma, and fibrosarcoma.

Another aspect of the disclosure provides a compound selected from the group consisting of:

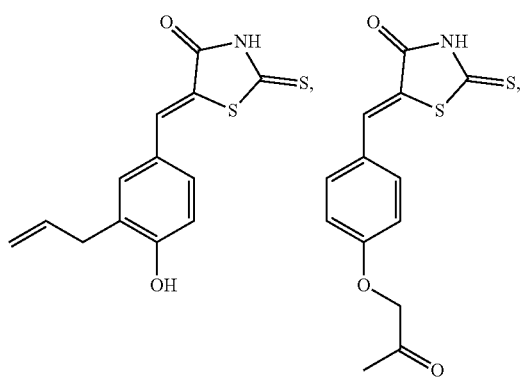

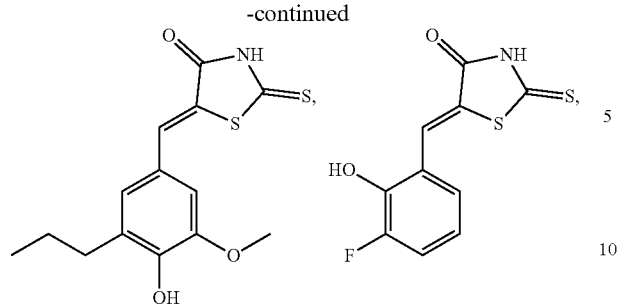
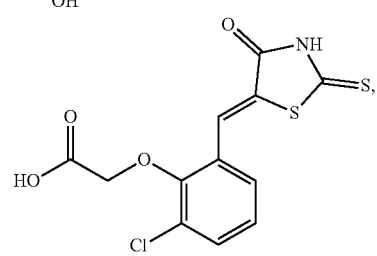
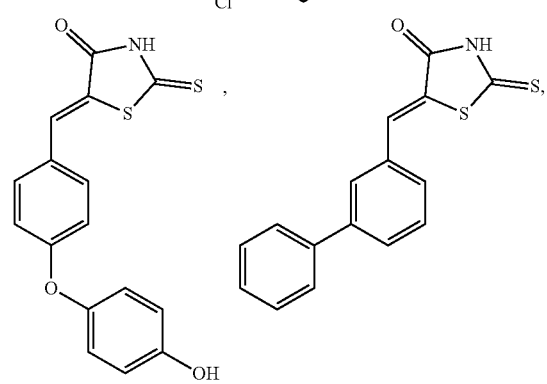
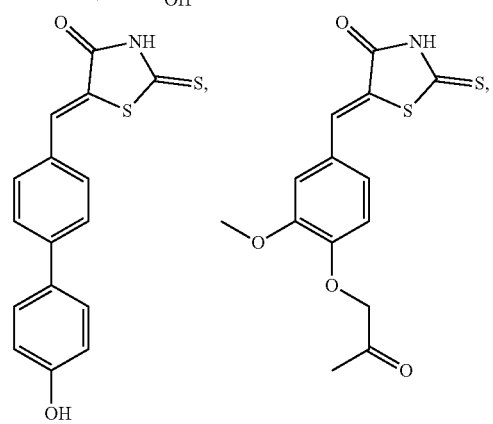
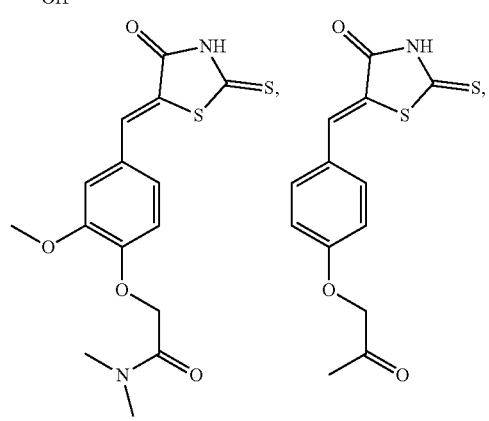
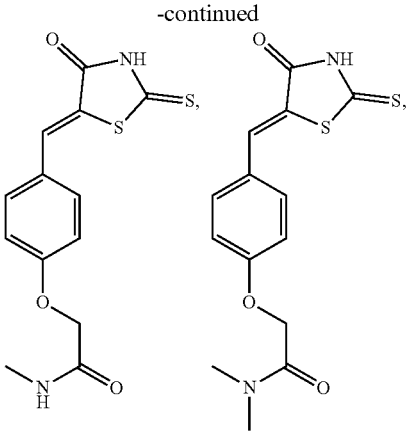
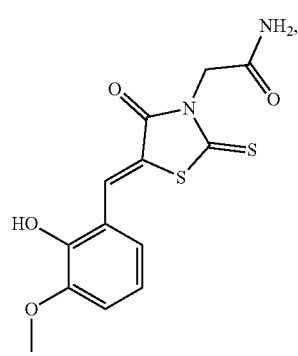
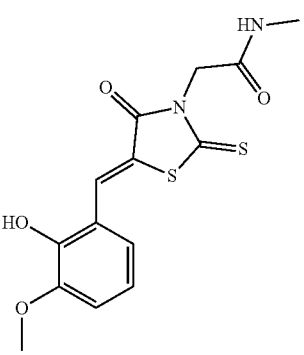
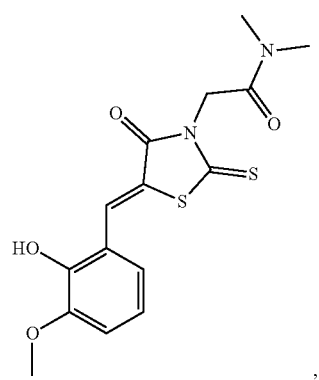
, and -continued

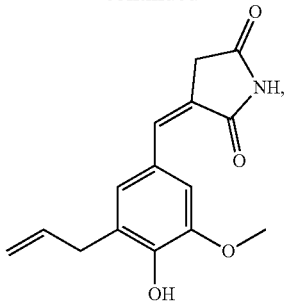

or a pharmaceutically acceptable salt thereof.

Further aspects and advantages will be apparent to those of ordinary skill in the art from a review of the following detailed description, taken in conjunction with the drawings. While the compounds and methods disclosed herein are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

FIG. 1 depicts the Notch transcriptional activation complex assembly assay.

FIG. 2 illustrates that Inhibitor No. 1-134-83 inhibits Notch target gene transcription by displacing MAML1 from chromatin. OE33 and 786-0 cells were treated with vehicle, DAPT (10 μM) and Inhibitor No. 1-134-83 (15 μM). Treated cells were used for ChIP assays using either MAML1 or Notch1 antibodies, immunoblotting or qPCR.

FIG. 3 depicts treatment of cancer cell lines with DAPT or Inhibitor No. 1-134-83. A panel of cancer cell lines was treated with vehicle (Black), DAPT (10 γM; green bars), or Inhibitor No. 1-134-83 (15 and 25 μM, orange bars) for 48 hrs. FIGS. 3A and 3B depict the qPCR analysis of Notch target genes, and shows that transcription is significantly reduced in both DAPT and Inhibitor No. 1-134-83 treatment. Insensitive cells do not show a statistically significant reduction in Notch target gene transcription when treated with DAPT or Inhibitor No. 1-134-83.

Figure 1A:
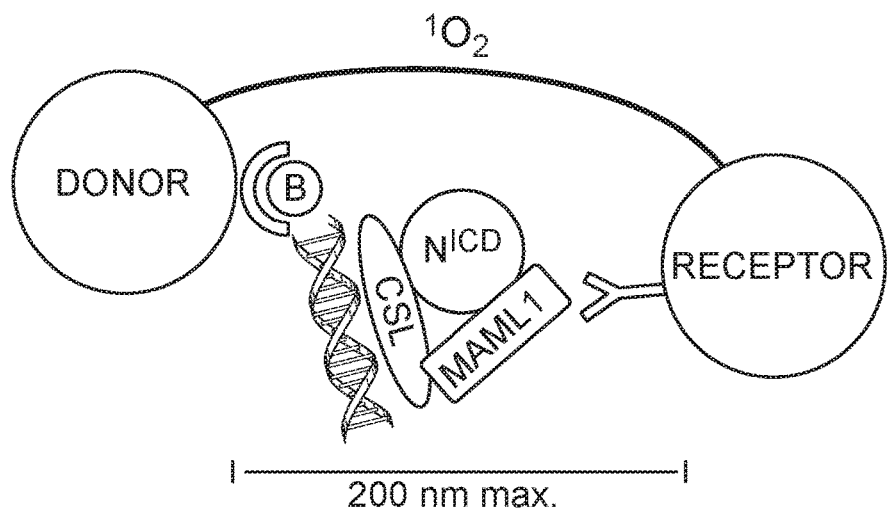
FIG. 1A shows a schematic of the alpha-based Notch transcriptional activation complex assembly assay.

and Vehicle (DMSO). Positive control is hNotch1 (human Notch1 intracellular domain) mRNA (100 pg) injected embryos. Scale bar is 0.1 mm. Graph. Percentage of embryos with somites. * indicates a p<0.0001 by Fisher's exact test between both untreated and drug treated embryos and DMSO and drug treated embryos.

DETAILED DESCRIPTION OF THE INVENTION

Provided herein are compounds that inhibit the Notch transcriptional activation complex ("NTC"), and methods of using the inhibitors to decrease Notch target gene transcription, and to treat and prevent diseases associated with the NTC, such as cancer.

Assembly of the Notch transcriptional activation complex is thought to occur in a stepwise fashion. Without being bound by any particular theory, the RAM domain of Notch and the β-trefoil domain ("BTD") of CSL form a high affinity interface. The Ankyrin repeat domain ("ANK") of Notch makes contacts with the C-terminal domain ("CTD") of CSL. Together, Notch and CSL create a cleft, which is required for stable MAML1 association to the complex. MAML1 interacts with the ANK domain of Notch, and also with both the N-terminal domain ("NTD") and CTD domains of CSL through an α-helical domain in its N-terminus. Once bound, MAML1 locks the core scaffold together and serves to recruit the higher order transcription regulatory machinery, thereby initiating the expression of Notch target genes.

Also without being bound by any particular theory, the inhibitors disclosed herein disrupt the recruitment of MAML1 to the Notch transcriptional activation complex on chromatin, thereby uncoupling the Notch mediated transcriptional cascade in response to activation, and decreasing Notch target gene transcription. As a result, the growth of Notch-dependent cells is inhibited, which stunts tumor growth in a subject. In some cases, the inhibitors disclosed herein are specific for Notch dependent cells, and therefore, do not inhibit or kill cells that are not dependent on Notch.

Notch is a particularly attractive target for inhibitor development. Prior to ligand activation and cleavage, the intracellular domain of Notch ("NICD") is bound to the cell membrane, and therefore, accessible to potential inhibitors. Further, the NTC is constantly being recycled, thus requiring constant reformation on chromatin for maintenance of the Notch transcriptional cascade driving the neoplastic phenotype. Therefore, ample opportunity exists for a small molecule to target the exposed interaction surfaces on the NTC components and prevent complex formation.

The inhibitors of the disclosure can inhibit formation of the NTC by more than about 50%, 55%, 60%, 65%, 70%, 75%, 80%, 85%, 90%, 95%, 97%, or 99% of the positive control. In some embodiments, the inhibitors of the disclosure can inhibit formation of the NTC by more than about 75%, 80%, 85%, 90%, 95%, 97%, or 99% of the positive control. For example, the inhibitors disclosed herein can inhibit formation of the NTC by more than about 85%, 86%, 87%, 88%, 89%, 90%, 91%, 92%, 93%, 94%, 95%, 96%, 97%, 98%, or 99% of the positive control. Furthermore, the inhibitors disclosed herein can disrupt the assembly of the NTC with an $IC_{50}$ of less than about 5 µM, or less than about 4 µM, or less than about 3 µM, or less than about 2 µM, or less than about 1 µM, or less than about 0.6 µM, or less than about 0.5 µM, or less than about 0.4 µM, or less than about 0.3 µM, or less than about 0.2 µM, or less than about 0.1 µM, or less than about 0.05 µM. In some embodiments, the inhibitors of the disclosure can disrupt the assembly of the NTC with an $IC_{50}$ of less than about 1 µM, or less than about 0.6 µM, or less than about 0.5 µM, or less than about 0.4 µM, or less than about 0.3 µM, or less than about 0.2 µM, or less than about 0.1 µM, or less than about 0.05 µM. In some cases, the inhibitors of the disclosure can disrupt the assembly of the NTC with an $IC_{50}$ of less than about 0.5 µM, or less than about 0.4 µM, or less than about 0.3 µM, or less than about 0.2 µM, or less than about 0.1 µM, or less than about 0.05 µM. For example, the inhibitors of the disclosure can disrupt the assembly of the NTC with an $IC_{50}$ of less than about 0.2 µM, or less than about 0.19 µM, or less than about 0.18 µM, or less than about 0.17 µM, or less than about 0.16 µM, or less than about 0.15 µM, or less than about 0.14 µM, or less than about 0.13 µM, or less than about 0.12 µM or less than about 0.11 µM, or less than about 0.10 µM, 0.09 µM, or less than about 0.08 µM, or less than about 0.07 µM, or less than about 0.06 µM or less than about 0.05 µM.

The inhibitors of the disclosure have several advantageous properties and effects. They can: disrupt the assembly of the NTC with $IC_{50}$s in the low micromolar range. They exhibit specifically by inhibiting the binding of MAML1 to the DNA bound complex, without affecting either CSL or Notch binding. They can selectively kill cells in culture that are dependent on Notch signaling for viability, and they exhibit specific inhibition of Notch-dependent activity in vivo. Further, they inhibit recruitment of MAML1 to Notch, without affecting Notch bound to chromatin. As described herein, the inhibitors can stunt the growth of tumors in mice, yet have no observable adverse effects, such as loss of body weight or in the general appearance. Finally, the inhibitors have been shown to inhibit Notch-dependent somite formation in zebrafish without non-specific effects on embryogenesis.

Definitions

As used herein, "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

The term "alkenyl" is defined identically as "alkyl" except for containing at least one carbon-carbon double bond, and having two to thirty carbon atoms, for example, two to twenty carbon atoms, or two to ten carbon atoms. The term $C_n$ refers to an alkenyl group having "n" carbon atoms. For example, $C_4$ alkenyl refers to an alkenyl group that has 4 carbon atoms. $C_2$-$C_7$ alkenyl refers to an alkenyl group having a number of carbon atoms encompassing the entire range (i.e., 2 to 7 carbon atoms), as well as all subgroups (e.g., 2-6, 2-5, 3-6, 2, 3, 4, 5, 6, and 7 carbon atoms). Unless otherwise indicated, an alkenyl group can be an unsubstituted alkenyl group or a substituted alkenyl group.

As used herein, the term "alkylene" refers to an alkyl group having a substituent. For example, the term "alkylene-aryl" refers to an alkyl group substituted with an aryl group. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_5$-$C_8$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated, share a carbon atom with another cycloalkyl or heterocycloalkyl group, or fused to another cycloalkyl group, a heterocycloalkyl group, an aryl group and/or a heteroaryl group. Cycloalkyl groups can be saturated or partially unsaturated ring systems optionally substituted with, for example, one to three groups, independently selected alkyl, alkylene-OH, C(O)NH$_2$, NH$_2$, oxo (=O), aryl, haloalkyl, halo, and OH.

As used herein, the term "heterocycloalkyl" or "heterocyclic" is defined similarly as cycloalkyl, except the ring contains one to three heteroatoms independently selected from oxygen, nitrogen, or sulfur. Nonlimiting examples of heterocycloalkyl groups include piperdine, tetrahydrofuran, tetrahydropyran, dihydrofuran, morpholine, and the like. Heterocycloalkyl groups can be saturated or partially unsaturated ring systems optionally substituted with, for example, one to three groups, independently selected alkyl, alkyleneOH, C(O)NH$_2$, NH$_2$, oxo (=O), aryl, haloalkyl, halo, and OH. Heterocycloalkyl groups optionally can be further N-substituted with alkyl, hydroxyalkyl, alkylene-aryl, and alkylene-heteroaryl. The heterocycloalkyl groups described herein can be isolated, share a carbon atom with another cycloalkyl or heterocycloalkyl group, or fused to another heterocycloalkyl group, a cycloalkyl group, an aryl group and/or a heteroaryl group.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, and fluorenyl. Unless otherwise indicated, an aryl group can be an unsubstituted aryl group or a substituted aryl group. Unless otherwise indicated, an aryl group can be fused to a cycloalkyl or heterocycloalkyl group.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, thiophenyl, quinolinyl, isoquinolinyl, benzoxazolyl, benzimidazolyl, and benzothiazolyl. Unless otherwise indicated, a heteroaryl group can be an unsubstituted heteroaryl group or a substituted heteroaryl group.

As used herein, the term "halo" refers to a fluoro, chloro, bromo, or iodo group. the term "haloalkyl" refers to an alkyl group that is substituted with at least one halogen.

A used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms. A substituted chemical functional group can itself include one or more substituents.

The term "alkynyl" is defined identically as "alkyl" except for containing at least one carbon-carbon triple bond, and having two to thirty carbon atoms, for example, two to twenty carbon atoms, or two to ten carbon atoms. The term $C_n$ means the alkynyl group has "n" carbon atoms. For example, $C_4$ alkynyl refers to an alkynyl group that has 4 carbon atoms. $C_2$-$C_7$ alkynyl refers to an alkynyl group having a number of carbon atoms encompassing the entire range (i.e., 2 to 7 carbon atoms), as well as all subgroups (e.g., 2-6, 2-5, 3-6, 2, 3, 4, 5, 6, and 7 carbon atoms). Unless otherwise indicated, an alkynyl group can be an unsubstituted alkynyl group or a substituted alkynyl group.

As used herein, the term "therapeutically effective amount" means an amount of a compound or combination of therapeutically active compounds (e.g., an inhibitor described herein, or a combination of inhibitors) that ameliorates, attenuates or eliminates one or more symptoms of a particular disease or condition (e.g., cancer), or prevents or delays the onset of one of more symptoms of a particular disease or condition.

As used herein, the terms "patient" and "subject" may be used interchangeably and mean animals, such as dogs, cats, cows, horses, and sheep (i.e., non-human animals) and humans. Particular patients are mammals (e.g., humans). The term patient includes males and females.

As used herein, the term "pharmaceutically acceptable" means that the referenced substance, such as a compound of the present invention, or a formulation containing the compound, or a particular excipient, are safe and suitable for administration to a subject or patient. The term "pharmaceutically acceptable carrier" refers to a medium that does not interfere with the effectiveness of the biological activity of the active ingredient(s) and is not toxic to the host to which it is administered.

As used herein the terms "treating", "treat" or "treatment" and the like include preventative (e.g., prophylactic) and palliative treatment.

As used herein, the term "excipient" means any pharmaceutically acceptable additive, carrier, diluent, adjuvant, or other ingredient, other than the active pharmaceutical ingredient (API).

As used herein, the term "Notch transcriptional activation complex" ("NTC") refers to a complex of three proteins, the DNA binding protein CSL, the intracellular domain of Notch ("NICD") and the co-activator protein Mastermind ("MAML1"), which functions to activate transcription of target genes.

As used herein, the phrase "deregulation of the Notch transcriptional activation complex" or "deregulation of the NTC" refers to an abnormality in the regulatory ability of the NTC, resulting in reactivation of gene transcription.

Notch Transcriptional Activation Complex ("NTC") Inhibitors

Disclosed herein are compounds that can inhibit the Notch transcriptional activation complex.

In some embodiments the inhibitors include a compound of Formula (I), or a pharmaceutically acceptable salt thereof:

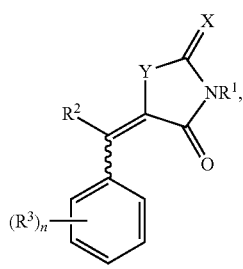

(I)

wherein

∼ represents a bond that results in the adjacent double bond being in either the E or Z configuration;

n is 0, 1, 2, 3, or 4;

X is O or S;

Y is O, S, NH, or $NC_{1-3}$ alkyl;

$R^1$ is selected from the group consisting of H, $C_{1-6}$ alkyl, $C_{1-6}$ alkenyl, $C_{0-6}$ alkylene-$COR^9$, NH-aryl, NH—(C=O)-aryl, $C_{0-6}$ alkylene-cycloalkyl, $C_{0-6}$ alkylene-heterocycloalkyl, $C_{0-6}$ alkylene-heterocycloalkenyl, $C_{0-6}$ alkylene-aryl, $C_{1-6}$ alkylene-$SO_2R^5$, $C_{1-6}$ alkylene-$R^5$, and $C_{0-6}$ alkylene-heteroaryl;

$R^2$ is H or $C_{1-3}$ alkyl;

each $R^3$ is independently selected from the group consisting of $OR^4$, $COOR^4$, $NO_2$, halo, $SO_2R^5$, $C_{1-6}$ alkyl, $C_{1-6}$ alkenyl, $C_{0-6}$ alkylene-cycloalkyl, $C_{0-6}$ alkylene-aryl, $C_{0-6}$ alkylene-heteroaryl, and (C=O)N($R^7$)$_2$;

$R^4$ is selected from the group consisting of H, $C_{1-6}$ alkyl, $C_{1-6}$ alkenyl, $C_{1-6}$ alkynyl, $C_{0-6}$ alkylene-(C=O)$R^8$, $C_{1-6}$ alkylene-N($R^6$)$_2$, $C_{1-6}$ alkylene-CN, $C_{0-6}$ alkylene-aryl, $C_{0-6}$ alkylene-heteroaryl, $C_{1-6}$ alkylene-O-aryl, $C_{1-6}$ alkylene-S-aryl, $C_{1-6}$ alkylene-$NR^6$-aryl, and $C_{1-6}$ alkylene-$NR^6$-heteroaryl;

$R^5$ is OH, N($R^6$)$_2$, NH(C=O)$C_{1-3}$ alkyl, or NH(C=O)aryl;

each $R^6$ is independently H, $C_{1-3}$ alkyl;

each $R^7$ is independently H, $C_{1-3}$ alkyl, $SO_2H$; or $SO_2(C_{1-3}$ alkyl);

$R^8$ is $C_{1-6}$ alkyl, aryl, $OC_{1-6}$ alkyl, or N($R^6$)$_2$;

$R^9$ is OH, N($R^6$)$_2$, $NHSO_2R^6$, $SO_2N(R^6)_2$, and when n is 2 or 3, two adjacent $R^3$ groups, together with the carbon atoms to which they are attached, can form a fused heterocycloalkyl group, a fused aryl group, or a fused heteroaryl group.

In some embodiments, X is O. In some cases, X is S.

In various cases, Y is NH. In some cases, Y is $NC_{1-3}$ alkyl (e.g., NMe or NEt). In some embodiments, Y is O. In various embodiments, Y is S.

In some embodiments, the compound of Formula (I) comprises a compound of Formula (Ia), or a pharmaceutically acceptable salt thereof:

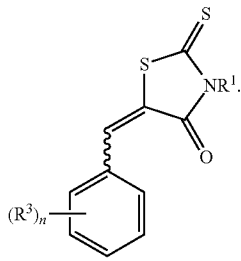

(Ia)

In some embodiments, $R^1$ is H. In some cases, $R^1$ is NH-aryl, NH—(C=O)-aryl, $C_{0-6}$ alkylene-heterocycloalkyl, $C_{0-6}$ alkylene-aryl, or $C_{0-6}$ alkylene-heteroaryl. In various embodiments, $R^1$ is $C_{1-6}$ alkyl (e.g., Me, Et, or Pr), $C_{1-6}$ alkenyl (e.g., $CH_2CH=CH_2$), $C_{0-6}$ alkylene-$COR^9$, $C_{0-6}$ alkylene-cycloalkyl, $C_{0-6}$ alkylene-heterocycloalkenyl, $C_{1-6}$ alkylene-$SO_2R^5$, or $C_{1-6}$ alkylene-$R^5$. In some embodiments, $R^9$ is OH. In some cases, $R^9$ is N($R^6$)$_2$ (e.g., $NH_2$, NHMe, $NMe_2$), $NHSO_2R^6$ (e.g., $NHSO_2H$ or $NHSO_2Me$), or $SO_2N(R^6)_2$ (e.g., $SO_2NH_2$, $SO_2NHMe$, or $SO_2NMe_2$,). For example $R^1$ can be selected from the group consisting of H, Me, Et, Pr, $CH_2CH=CH_2$, $CH_2(C=O)NMe_2$, $CH_2(C=O)NH_2$, $CH_2(C=O)NMe_2$, $CH_2(C=O)NH(SO_2Me)$, $CH_2COOH$, $CH_2CH_2COOH$, $CH_2CH_2CH_2COOH$, CH(Me)COOH, CH(Et)COOH, CH(COOH)$CH_2COOH$, CH(COOH)$CH_2CH_2COOH$, $CH_2$—$SO_2NH_2$, $CH_2$—$SO_2N$(H)Me, NH-phenyl, NH(C=O)-phenyl, NH(C=O)-4-bromophenyl, NH(C=O)-2-chloro-4-methylphenyl,

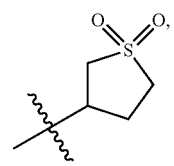 [SMILES: *C1CCS(=O)(=O)C1]

phenyl, 2-ethoxyphenyl, 4-bromophenyl, 4-chlorophenyl, 3-fluorophenyl, 4-fluorophenyl, 4-methoxyphenyl, 4-ethoxyphenyl, 4-nitrophenyl, 3-carboxylphenyl, 3-carboxy-4-hydroxyphenyl, 2-ethoxyphenyl, $CH_2$-phenyl, $CH_2CH_2$-phenyl, $CH_2$-4-methylphenyl, $CH_2$-4-methoxyphenyl, CH(CH$_3$)-phenyl,

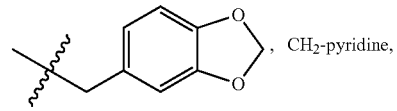, $CH_2$-pyridine,

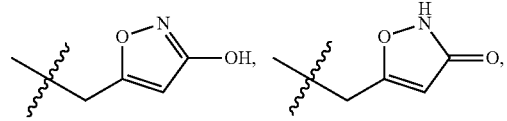

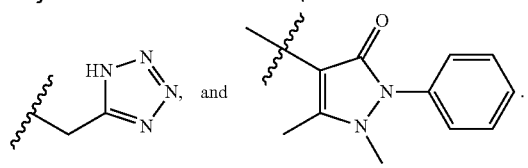

In some embodiments, $R^1$ is selected from H or Me.

In some embodiments, $R^2$ is H. In various embodiments, $R^2$ is $C_{1-3}$ alkyl. For example, $R^2$ is methyl, ethyl, propyl, or isopropyl.

In some embodiments, n is 0. In various embodiments, n is 1. In some cases, n is 2. In some embodiments, n is 3. In various cases, n is 4.

In some embodiments, at least one $R^3$ is $OR^4$.

In some cases when at least one $R^3$ is $OR^4$, $R^4$ is H.

In various cases when at least one $R^3$ is $OR^4$, $R^4$ is $C_{1-6}$ alkyl (e.g., Me, Et, Pr, iPr, Bu, or $OCH_2CH(CH_3)Et$), $C_{1-6}$ alkenyl (e.g., $CH_2CH=CH_2$), or $C_{1-6}$ alkynyl (e.g., $CH_2CCH$). For example, each $R^3$ can independently be selected from the group consisting of OH, OMe, OEt, OPr, OiPr, OBu, $OCH_2CH(CH_3)Et$, $OCH_2CH=CH_2$, and $OCH_2CCH$.

In some embodiments when at least one $R^3$ is $OR^4$, $R^4$ is $C_{1-6}$ alkylene-$N(R^6)_2$, $C_{1-6}$ alkylene-CN, $C_{0-6}$ alkylene-cycloalkyl, $C_{0-6}$ alkylene-aryl, $C_{1-6}$ alkylene-$NR^6$-heteroaryl, $C_{0-6}$ alkylene-heteroaryl, $C_{1-6}$ alkylene-O-aryl, $C_{1-6}$ alkylene-S-aryl, and $C_{1-6}$ alkylene-$NR^6$-aryl. In some of these embodiments, each $R^6$ independently is H, Me, or Et. For example, each $R^3$ can independently be selected from the group consisting of $OCH_2CH(CF_3)N(H)Me$, $OCH_2CN$, O-phenyl, O-2-hydroxyphenyl, O-3-hydroxyphenyl, O-4-hydroxyphenyl, O-2-methoxyphenyl, O-4-methoxyphenyl, $OCH_2$-4-carboxy-phenyl, $OCH_2$-4-methylester-phenyl, $OCH_2$-4-carboxy-phenyl, $OCH_2CH_2O$-phenyl, $OCH_2CH_2O$-2-methylphenyl, $OCH_2CH_2O$-3-methylphenyl, $OCH_2CH_2O$-4-methylphenyl, $OCH_2CH_2O$-2-methoxyphenyl, $OCH_2CH_2O$-2-chlorophenyl, $OCH_2CH_2CH_2O$-2,4-dimethylphenyl, $OCH_2CH(CH_3)CH_2$—O-phenyl, $OCH_2CH_2O$-2,3-dimethylphenyl, $OCH_2CH_2CH_2$—O-2,4-dimethylphenyl, $OCH_2CH_2O$-3-methylphenyl, $OCH_2CH_2O$-4-methylphenyl, $OCH_2CH_2CH_2O$-2-chlorophenyl, $OCH_2CH_2CH_2O$-4-chlorophenyl, $OCH_2CH_2CH_2$—O-3,4-dimethylphenyl, $OCH_2CH_2CH_2$—O-3,5-dimethylphenyl, $OCH_2CH_2S$-4-methylphenyl, $OCH_2CH_2S$-4-chlorophenyl,

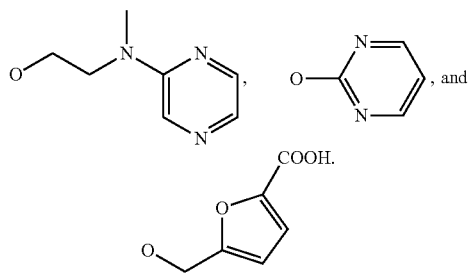

In some embodiments when at least one $R^3$ is $OR^4$, $R^4$ is $C_{0-6}$ alkylene-$(C=O)R^8$. In some cases, $R^8$ is $C_{1-6}$ alkyl or aryl. For example, each $R^3$ can independently be selected from the group consisting of $OCH_2COOH$, $OCH_2CH_2COOH$, $OCH_2CH_2CH_2COOH$, $OCH(Me)COOH$, $O(C=O)Me$, $O(C=O)Et$, $O(C=O)Ph$, $OCH_2(C=O)Me$, and $OCH_2(C=O)Et$. In some cases, $R^8$ is $OC_{1-6}$ alkyl or $N(R^6)_2$. In some of these embodiments, each $R^6$ can independently be H, Me, or Et. For example, each $R^3$ can independently be selected from the group consisting of $OCH_2COOMe$, $OCH_2COOEt$, $OCH_2(C=O)NH_2$, $OCH_2(C=O)N(H)Me$, and $OCH_2(C=O)N(Me)_2$.

In some cases, at least one $R^3$ is selected from the group consisting of halo (e.g., F, Cl, Br, or I), $C_{1-6}$ alkyl (e.g., Me, Et, or Pr), $C_{1-6}$ alkenyl (e.g., $CH_2CH=CH_2$), $C_{0-6}$ alkylene-aryl, and $C_{0-6}$ alkylene-heteroaryl. For example, each $R^3$ can independently be selected from the group consisting of F, Cl, Br, Me, Et, Pr, $CH_2CH=CH_2$, phenyl, 4-hydroxyphenyl, 3-methoxyphenyl,

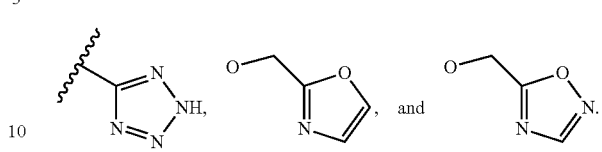

In various embodiments, at least one $R^3$ is selected from the group consisting of COOH, $NO_2$, $SO_2R^5$, and $(C=O)N(R^7)_2$. In some cases, $R^5$ is selected from the group consisting of H, $NH_2$, NHMe, $NMe_2$, and $NH(C=O)Me$. In various cases, $R^7$ is selected from the group consisting of H, Me, $SO_2H$, and $SO_2Me$. For example, each $R^3$ can independently be selected from the group consisting of $SO_3NH_2$, $SO_3NH(C=O)Me$, and $C=ON(H)SO_2Me$.

In some embodiments, two adjacent $R^3$ groups, together with the carbon atoms to which they are attached form a fused heterocycloalkyl group (e.g., dioxole or dihydrofuran), a fused aryl group (e.g., phenyl), or a fused heteroaryl group. In some of these cases, the compound of Formula (I) can include a compound selected from the group consisting of

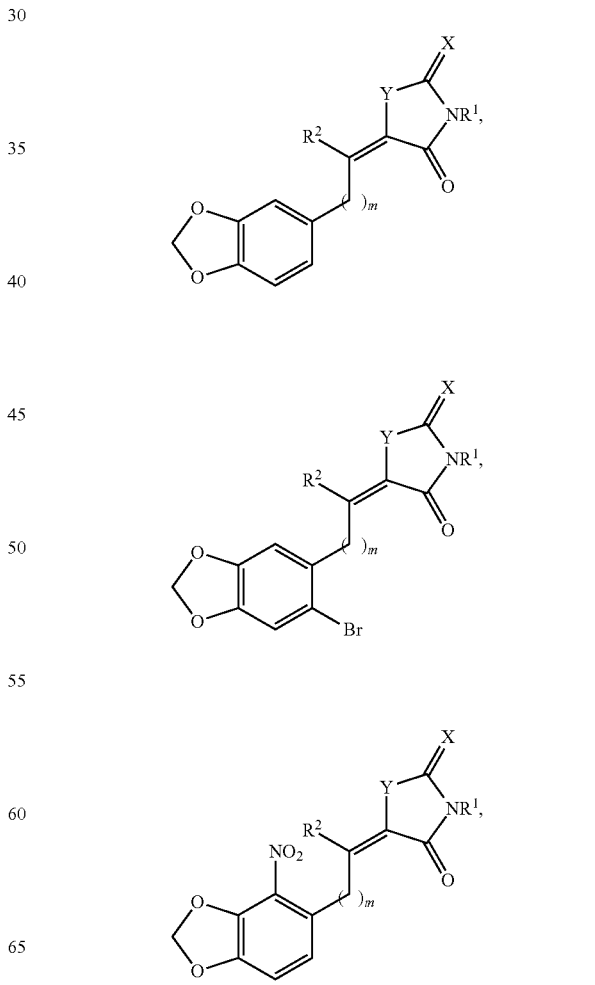

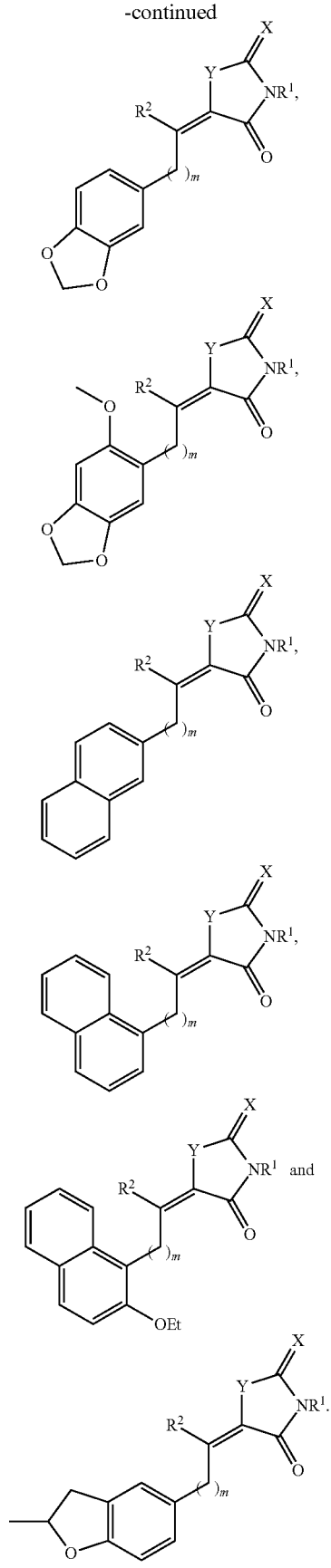

In some embodiments, these compounds have Z stereochemistry.

In some embodiments, each $R^3$ is independently selected from the group consisting of OH, OMe, OEt, OCH$_2$COOH, OCH$_2$CH=CH$_2$, OCH$_2$CCH, dioxole, F, Cl, and Br. In some cases, each $R^3$ is independently selected from the group consisting of OMe, OEt, OH, and OCH$_2$COOH.

In some cases, n is 2 or 3, and each $R^3$ is $OR^4$ or halo. In various embodiments, one $R^3$ is OH and one $R^3$ is $OC_{1-6}$ alkyl or halo. In some embodiments, n is 2, one $R^3$ is OH, and the other $R^3$ is $OC_{1-6}$ alkyl. In some of these embodiments, the OH is ortho to the alkene. For example, the compound of Formula (I) can include a compound of Formula (Ib), or a pharmaceutically acceptable salt thereof:

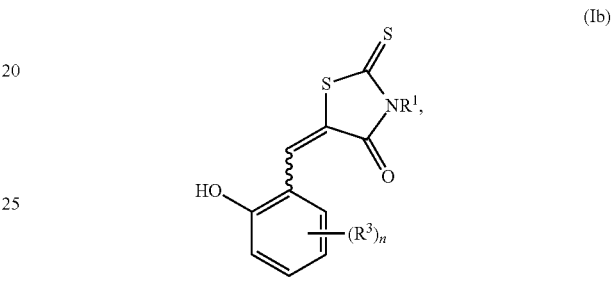

wherein n is 1 or 2.

In some of these cases (i.e., "the 2-hydroxyphenyl series"), each $R^3$ independently is an electron donating substituent, such as $OR^4$. For example, $R^3$ can be $OC_{1-6}$ alkyl, such as OMe or OEt. In some cases, n is 1 and the $OC_{1-6}$ alkyl group is para to the OH group.

In some cases when n is 2 and one $R^3$ is OH, the OH is meta position to the double bond (i.e., "the 3-hydroxyphenyl series"). In some of these embodiments, the other $R^3$ is $OR^4$ (e.g., $OC_{1-6}$ alkyl), and is positioned meta to both the OH group and the double bond.

In any of the embodiments described herein, ∼ can represent a bond that results in the adjacent double bond being in the Z configuration. For example, Formula (I), (Ia), and (Ib) can have the stereochemistry shown below.

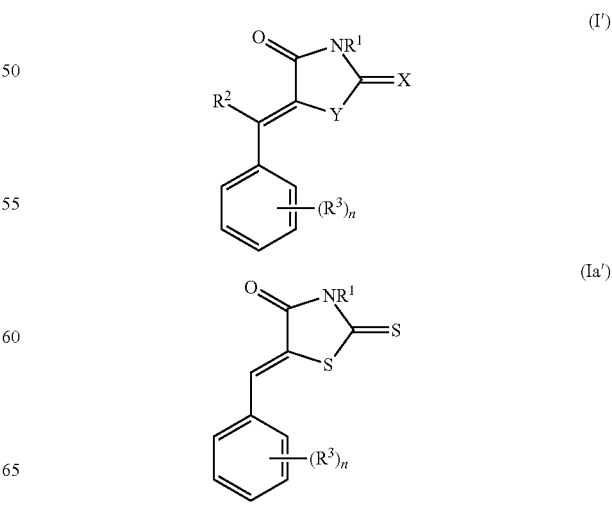

-continued
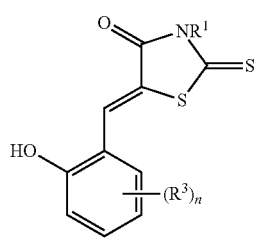
(Ib')
In some cases, the compound of Formula (I) is selected from a compound listed in Table 1.
TABLE 1
Identification No.
Structure
Screen Results at 8 μM
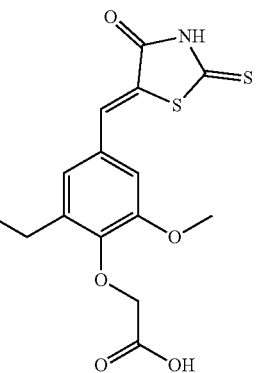
1-134
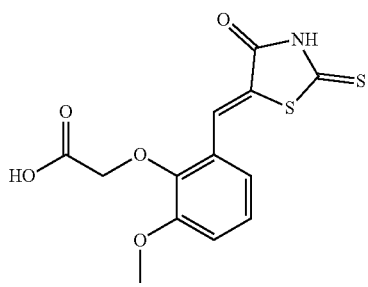 [SMILES: COc1cccc(/C=C2\SC(=S)NC2=O)c1OCC(=O)O]
1-134-01
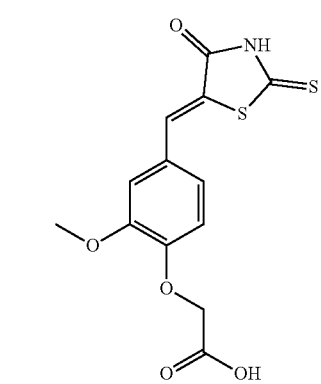 [SMILES: COc1cc(/C=C2\SC(=S)NC2=O)ccc1OCC(=O)O]
1-134-02
TABLE 1-continued
Identification No.
Structure
Screen Results at 8 μM
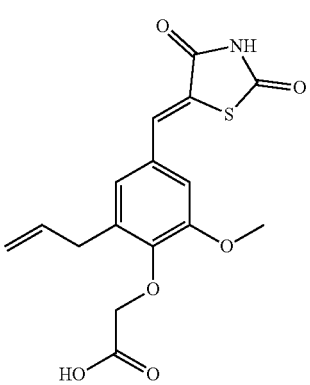 [SMILES: C=CCc1cc(/C=C2\SC(=O)NC2=O)cc(OC)c1OCC(=O)O]
1-134-03
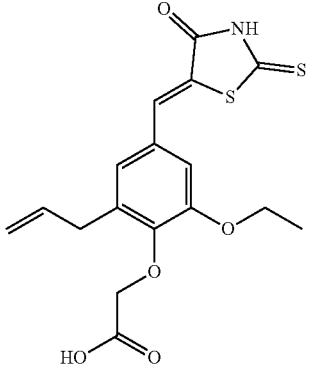 [SMILES: C=CCc1cc(/C=C2\SC(=S)NC2=O)cc(OCC)c1OCC(=O)O]
1-134-04
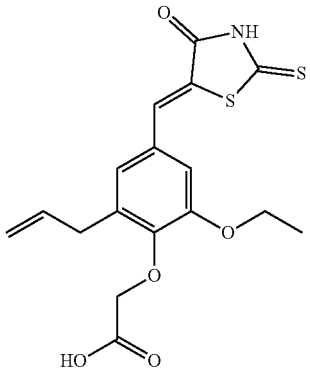 [SMILES: C=CCc1cc(/C=C2\SC(=S)NC2=O)cc(OCC)c1OCC(=O)O]
1-134-06
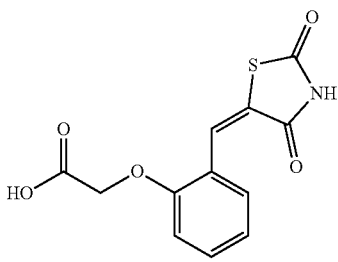 [SMILES: O=C(O)COc1ccccc1/C=C1/SC(=O)NC1=O]
1-134-07

TABLE 1-continued
| Identification No. Structure Screen Results at 8 μM | |
|---|---|
| 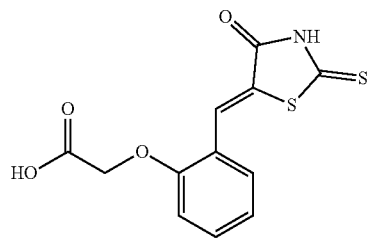 | 1-134-09 |
| 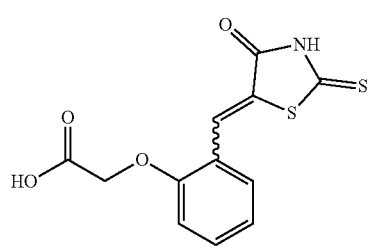 [SMILES: O=C(O)COc1ccccc1C=C1SC(=S)NC1=O] | 1-134-10 |
| 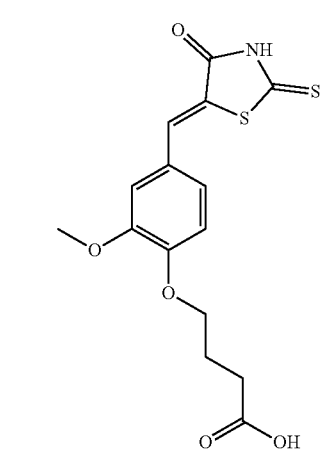 [SMILES: COc1cc(/C=C2\SC(=S)NC2=O)ccc1OCCCC(=O)O] | 1-134-13 |
| 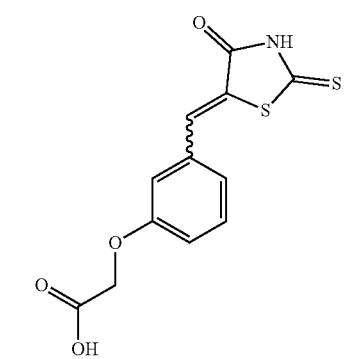 [SMILES: O=C(O)COc1cccc(C=C2SC(=S)NC2=O)c1]  | 1-134-20 |
| 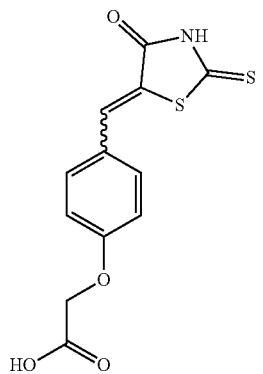 [SMILES: O=C(O)COc1ccc(C=C2SC(=S)NC2=O)cc1] | 1-134-22 |
| 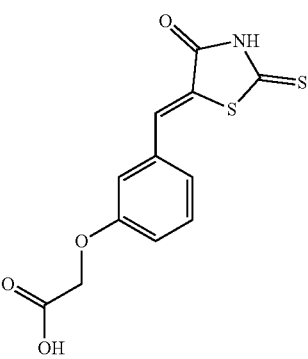 [SMILES: O=C(O)COc1cccc(/C=C2\SC(=S)NC2=O)c1] | 1-134-24 |
| 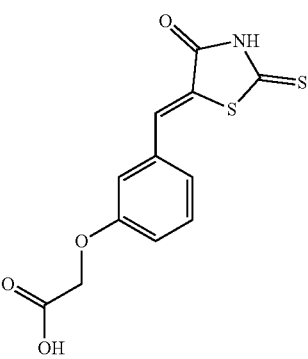 [SMILES: O=C(O)COc1cccc(/C=C2\SC(=S)NC2=O)c1] | 1-134-25 |
Note: the last two rows show different structures (1-134-24 and 1-134-25).

TABLE 1-continued
Identification No.
Structure
Screen Results at 8 μM
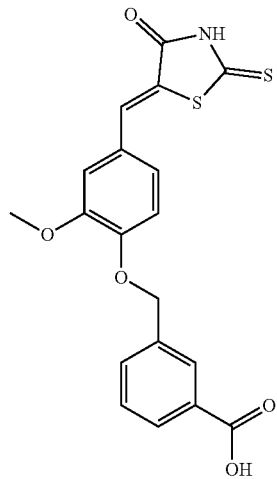 [SMILES: COc1cc(/C=C2\SC(=S)NC2=O)ccc1OCc1cccc(C(=O)O)c1]
1-134-26
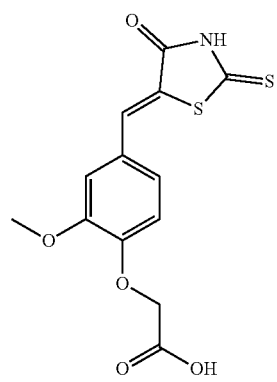 [SMILES: COc1cc(/C=C2\SC(=S)NC2=O)ccc1OCC(=O)O]
1-134-27
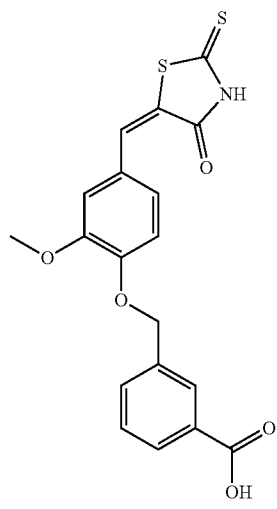 [SMILES: COc1cc(/C=C2/SC(=S)NC2=O)ccc1OCc1cccc(C(=O)O)c1]
1-134-29
TABLE 1-continued
Identification No.
Structure
Screen Results at 8 μM
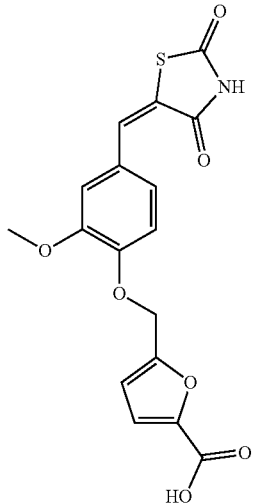 [SMILES: COc1cc(/C=C2/SC(=O)NC2=O)ccc1OCc1ccc(C(=O)O)o1]
1-134-31
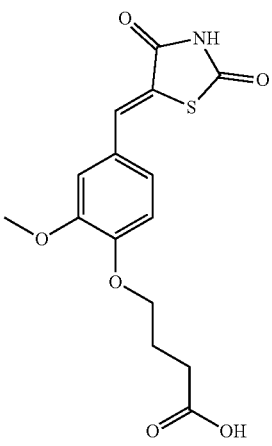 [SMILES: COc1cc(/C=C2\SC(=O)NC2=O)ccc1OCCCC(=O)O]
1-134-32
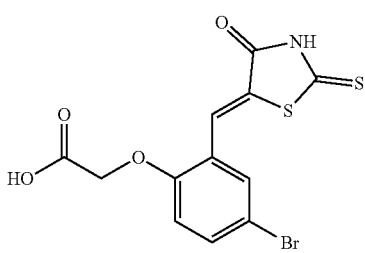 [SMILES: O=C(O)COc1ccc(Br)cc1/C=C1\SC(=S)NC1=O]
1-134-36
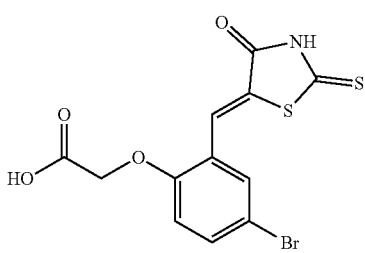 [SMILES: O=C(O)COc1ccc(Br)cc1/C=C1\SC(=S)NC1=O]
1-134-37

TABLE 1-continued
Identification No.
Structure
Screen Results at 8 µM
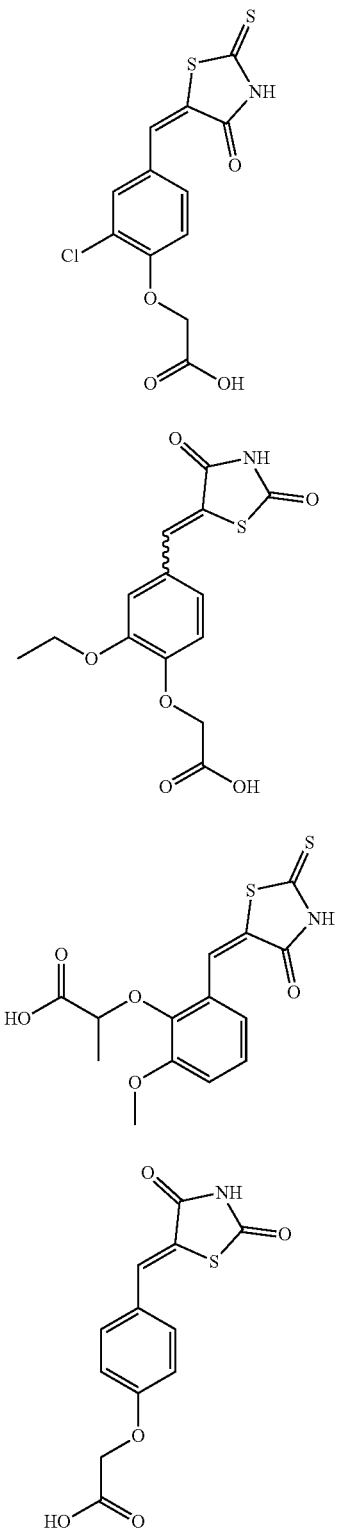
1-134-38
1-134-39
1-134-40
1-134-44
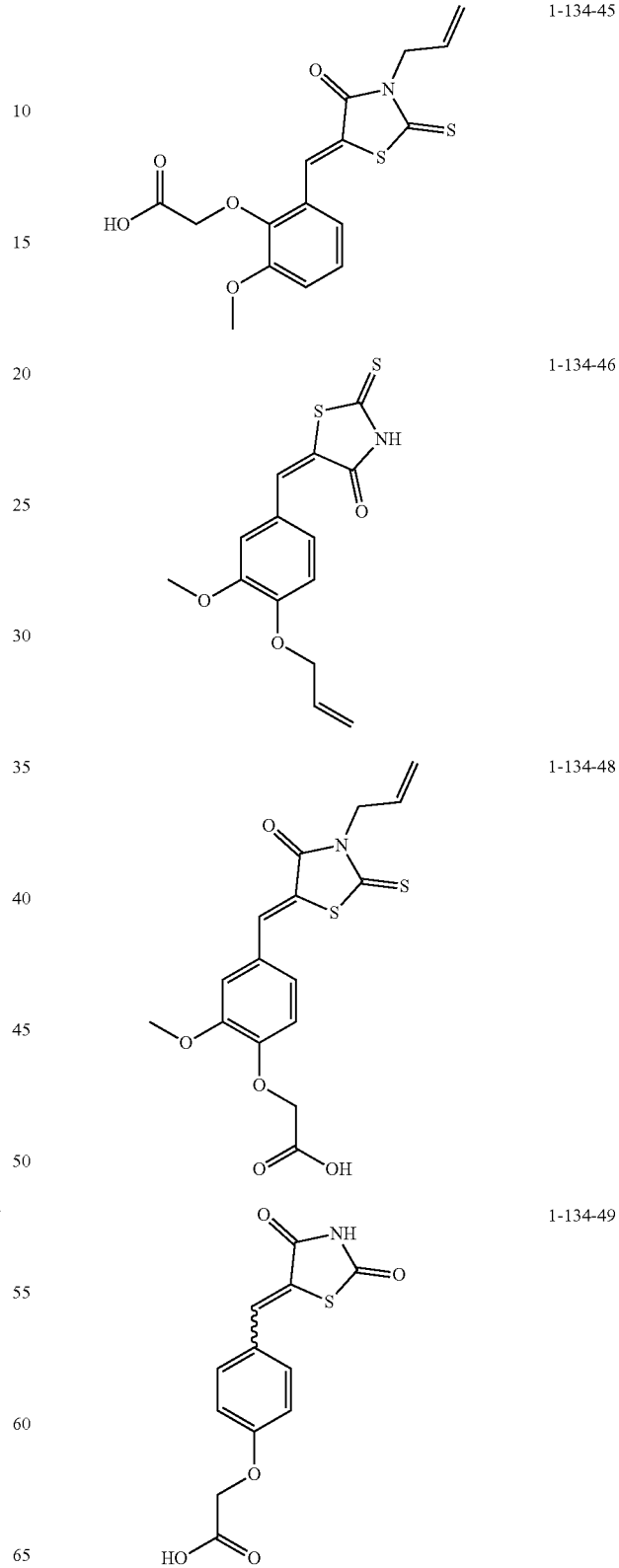
1-134-45
1-134-46
1-134-48
1-134-49

TABLE 1-continued

Identification No.
Structure
Screen Results at 8 μM

| Structure | ID |
|---|---|
| (structure) | 1-134-52 |
| (structure) | 1-134-57 |
| (structure) | 1-134-59 |
| (structure) | 1-134-60 |
| (structure) | 1-134-61 |
| (structure) | 1-134-63 |
| (structure) | 1-134-64 |
| (structure) | 1-134-65 |
| (structure) | 1-134-66 |

TABLE 1-continued
Identification No.
Structure
Screen Results at 8 μM
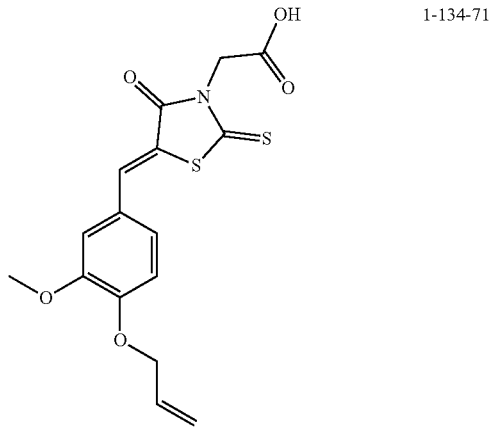
1-134-71
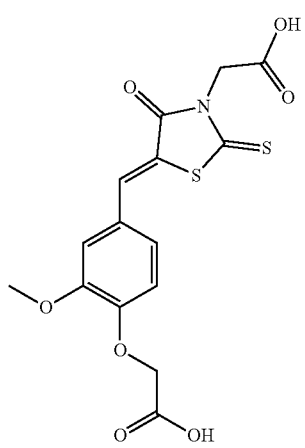 [SMILES: COc1cc(/C=C2\SC(=S)N(CC(=O)O)C2=O)ccc1OCC(=O)O]
1-134-74
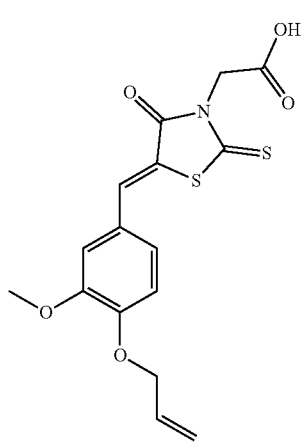 [SMILES: C=CCOc1ccc(/C=C2\SC(=S)N(CC(=O)O)C2=O)cc1OC]
1-134-78
TABLE 1-continued
Identification No.
Structure
Screen Results at 8 μM
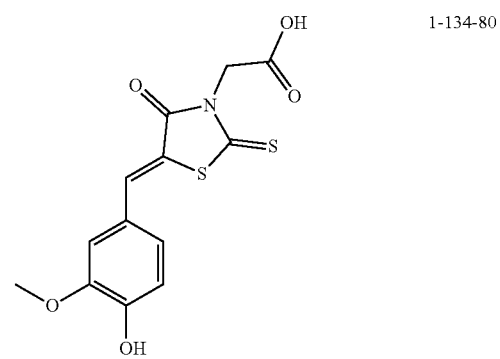
1-134-80
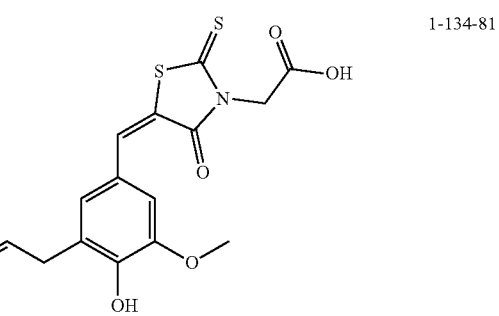
1-134-81
1-134-82

TABLE 1-continued
| Identification No. Structure Screen Results at 8 μM | |
|---|---|
| 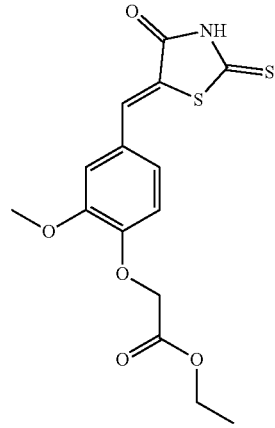 | 1-134-83 |
| | 1-134-84 |
| | 1-134-87 |
TABLE 1-continued
| Identification No. Structure Screen Results at 8 μM | |
|---|---|
| | 1-134-88 |
| 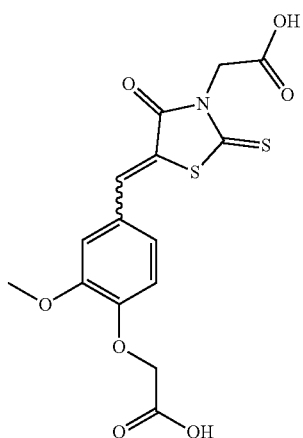 [SMILES: COc1cc(C=C2SC(=S)N(CC(=O)O)C2=O)ccc1OCC(=O)O] | 1-134-90 |
| 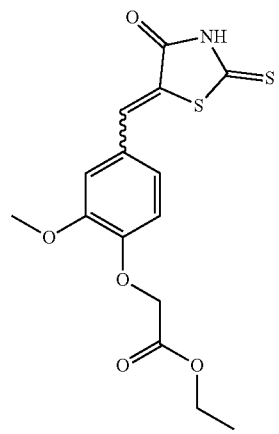 [SMILES: CCOC(=O)COc1ccc(C=C2SC(=S)NC2=O)cc1OC] | 1-134-91 |

TABLE 1-continued

| Identification No. Structure Screen Results at 8 μM |
|---|
| 1-134-97 |
| 1-134-99 |
| NADi-003<br>0.289 |
| NADi-004<br>0.376 |
| NADi-005<br>0.386 |
| NADi-006<br>0.389 |

TABLE 1-continued
Identification No.
Structure
Screen Results at 8 μM
NADi-007
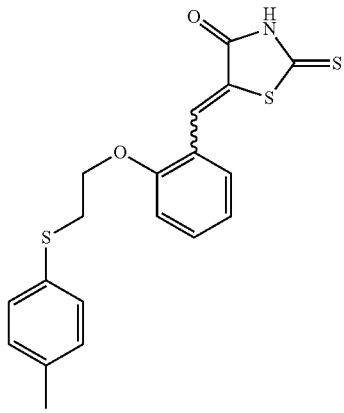
0.443
NADi-008
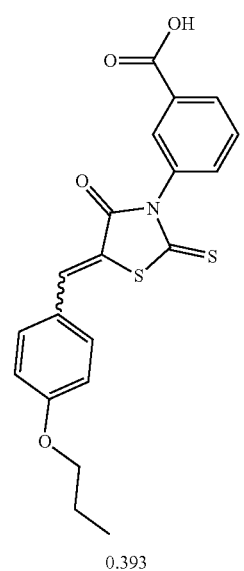 [SMILES: CCCOc1ccc(C=C2SC(=S)N(c3cccc(C(=O)O)c3)C2=O)cc1]
0.393
NADi-009
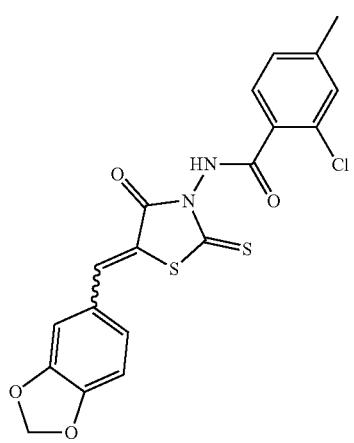
0.462
TABLE 1-continued
Identification No.
Structure
Screen Results at 8 μM
NADi-010
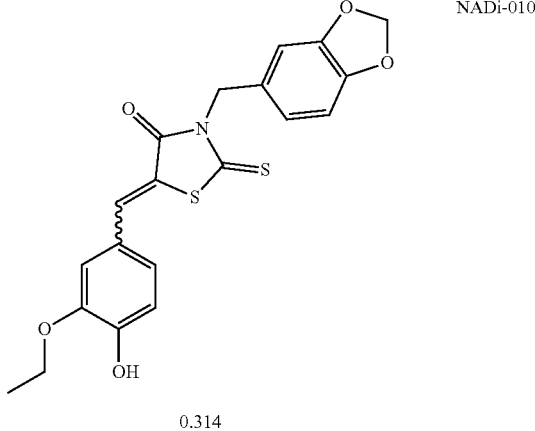
0.314
NADi-011
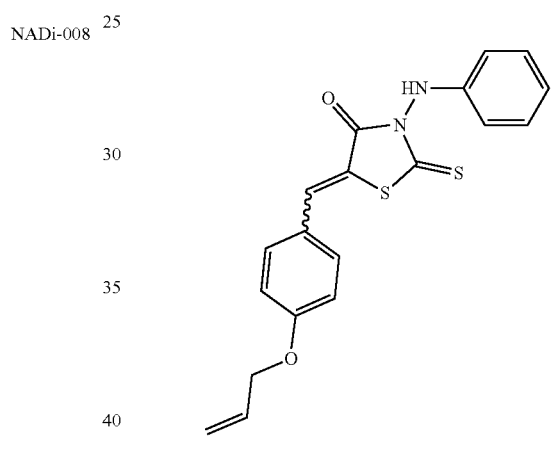
0.36
NADi-012
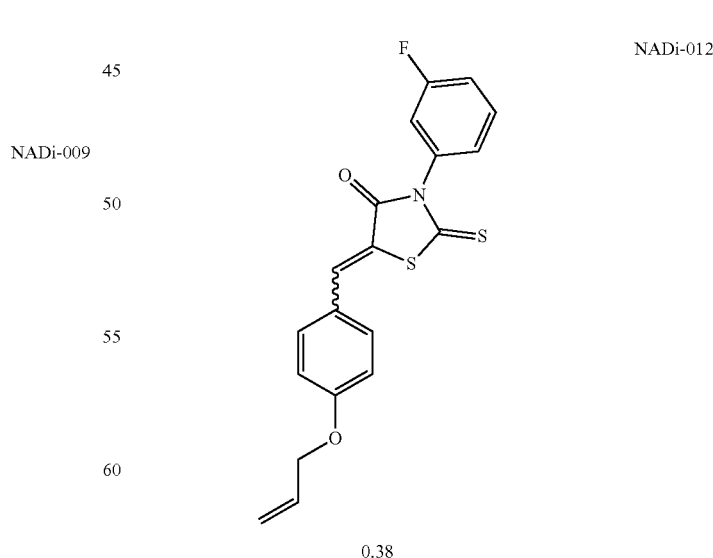
0.38

TABLE 1-continued
Identification No.
Structure
Screen Results at 8 μM
NADi-013
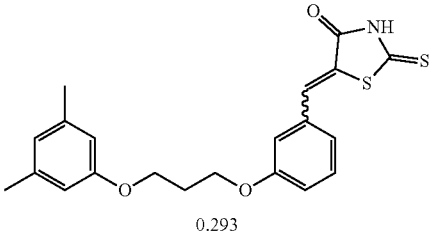 [SMILES: Cc1cc(C)cc(OCCCOc2cccc(C=C3SC(=S)NC3=O)c2)c1]
0.401
NADi-014
0.424
NADi-015
0.431
NADi-016
0.167
TABLE 1-continued
Identification No.
Structure
Screen Results at 8 μM
NADi-017
0.293
NADi-018
0.343
NADi-019
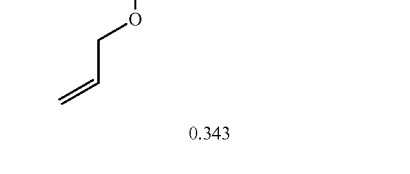
0.409

TABLE 1-continued
Identification No.
Structure
Screen Results at 8 μM
NADi-020
0.433
NADi-021
0.477
NADi-022
0.437
NADi-023
0.345
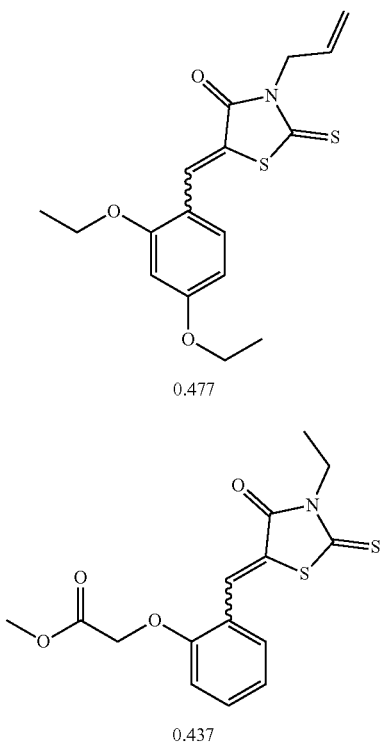
TABLE 1-continued
Identification No.
Structure
Screen Results at 8 μM
NADi-024
0.364
NADi-025
0.481
NADi-026
0.356
NADi-027
0.47
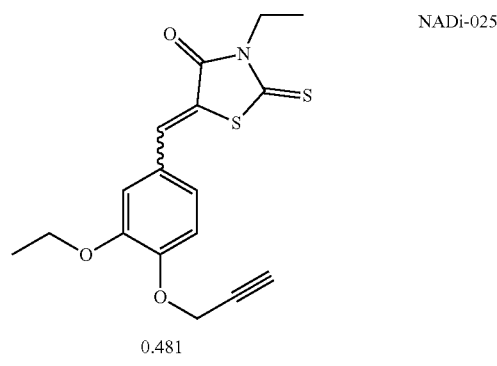

TABLE 1-continued

Identification No.
Structure
Screen Results at 8 μM

NADi-028

0.492

NADi-029

0.487

NADi-030

0.419

NADi-031

0.454

TABLE 1-continued

Identification No.
Structure
Screen Results at 8 μM

NADi-032

0.431

NADi-033

0.281

NADi-034

0.38

TABLE 1-continued
Identification No.
Structure
Screen Results at 8 μM
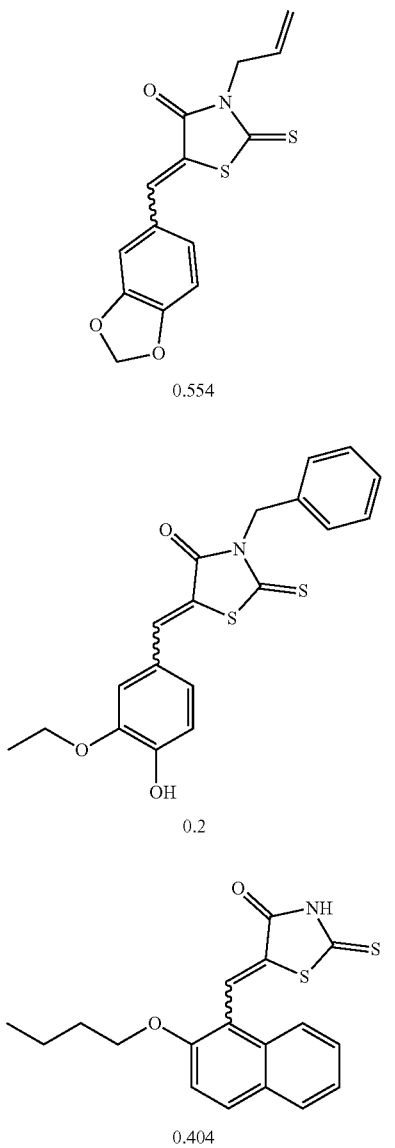
NADi-035
0.554
NADi-036
0.2
NADi-037
0.404
NADi-038
0.461
TABLE 1-continued
Identification No.
Structure
Screen Results at 8 μM
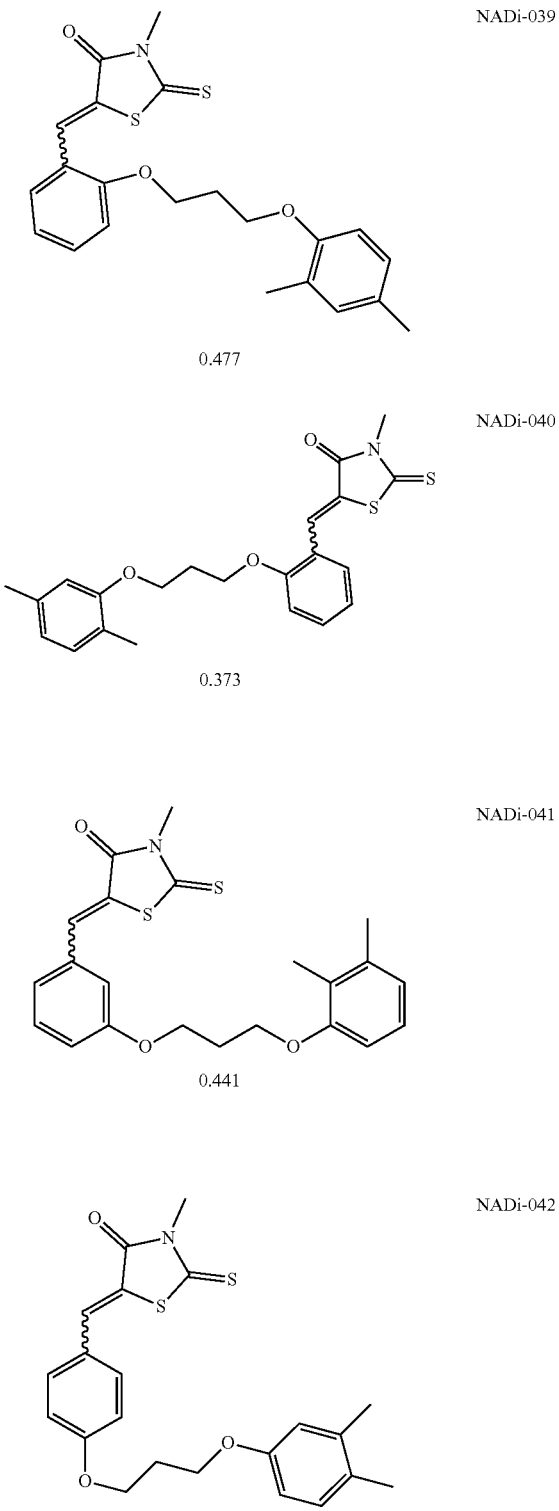
NADi-039
0.477
NADi-040
0.373
NADi-041
0.441
NADi-042
0.355

TABLE 1-continued
Identification No.
Structure
Screen Results at 8 μM
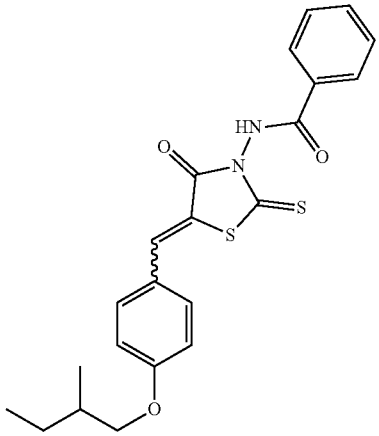
NADi-043
0.304
NADi-044
0.452
NADi-045
0.433
NADi-046
0.391
NADi-047
0.484
NADi-048
0.396

TABLE 1-continued
| Identification No. Structure Screen Results at 8 μM |
|---|
NADi-049
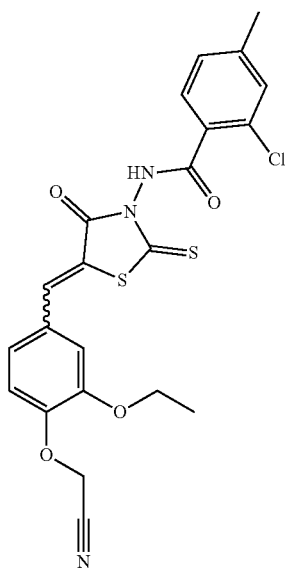
0.241
NADi-050
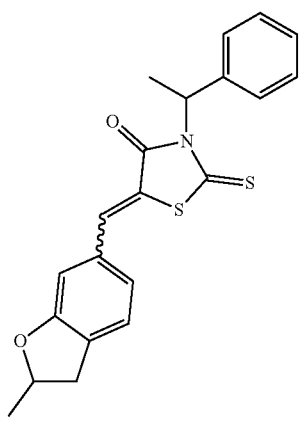
0.422
NADi-051
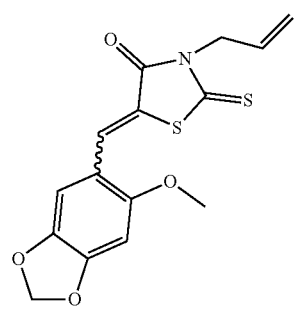
0.43
NADi-052
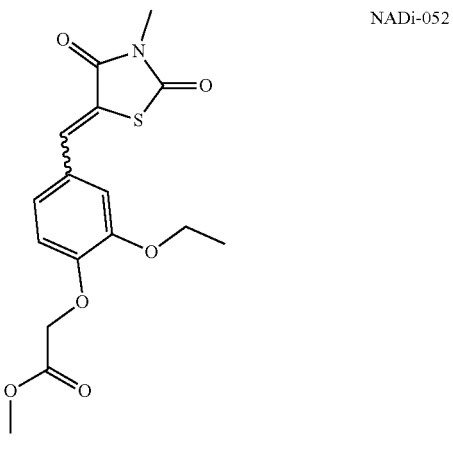
0.399
NADi-053
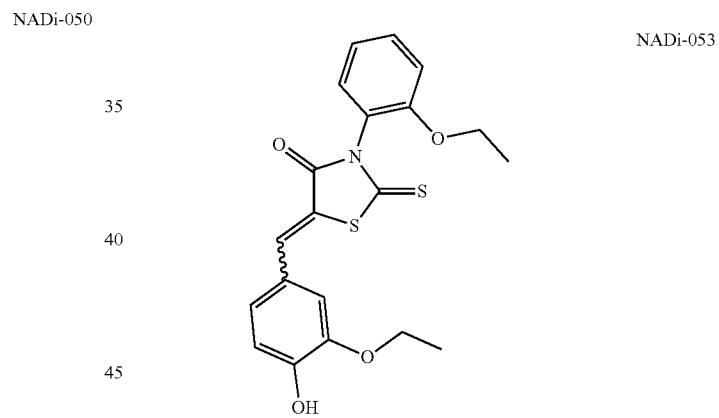
0.463
NADi-054
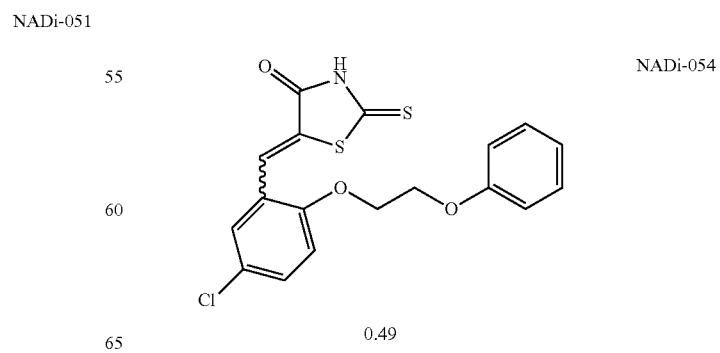
0.49

TABLE 1-continued
| Identification No. Structure Screen Results at 8 μM |
|---|
| NADi-055 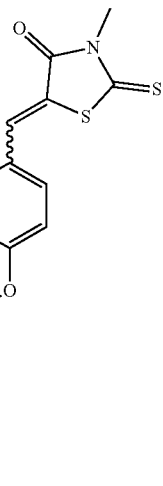 0.27 |
| NADi-056 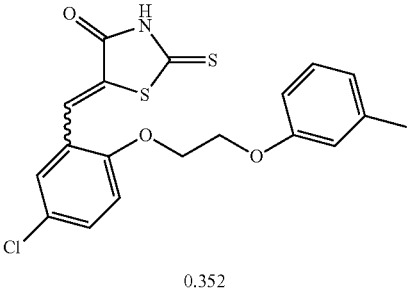 [SMILES: Cc1cccc(OCCOc2ccc(Cl)cc2C=C2SC(=S)NC2=O)c1] 0.322 |
| NADi-057 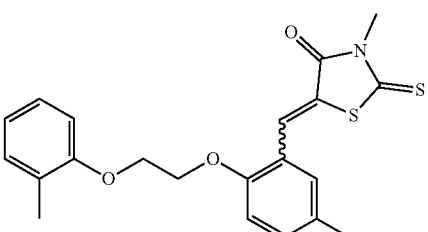 0.259 |
| NADi-058 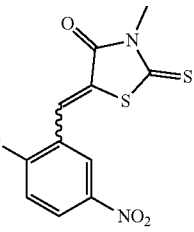 0.339 |
| NADi-059 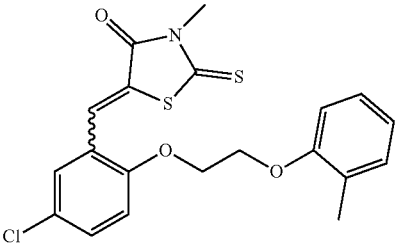 0.352 |
| NADi-060 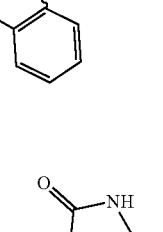 0.341 |
| NADi-061 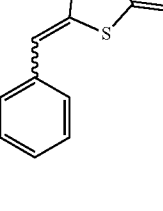 0.308 |
| NADi-062 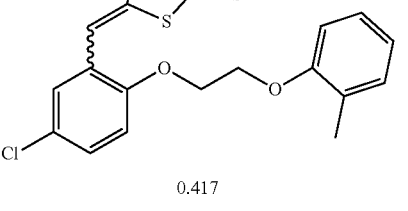 0.417 |

TABLE 1-continued
Identification No.
Structure
Screen Results at 8 μM
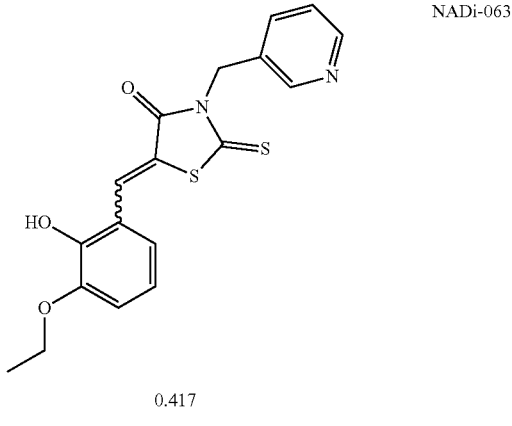
NADi-063
0.417
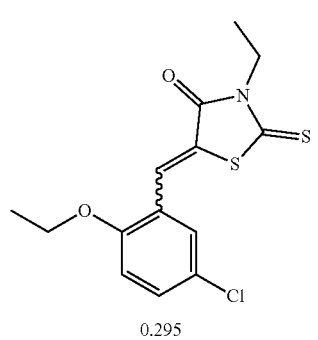 [SMILES: CCOc1ccc(Cl)cc1C=C1SC(=S)N(CC)C1=O]
NADi-064
0.295
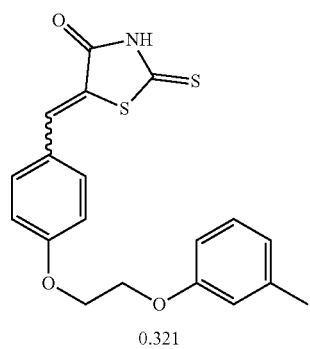 [SMILES: Cc1cccc(OCCOc2ccc(C=C3SC(=S)NC3=O)cc2)c1]
NADi-065
0.321
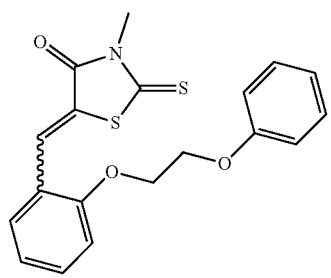
NADi-066
0.371
TABLE 1-continued
Identification No.
Structure
Screen Results at 8 μM
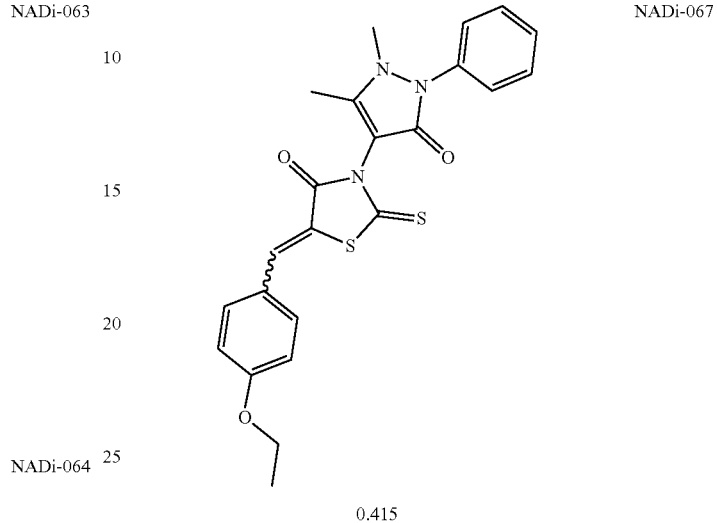
NADi-067
0.415
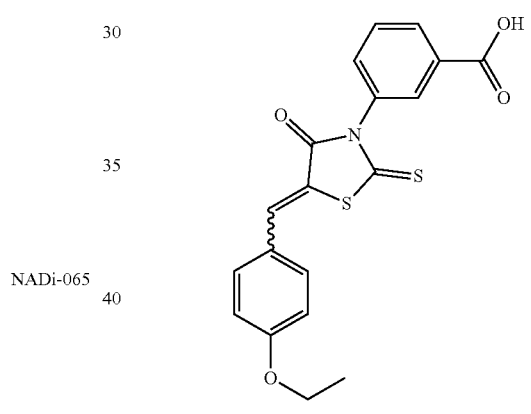
NADi-068
0.41
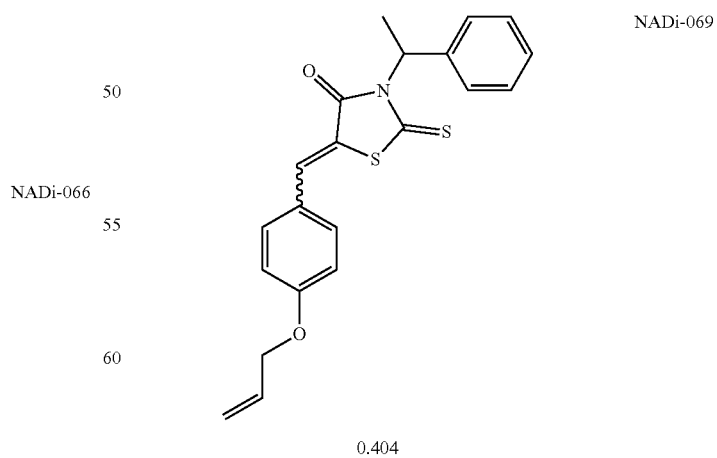
NADi-069
0.404

TABLE 1-continued

| Identification No. Structure Screen Results at 8 μM |
|---|
| NADi-070 0.344 |
| NADi-071 0.179 |
| NADi-072 0.36 |
| NADi-073 0.372 |
| NADi-074 0.456 |
| NADi-075 0.4 |

TABLE 1-continued
Identification No.
Structure
Screen Results at 8 μM
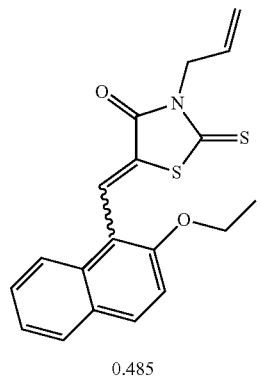 [SMILES: C=CCN1C(=O)C(=Cc2c(OCC)ccc3ccccc23)SC1=S]
NADi-076
0.485
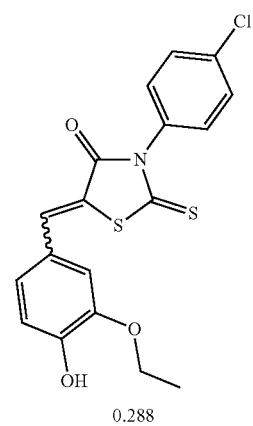 [SMILES: CCOc1cc(C=C2SC(=S)N(c3ccc(Cl)cc3)C2=O)ccc1O]
NADi-077
0.288
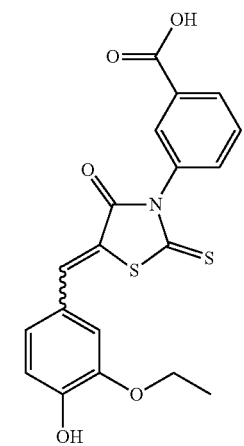
NADi-078
0.407
TABLE 1-continued
Identification No.
Structure
Screen Results at 8 μM
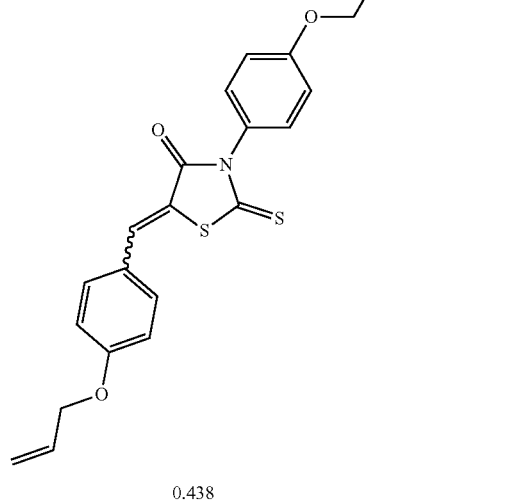
NADi-079
0.438
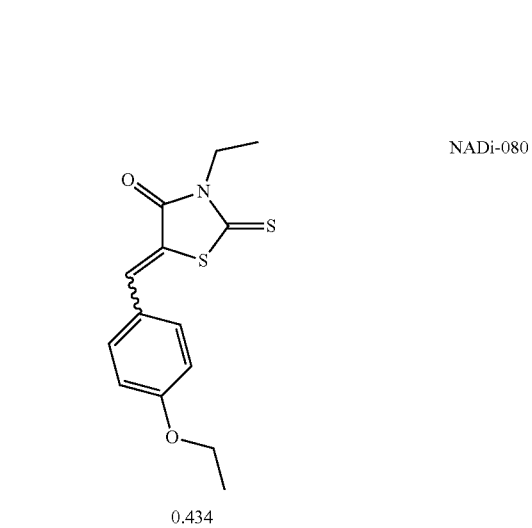
NADi-080
0.434
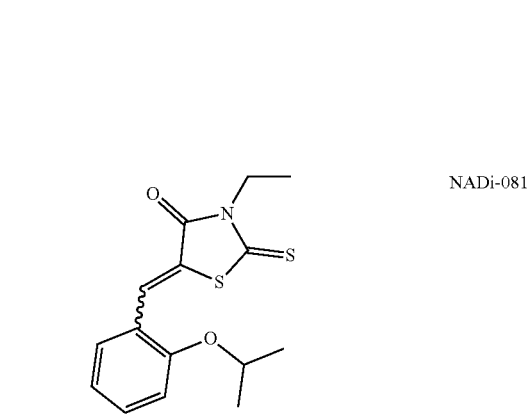
NADi-081
0.438

TABLE 1-continued

Identification No.
Structure
Screen Results at 8 μM

NADi-082
0.393

NADi-083
0.509

NADi-084
0.369

NADi-085
0.334

NADi-090

NADi-091

NADi-093

NADi-094
0.372

NADi-095
0.297

TABLE 1-continued
| Identification No. Structure Screen Results at 8 μM | |
|---|---|
| 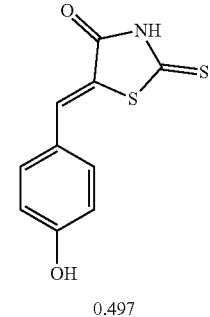 [SMILES: O=C1NC(=S)S/C1=C\c1ccc(O)cc1] 0.492 (with NADi-096, NADi-097, NADi-098 structures above) | NADi-096<br><br>NADi-097<br><br>NADi-098 |
| 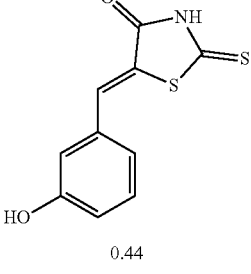 0.319 | NADi-099 |
| 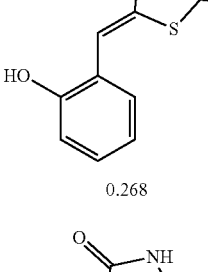 0.451 | NADi-100 |
| 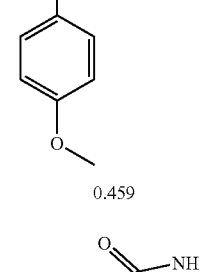 0.497<br><br>0.44<br><br>0.268 | NADi-101<br><br>NADi-102<br><br>NADi-103 |
| 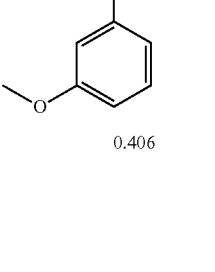 0.459<br><br>0.406 | NADi-104<br><br>NADi-105 |

TABLE 1-continued

| Identification No. Structure Screen Results at 8 µM |
|---|
| NADi-106, 2-methoxybenzylidene rhodanine, 0.411 |
| NADi-107, 3-allyl-4-hydroxy-5-methoxybenzylidene rhodanine, 0.479 |
| NADi-108, 3-allyl-4-hydroxy-5-methoxybenzylidene rhodanine (thiazolidinedione variant) |
| NADi-109, 3-allyl-4-hydroxy-5-methoxybenzylidene oxazolidinedione |
| NADi-110, 3-allyl-4-hydroxy-5-methoxybenzylidene hydantoin |
| NADi-113, 4-carboxybenzylidene rhodanine, 0.477 |
| NADi-117, 3-fluoro-2-hydroxybenzylidene rhodanine, 0.253 |
| NADi-118, 4-fluoro-2-hydroxybenzylidene rhodanine |
| NADi-119, 5-fluoro-2-hydroxybenzylidene rhodanine, 0.208 |
| NADi-120, 6-fluoro-2-hydroxybenzylidene rhodanine |

TABLE 1-continued

Identification No.
Structure
Screen Results at 8 μM

NADi-121

0.42

NADi-122

0.414

NADi-123

0.119

NADi-124

NADi-125

TABLE 1-continued

Identification No.
Structure
Screen Results at 8 μM

NADi-126

NADi-127

NADi-128

NADi-129

NADi-130

0.344

TABLE 1-continued

| Identification No. Structure Screen Results at 8 μM | |
|---|---|
| (3-hydroxy-5-methoxybenzylidene rhodanine) | NADi-131 |
| (2-methoxy-5-hydroxybenzylidene rhodanine) | NADi-132 |
| (2-(1H-tetrazol-5-yl)benzylidene rhodanine) | NADi-133 |
| (3-(1H-tetrazol-5-yl)benzylidene rhodanine) | NADi-134 |
| (4-(1H-tetrazol-5-yl)benzylidene rhodanine) | NADi-135 |
| (2-hydroxy-3-chlorobenzylidene rhodanine) | NADi-136 |
| (2-hydroxy-4-chlorobenzylidene rhodanine) | NADi-137 |
| (2-hydroxy-5-chlorobenzylidene rhodanine) 0.233 | NADi-138 |
| (2-hydroxy-6-chlorobenzylidene rhodanine) | NADi-139 |
| (2-(carboxymethoxy)-6-chlorobenzylidene rhodanine) 0.161 | NADi-140 |

TABLE 1-continued

| Identification No. Structure Screen Results at 8 μM |
|---|
| NADi-141 |
| NADi-142 |
| NADi-143 |
| NADi-144 |
| NADi-145 |

TABLE 1-continued

| Identification No. Structure Screen Results at 8 μM |
|---|
| NADi-146 0.406 |
| NADi-147 0.564 |
| NADi-148 |
| NADi-149 |
| NADi-150 |

TABLE 1-continued

Identification No.
Structure
Screen Results at 8 μM

NADi-151
0.414

NADi-152

NADi-153

NADi-154

NADi-155
0.435

TABLE 1-continued

Identification No.
Structure
Screen Results at 8 μM

NADi-156

NADi-157

NADi-158
0.324

NADi-159
0.392

TABLE 1-continued

| Identification No. Structure Screen Results at 8 μM |
|---|

NADi-160

NADi-161

NADi-162

NADi-163

0.477

NADi-164

TABLE 1-continued

| Identification No. Structure Screen Results at 8 μM |
|---|

NADi-165

NADi-166

NADi-167

0.426

NADi-168

TABLE 1-continued
| Identification No. Structure Screen Results at 8 μM |
|---|
| 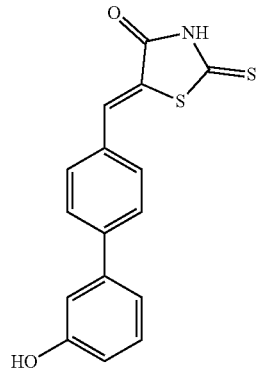 [SMILES: O=C1NC(=S)S/C1=C\c1ccc(-c2cccc(O)c2)cc1] NADi-169 |
| 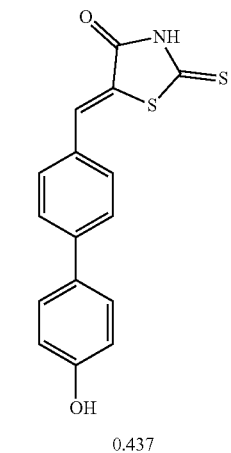 [SMILES: O=C1NC(=S)S/C1=C\c1ccc(-c2ccc(O)cc2)cc1] NADi-170<br>0.437 |
| 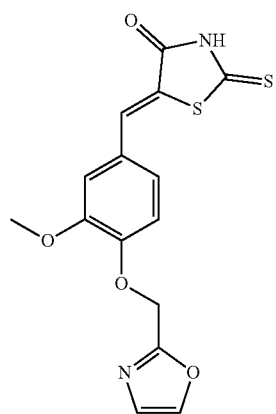 [SMILES: COc1cc(/C=C2\SC(=S)NC2=O)ccc1OCc1ncco1] NADi-176 |
TABLE 1-continued
| Identification No. Structure Screen Results at 8 μM |
|---|
| 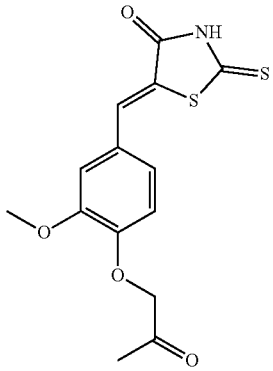 NADi-177<br>0.485 |
| 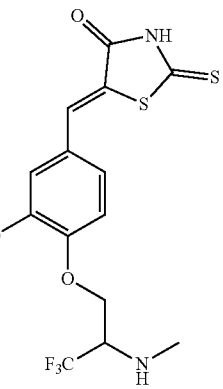 NADi-178 |
| 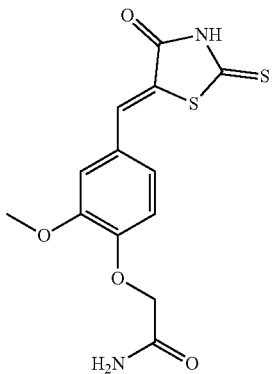 NADi-179<br>0.439 |

TABLE 1-continued
Identification No.
Structure
Screen Results at 8 μM
NADi-180
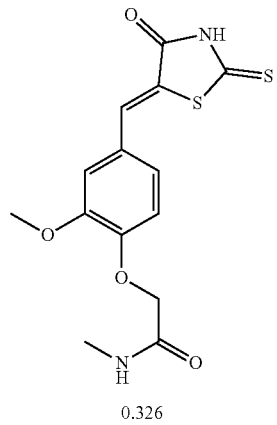
0.326
NADi-181
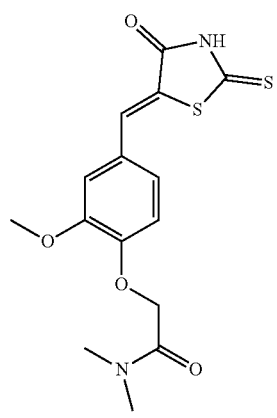 [SMILES: COc1cc(/C=C2\SC(=S)NC2=O)ccc1OCC(C)=O]
0.35
NADi-182
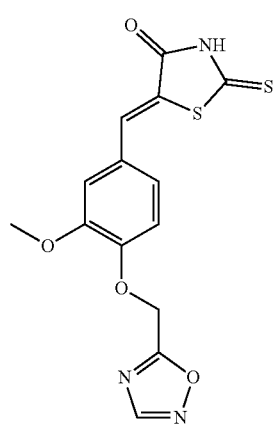 [SMILES: COc1cc(/C=C2\SC(=S)NC2=O)ccc1OCc1ncno1]
TABLE 1-continued
Identification No.
Structure
Screen Results at 8 μM
NADi-183
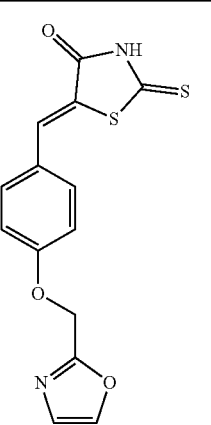
NADi-184
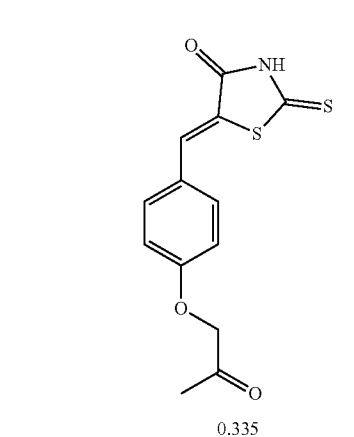 [SMILES: CC(=O)COc1ccc(/C=C2\SC(=S)NC2=O)cc1]
0.335
NADi-185
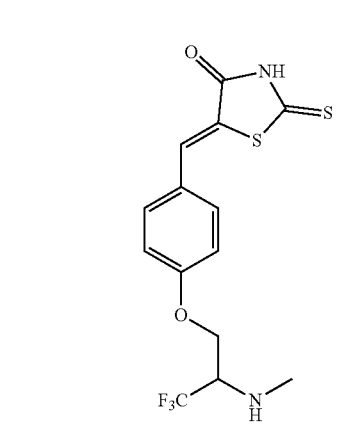 [SMILES: CNC(COc1ccc(/C=C2\SC(=S)NC2=O)cc1)C(F)(F)F]

TABLE 1-continued
| Identification No. Structure Screen Results at 8 μM |
|---|
| NADi-186 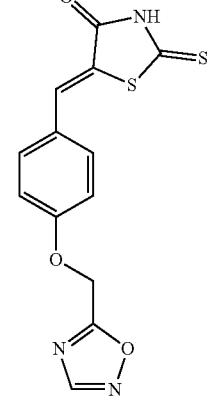 0.431 |
| NADi-187 0.379 |
| NADi-188 0.427 |
| NADi-189 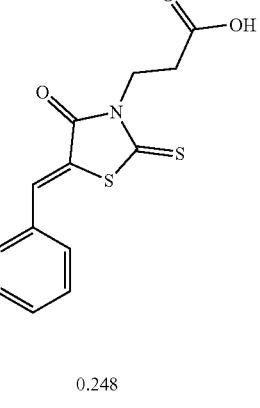 |
| NADi-190 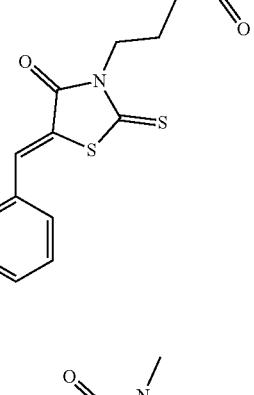 0.248 |
| NADi-191 |
| NADi-192 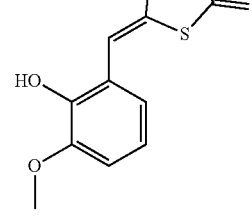 0.365 |

TABLE 1-continued
| Identification No. Structure Screen Results at 8 μM |
|---|
| NADi-193 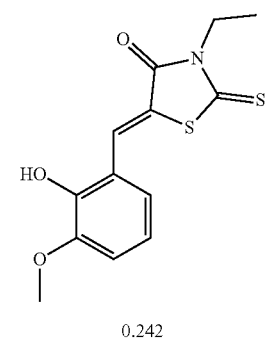 [SMILES: CCN1C(=O)/C(=C/c2cccc(OC)c2O)SC1=S] 0.242 |
| NADi-194 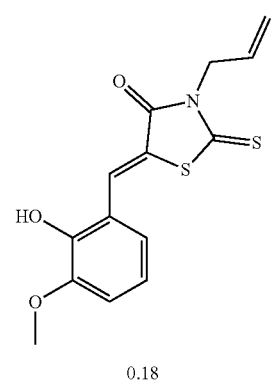 [SMILES: C=CCN1C(=O)/C(=C/c2cccc(OC)c2O)SC1=S] 0.18 |
| NADi-196 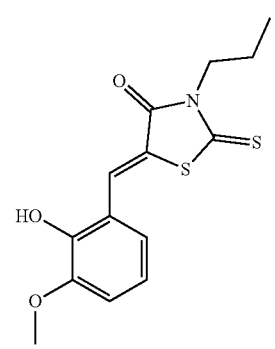 [SMILES: CCCN1C(=O)/C(=C/c2cccc(OC)c2O)SC1=S] 0.256 |
TABLE 1-continued
| Identification No. Structure Screen Results at 8 μM |
|---|
| NADi-197 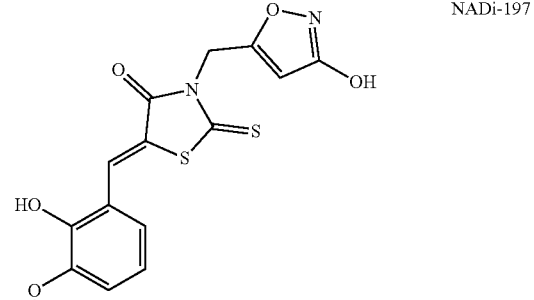 |
| NADi-198 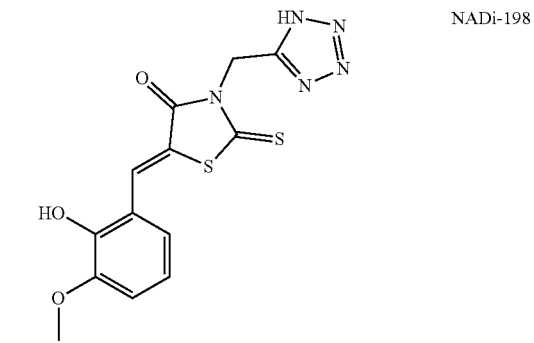 |
| NADi-199 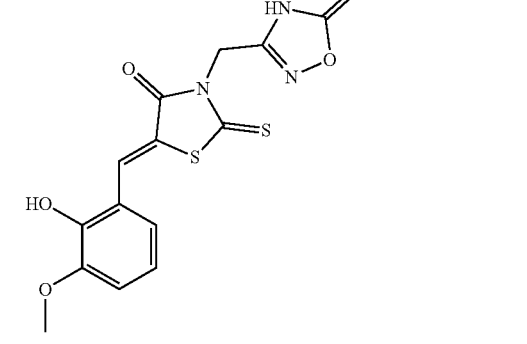 |
| NADi-200 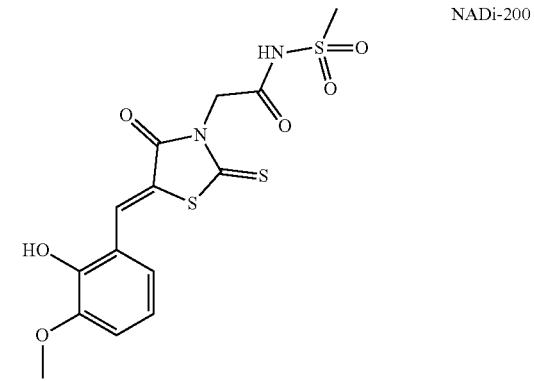 |

TABLE 1-continued
Identification No.
Structure
Screen Results at 8 μM
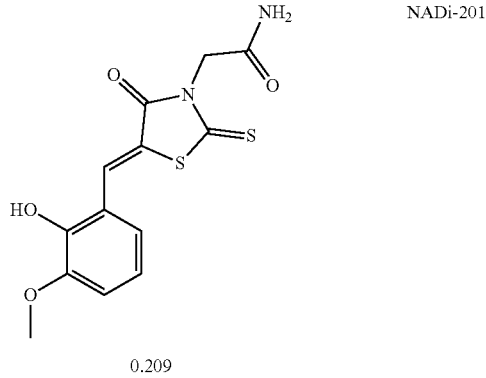
NADi-201
0.209
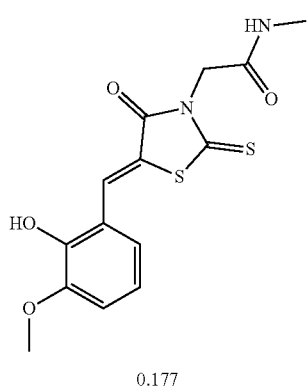 [SMILES: CNC(=O)CN1C(=O)/C(=C/c2cccc(OC)c2O)SC1=S]
NADi-202
0.177
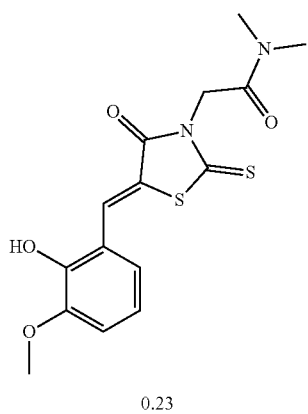 [SMILES: COc1cccc(/C=C2\SC(=S)N(CC(=O)N(C)C)C2=O)c1O]
NADi-203
0.23
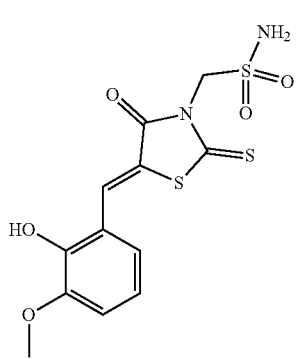 [SMILES: COc1cccc(/C=C2\SC(=S)N(CS(N)(=O)=O)C2=O)c1O]
NADi-204
TABLE 1-continued
Identification No.
Structure
Screen Results at 8 μM
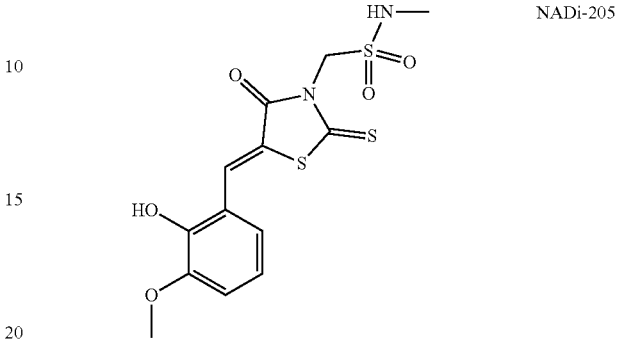
NADi-205
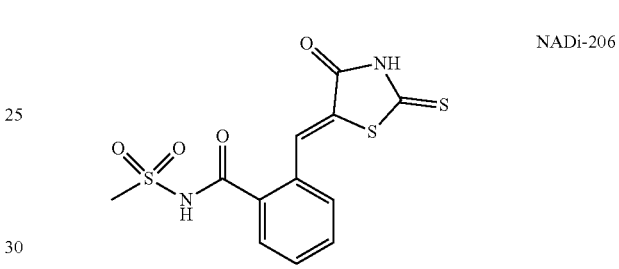
NADi-206
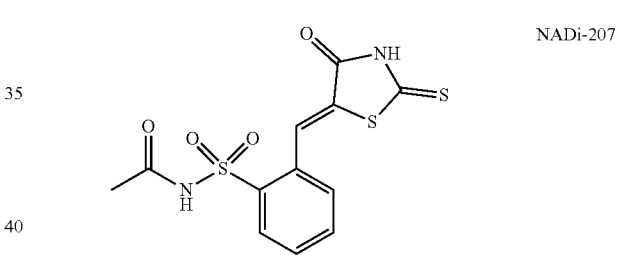
NADi-207
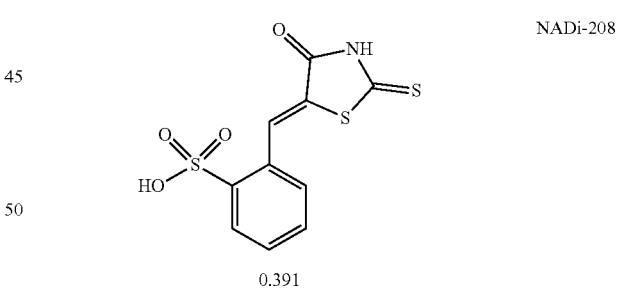
NADi-208
0.391
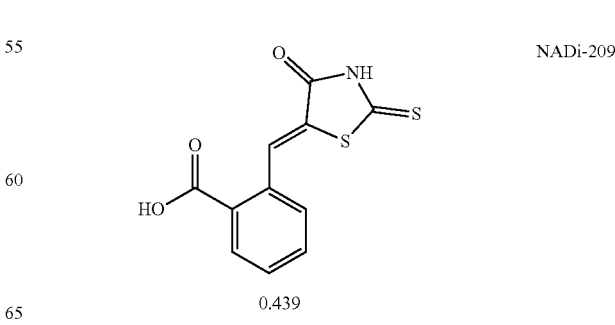
NADi-209
0.439

TABLE 1-continued
Identification No.
Structure
Screen Results at 8 μM
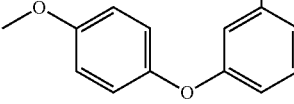
NADi-210
NADi-217
NADi-220
NADi-221
NADi-225
NADi-227
TABLE 1-continued
Identification No.
Structure
Screen Results at 8 μM
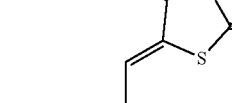
NADi-229
NADi-230
NADi-231
NADi-232
NADi-235

TABLE 1-continued

Identification No.
Structure
Screen Results at 8 μM

NADi-236

NADi-237

NADi-238

NADi-239

TABLE 1-continued

Identification No.
Structure
Screen Results at 8 μM

NADi-241

In some embodiments, the inhibitor of the Notch transcriptional activation complex is selected from a compound listed in Table 2.

TABLE 2

Identification No.
Structure
Screen Results at 8 μM

NADi-111

NADi-112

NADi-114

TABLE 2-continued

Identification No.
Structure
Screen Results at 8 μM

NADi-115

NADi-116

NADi-171

NADi-172

NADi-173

NADi-174

NADi-175

NADi-211

NADi-212

NADi-213

0.431

TABLE 2-continued

Identification No.
Structure
Screen Results at 8 μM

NADi-214

NADi-215

NADi-216

NADi-218

NADi-219

NADi-222

NADi-223

NADi-224

NADi-226

NADi-228

Also provided herein are novel inhibitors of the Notch transcriptional activation complex. In some embodiments, the novel inhibitors are selected from a compound listed in Table 3.

TABLE 3
| Identification No. Structure Screen Results at 8 µM |
|---|
| NADi-094 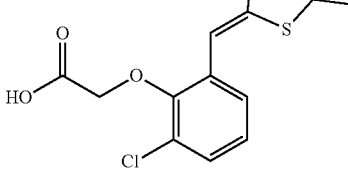 0.372 |
| NADi-095 0.297 |
| NADi-098 0.492 |
| NADi-117 0.253 |
TABLE 3-continued
| Identification No. Structure Screen Results at 8 µM |
|---|
| NADi-140 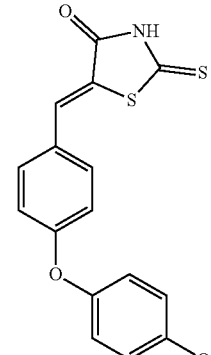 0.161 |
| NADi-158 0.324 |
| NADi-163 0.477 |
| NADi-170 0.437 |

TABLE 3-continued
Identification No.
Structure
Screen Results at 8 µM
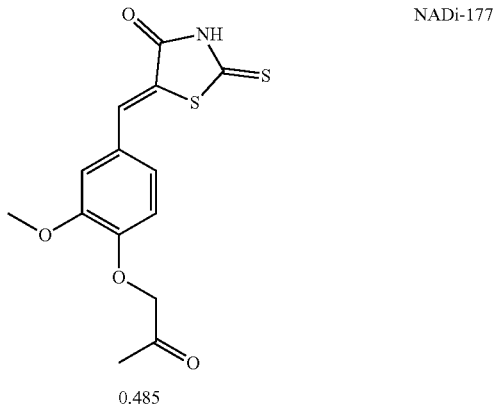
NADi-177
0.485
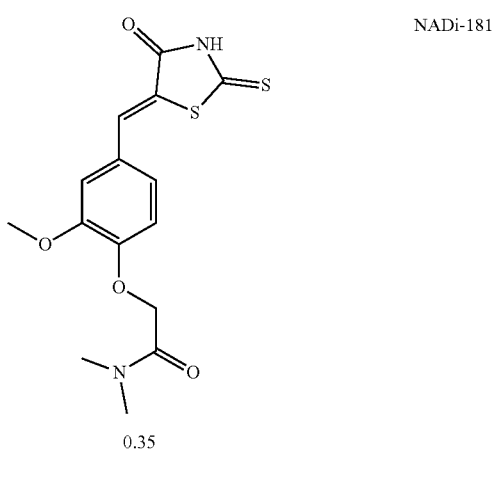
NADi-181
0.35
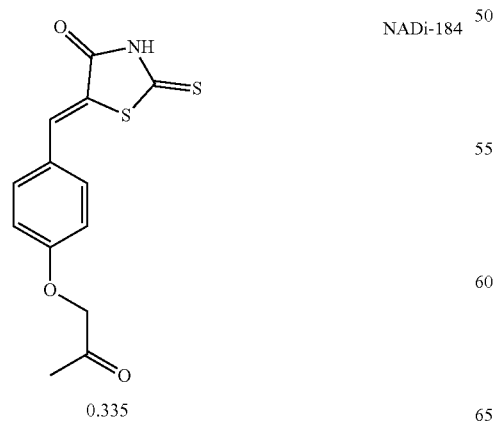
NADi-184
0.335
TABLE 3-continued
Identification No.
Structure
Screen Results at 8 µM
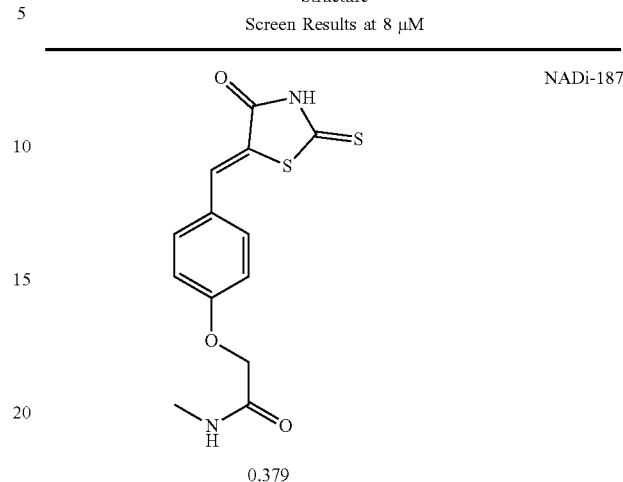
NADi-187
0.379
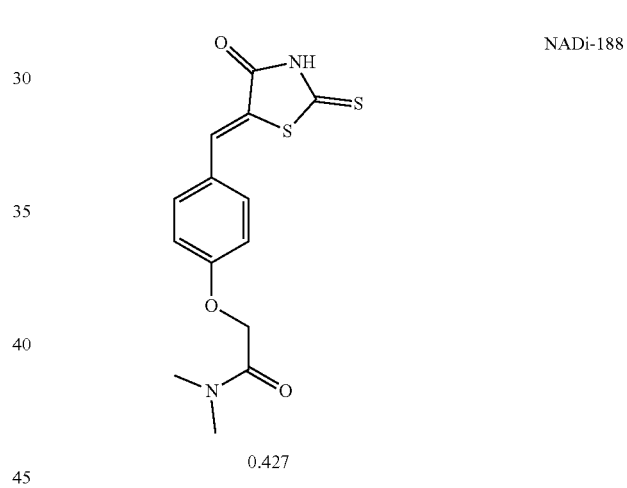
NADi-188
0.427
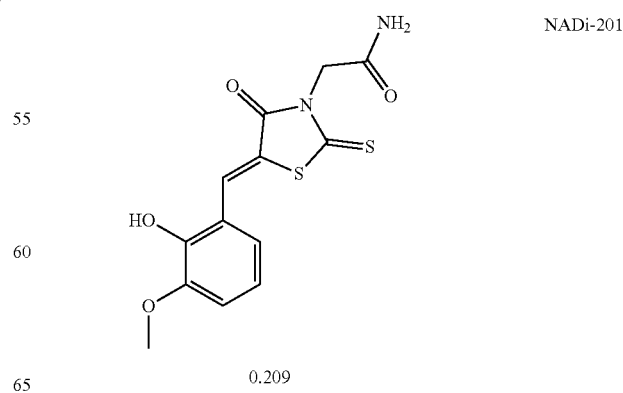
NADi-201
0.209

TABLE 3-continued

Identification No.
Structure
Screen Results at 8 μM

NADi-202

0.177

NADi-203

0.23

NADi-213

0.431

TABLE 4

Identification No.
Structure

NADi-090

NADi-091

NADi-093

NADi-096

NADi-097

In some cases, the inhibitors are selected from a compound listed in Table 4.

TABLE 4-continued
| Identification No. Structure |
|---|
| NADi-108 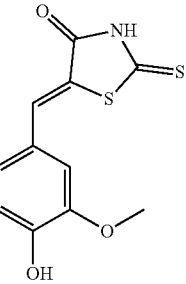 |
| NADi-109 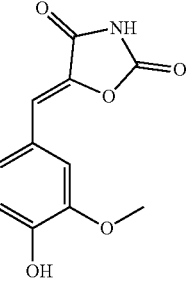 |
| NADi-110 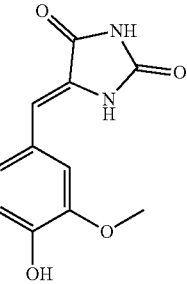 |
| NADi-111 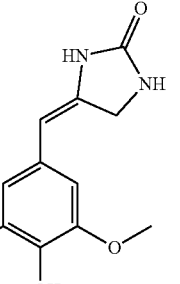 |
| NADi-112 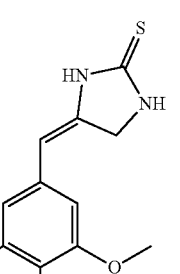 |
TABLE 4-continued
| Identification No. Structure |
|---|
| NADi-114  |
| NADi-115 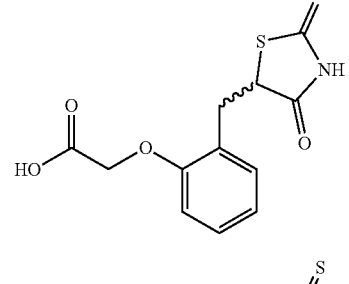 |
| NADi-116 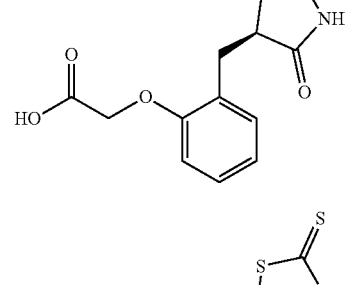 |
| NADi-118 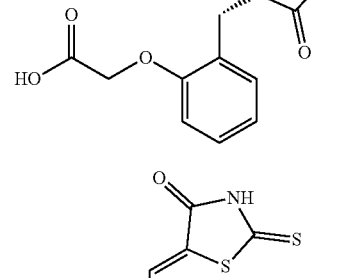 |
| NADi-120 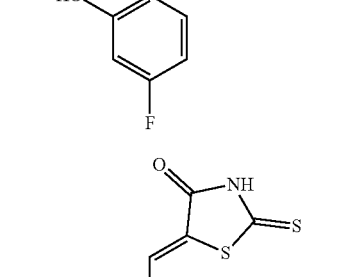 |
| NADi-124 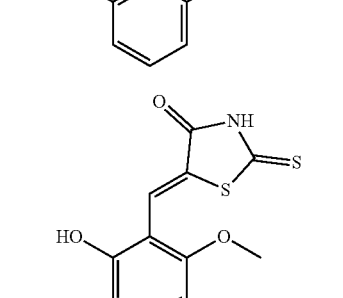 |

TABLE 4-continued

| Identification No. Structure | |
|---|---|
| (5-(2-fluoro-3-hydroxybenzylidene)-2-thioxothiazolidin-4-one) | NADi-125 |
| (5-(3-hydroxy-4-fluorobenzylidene)-2-thioxothiazolidin-4-one) | NADi-126 |
| (5-(3-fluoro-5-hydroxybenzylidene)-2-thioxothiazolidin-4-one) | NADi-127 |
| (5-(2-fluoro-5-hydroxybenzylidene)-2-thioxothiazolidin-4-one) | NADi-128 |
| (5-(2-methoxy-3-hydroxybenzylidene)-2-thioxothiazolidin-4-one) | NADi-129 |
| (5-(3-hydroxy-5-methoxybenzylidene)-2-thioxothiazolidin-4-one) | NADi-131 |
| (5-(2-methoxy-5-hydroxybenzylidene)-2-thioxothiazolidin-4-one) | NADi-132 |
| (5-(2-(tetrazol-5-yl)benzylidene)-2-thioxothiazolidin-4-one) | NADi-133 |
| (5-(3-(tetrazol-5-yl)benzylidene)-2-thioxothiazolidin-4-one) | NADi-134 |
| (5-(4-(tetrazol-5-yl)benzylidene)-2-thioxothiazolidin-4-one) | NADi-135 |
| (5-(3-chloro-2-hydroxybenzylidene)-2-thioxothiazolidin-4-one) | NADi-136 |

TABLE 4-continued
| Identification No. Structure | | Identification No. Structure | |
|---|---|---|---|
| 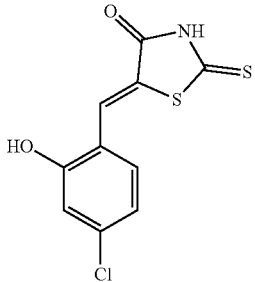 [SMILES: O=C1NC(=S)S/C1=C\c1ccc(Cl)cc1O] | NADi-137 | 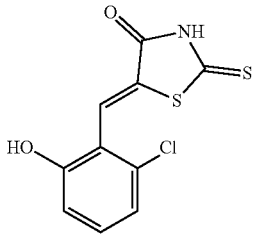 [SMILES: O=C1NC(=S)S/C1=C\c1c(O)cccc1Cl] | NADi-145 |
| 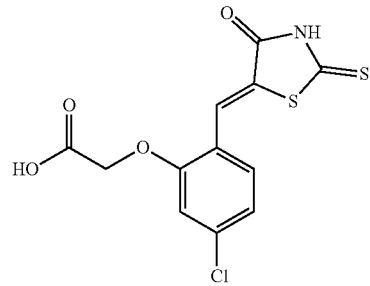 [SMILES: O=C(O)COc1cc(Cl)ccc1/C=C1\SC(=S)NC1=O] | NADi-139 | 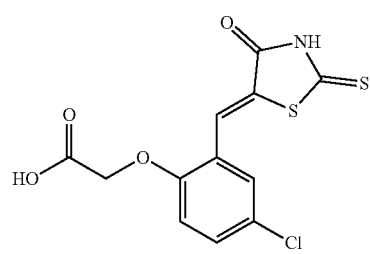 [SMILES: O=C(O)COc1ccc(Cl)cc1/C=C1\SC(=S)NC1=O] | NADi-148 |
| 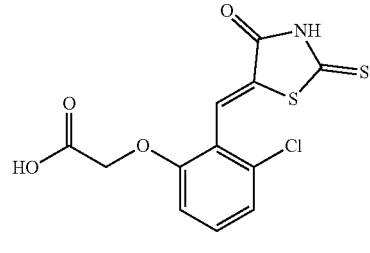 [SMILES: O=C(O)COc1cccc(Cl)c1/C=C1\SC(=S)NC1=O] | NADi-141 | 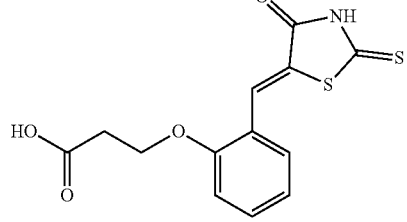 | NADi-149 |
| 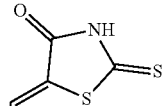 | NADi-142 | 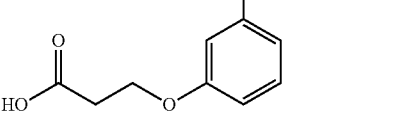 | NADi-150 |
| 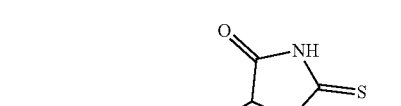 | NADi-143 | 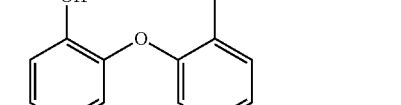 | NADi-152 |
| 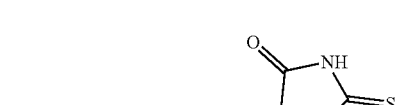 | NADi-144 | 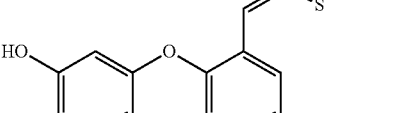 | NADi-153 |

TABLE 4-continued
Identification No.
Structure
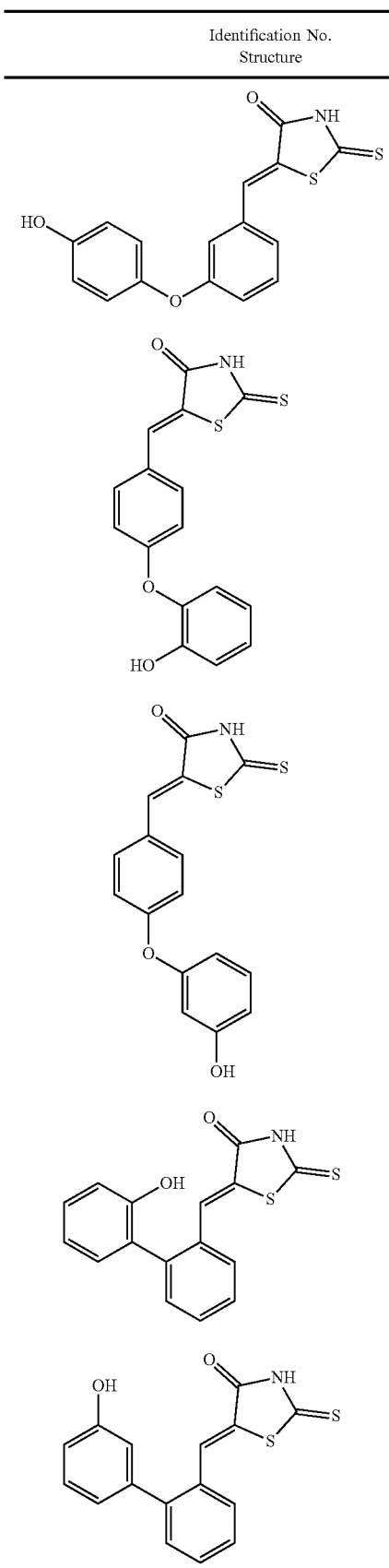
NADi-154
NADi-156
NADi-157
NADi-160
NADi-161
TABLE 4-continued
Identification No.
Structure
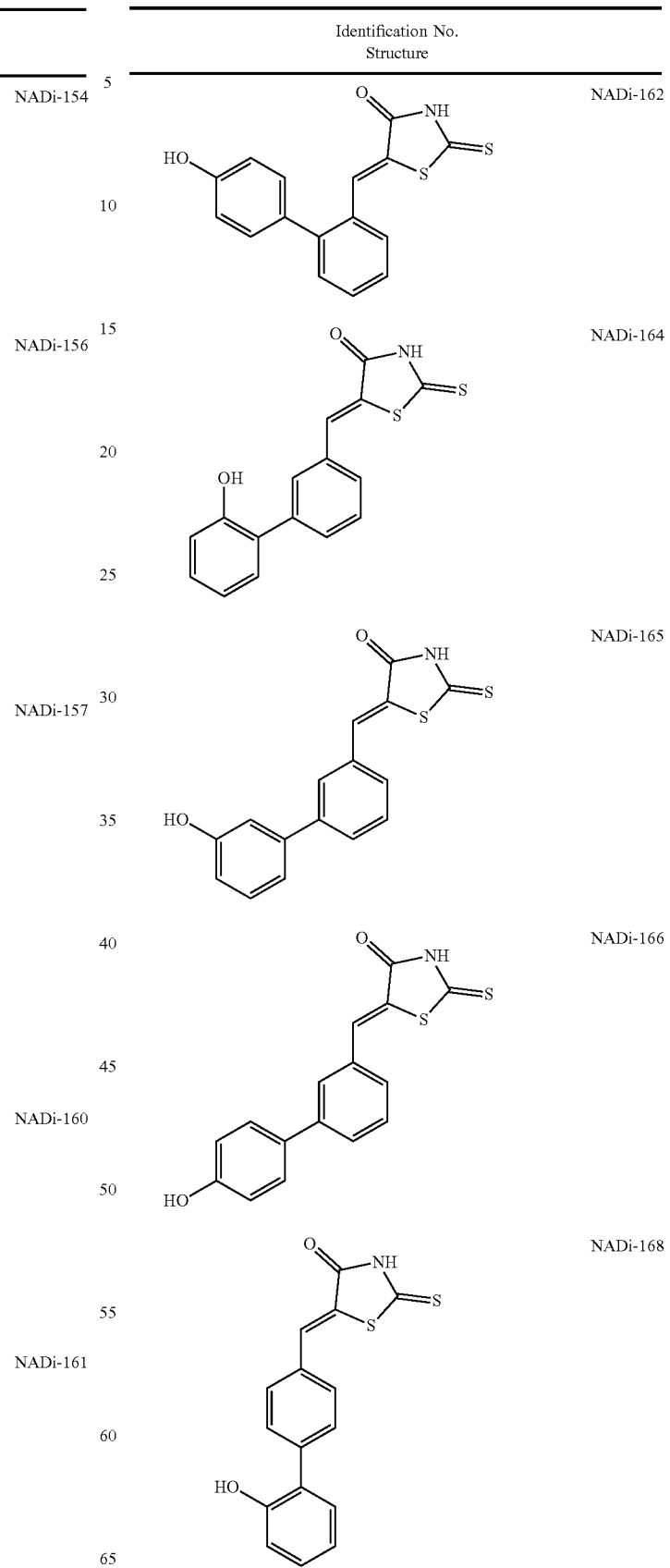
NADi-162
NADi-164
NADi-165
NADi-166
NADi-168

TABLE 4-continued
| Identification No. Structure |
|---|
| NADi-169 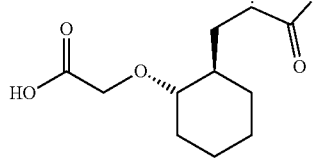 |
| NADi-171 |
| NADi-172 |
| NADi-173 |
| NADi-174 |
TABLE 4-continued
| Identification No. Structure |
|---|
| NADi-175 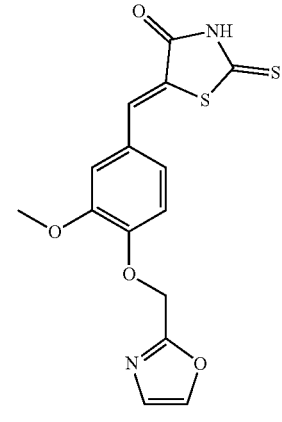 [SMILES: COc1cc(/C=C2\SC(=S)NC2=O)ccc1OCc1ncco1] |
| NADi-176 |
| NADi-178 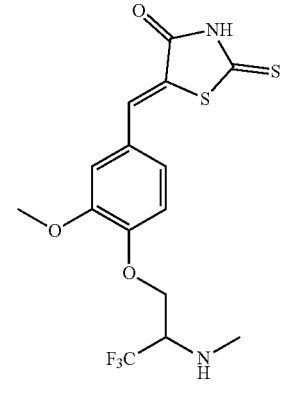 [SMILES: CNC(COc1ccc(/C=C2\SC(=S)NC2=O)cc1OC)C(F)(F)F] |
| NADi-182 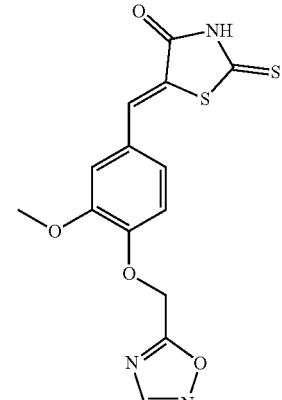 |

TABLE 4-continued
| Identification No. Structure | |
|---|---|
| 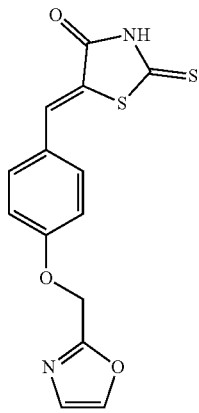 [SMILES: O=C1NC(=S)S/C1=C\c1ccc(OCc2ncco2)cc1] | NADi-183 |
| 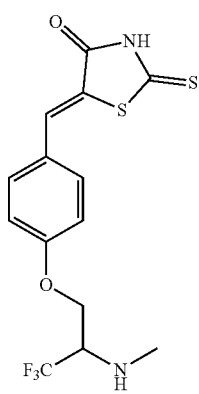 [SMILES: CNC(COc1ccc(/C=C2\SC(=S)NC2=O)cc1)C(F)(F)F] | NADi-185 |
| 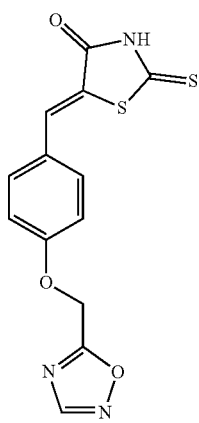 [SMILES: O=C1NC(=S)S/C1=C\c1ccc(OCc2ncno2)cc1] | NADi-189 |
TABLE 4-continued
| Identification No. Structure | |
|---|---|
| 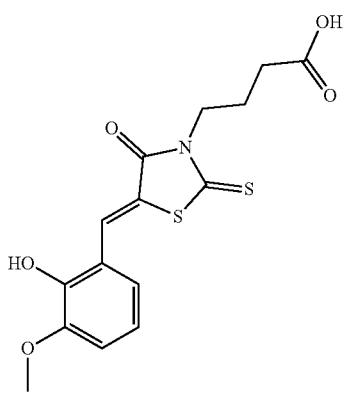 [SMILES: COc1cccc(/C=C2\SC(=S)N(CCCC(=O)O)C2=O)c1O] | NADi-191 |
| 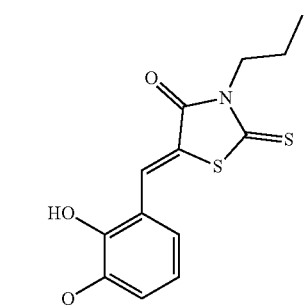 | NADi-195 |
| 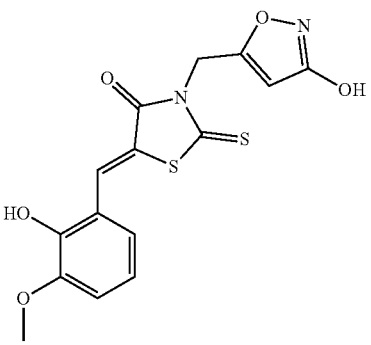 [SMILES: COc1cccc(/C=C2\SC(=S)N(Cc3cc(O)no3)C2=O)c1O] | NADi-197 |
| 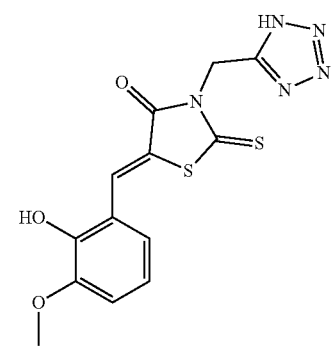 [SMILES: COc1cccc(/C=C2\SC(=S)N(Cc3nnn[nH]3)C2=O)c1O] | NADi-198 |

TABLE 4-continued
| Identification No. Structure | |
|---|---|
| 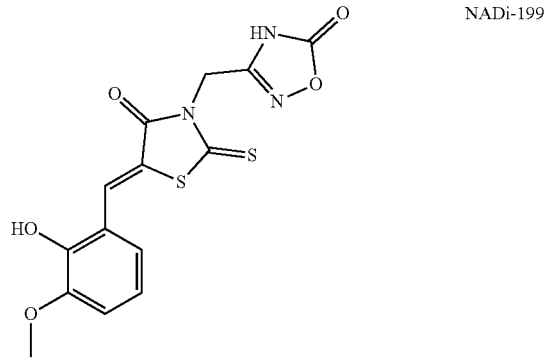 | NADi-199 |
| 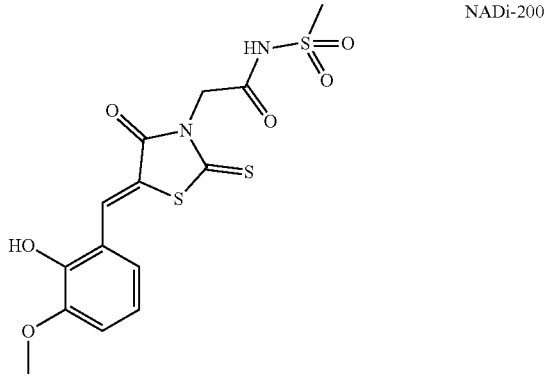 | NADi-200 |
| 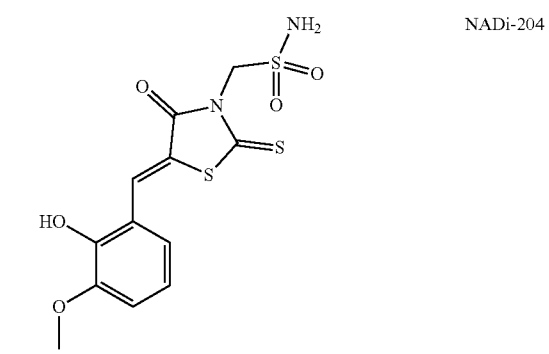 | NADi-204 |
| 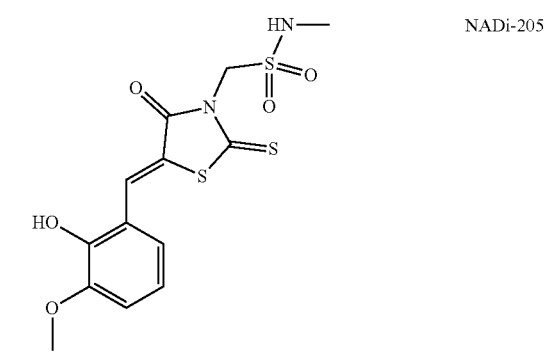 | NADi-205 |
TABLE 4-continued
| Identification No. Structure | |
|---|---|
| 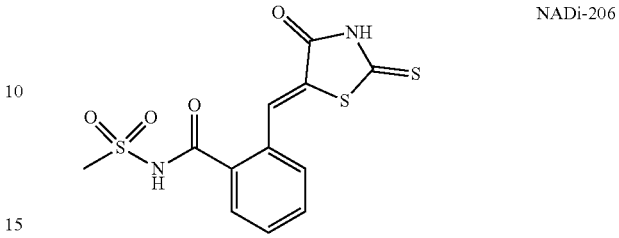 | NADi-206 |

TABLE 4-continued
| Identification No. Structure | |
|---|---|
| 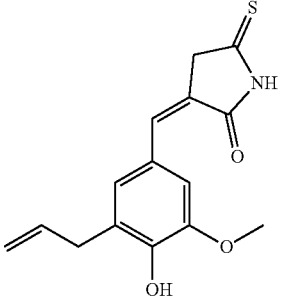 [SMILES: C=CCc1cc(/C=C2/CC(=S)NC2=O)cc(OC)c1O] | NADi-214 |
| 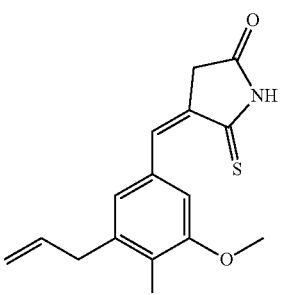 | NADi-215 |
| 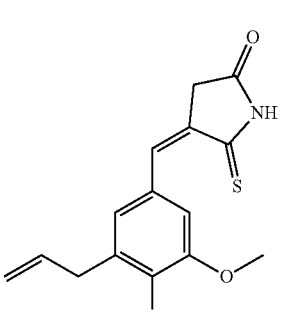 | NADi-216 |
| 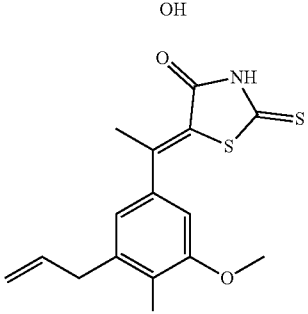 | NADi-217 |
| 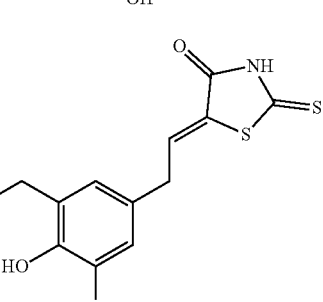 | NADi-218 |
| 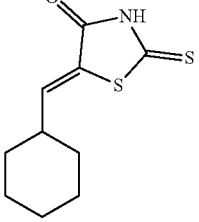 | NADi-219 |
| 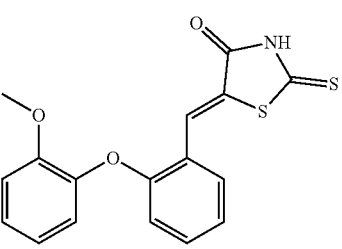 [SMILES: COc1ccccc1Oc1ccccc1/C=C1\SC(=S)NC1=O] | NADi-220 |
| 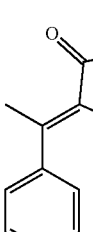 | NADi-221 |
| 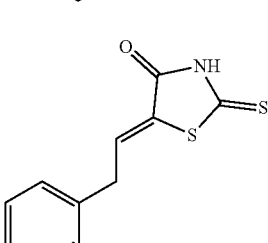 | NADi-222 |
| 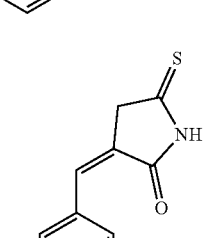 | NADi-223 |
|  | NADi-224 |

TABLE 4-continued

| Identification No. Structure |
|---|
| NADi-225 |
| NADi-226 |
| NADi-227 |
| NADi-228 |
| NADi-229 |
| NADi-230 |
| NADi-231 |
| NADi-232 |
| NADi-235 |
| NADi-236 |

TABLE 4-continued

| Identification No. Structure | |
|---|---|
| (structure) | NADi-237 |
| (structure) | NADi-238 |
| (structure) | NADi-239 |
| (structure) | NADi-241 |

In some embodiments, the compounds in Table 1, Table 2, Table 3, and Table 4 are in the Z configuration. In some embodiments, the compounds in Table 1, Table 2, Table 3, and Table 4 are in the E configuration.

Synthesis of the NTC Inhibitors

The inhibitors of the disclosure can be synthesized by any method known to one skilled in the art. For example, a desired appropriate benzaldehyde (e.g., when $R^2$ is H) and an appropriate heterocycloakyl group can undergo a condensation reaction under acidic or basic conditions, at an elevated temperature, to form the desired inhibitor, as shown in the scheme below.

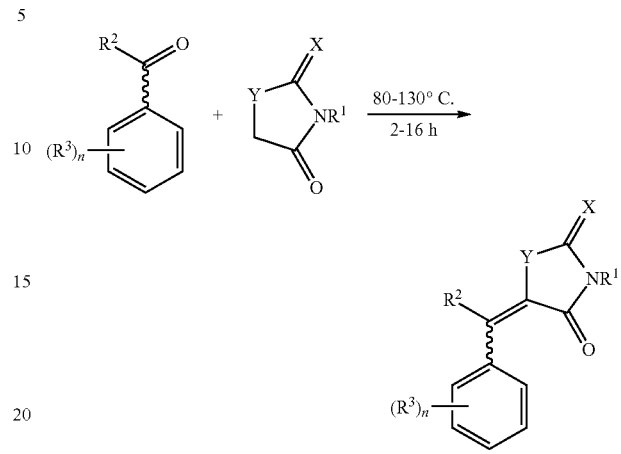

Additional synthetic procedures for preparing the inhibitors disclosed herein can be found in the Examples section.

Methods of Using the NTC Inhibitors

The inhibitors of the disclosure can inhibit the Notch transcriptional activation complex ("NTC") by disrupting recruitment of MAML1 to the complex, which is useful in preventing or treating diseases associated with deregulation of the Notch transcriptional activation complex.

As previously described herein, the Notch pathway is restricted to small populations of progenitor and stem cells of regenerating tissues, such as the colon and brain. However, in many human cancers, the Notch pathway becomes reactivated, and this deregulation of the Notch pathway underlies many aspects of cancer physiology, depending on cell type and context.

Therefore, one aspect of the disclosure relates to a method of inhibiting the Notch transcriptional activation complex in a cell, comprising contacting the cell with a compound selected from the group consisting of (or a pharmaceutically acceptable salt thereof): a compound of Formula (I), a compound of Formula (Ia), a compound of Formula (Ib), a compound listed in Table 1, a compound listed in Table 2, and a mixture thereof, in an amount effective to inhibit the NTC. In particular, provided herein is a method of inhibiting MAML1 recruitment to the Notch transcriptional activation complex in a cell by contacting the cell with a compound selected from the group consisting of (or a pharmaceutically acceptable salt thereof): a compound of Formula (I), a compound of Formula (Ia), a compound of Formula (Ib), a compound listed in Table 1, a compound listed in Table 2, and a mixture thereof, in an amount effective to inhibit the NTC.

The inhibitors disclosed herein can inhibit the NTC in a cell by contacting the cell in vitro or in vivo. In some embodiments, the contacting occurs in vitro. In other embodiments, the contacting occurs in vivo. The inhibitors can contact the NTC in vivo by administering the inhibitor to a subject or patient in need of regulation of the NTC. Put another way, in various embodiments, the invention includes administering one or more inhibitors of the disclosure to a subject or patient, such as a human, in need thereof. In some of these embodiments, the patient suffers from a disease associated with deregulation of the Notch transcriptional activation complex (e.g., Tetralogy of Fallot ("TOF"), Alagille syndrome, or cancer).

Another aspect of the disclosure relates to a method of treating a disease associated with deregulation of the Notch transcriptional activation complex in a patient, comprising administering to the patient a therapeutically effective amount of a compound selected from the group consisting of (or a pharmaceutically acceptable salt thereof): a compound of Formula (I), a compound of Formula (Ia), a compound of Formula (Ib), a compound listed in Table 1, a compound listed in Table 2, and a mixture thereof. In some embodiments, the disease is selected from Tetralogy of Fallot ("TOF"), or Alagille syndrome. In some cases, the disease is cancer. In various embodiments, the cancer is selected from the group consisting of T-cell acute lymphoblastic leukemia ("T-ALL"), B-cell acute lymphoblastic leukemia ("B-ALL"), breast cancer, medulloblastoma, colorectal cancer, non-small cell lung carcinoma ("NSCLC"), melanoma, cerebral autosomal-dominant ateriopathy with sub-cortical infarcts and leukoencephalophathy ("CADASIL"), chronic lymphocytic leukemia ("CLL"), hepatocellular carcinoma ("HCC"), myelomonocytic leukemia ("CMML"), pancreatic ductal adenocarcinoma ("PDAC"), multiple sclerosis ("MS"), head and neck squamous cell carcinoma ("HN-SCC"), renal cell adenocarcinoma, fibrosarcoma, and combinations thereof.

Use of an inhibitor disclosed herein, such as a compound selected from the group consisting (or a pharmaceutically acceptable salt thereof): a compound of Formula (I), a compound of Formula (Ia), a compound of Formula (Ib), a compound listed in Table 1, a compound listed in Table 2, and a mixture thereof, to treat a condition resulting from deregulation of the Notch transcriptional activation complex in a patient, as well as use of the inhibitor in the preparation of a medicament for treating the condition, also are contemplated.

Further guidance of using the inhibitors disclosed herein for inhibiting the NTC can be found in the Examples section, below.

Mechanistic Effects of the NTC Inhibitors

Mechanistic effects of the inhibitors disclosed herein on the NTC are described in detail below.

In Vitro Binding Assay

Figure 1B:
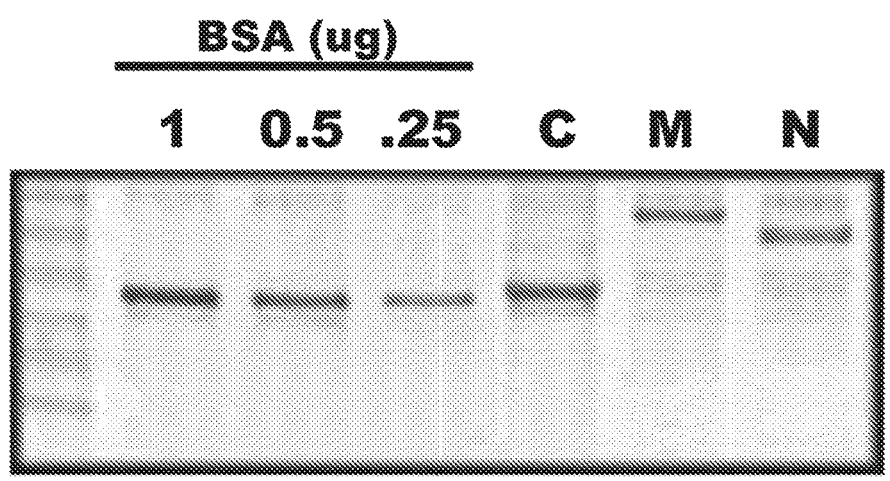
FIG. 1B depicts a stain of SDS-PAGE showing the baculovirus-expressed purified proteins (C=CSL; N=Notch 1; M=MAML1; BSA standards) used in the assay (LOWER). A signal is produced when beads are brought in close proximity to each other. This was achieved by using a biotinylated oligonucleotide and an antibody against a specific member of the NTC. The donor and receptor beads are conjugated to streptavidin and protein A, respectively.

An in vitro assay was developed to monitor the assembly of the Notch transcriptional complex ("NTC") on DNA. The NTC, which includes the Notch, Mastermind ("MAML1"), and CSL proteins, binds to a specific DNA sequence in a CSL-dependent manner. For the assay, baculovirus produced CSL, Notch, and MAML1 were mixed together with a biotinylated DNA oligomer containing the CSL target sequence. Assembly of the NTC on DNA was then monitored with the proximity-based ALPHASCREEN (Perkin Elmer) using streptavidin and protein A beads (FIGS. 1A and 1B). A signal results when MAML1 is recruited to CSL bound DNA.

Figure 1C:
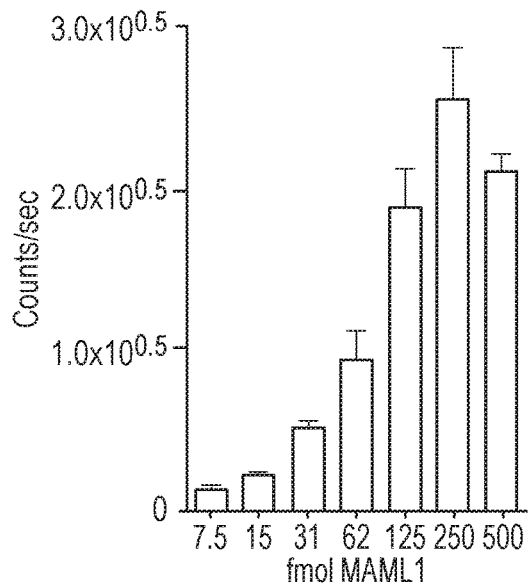
FIGS. 1C and 1D depict the titration of MAML1 (1C) and Notch1 (1D) in the NTC assay. Addition of either Notch1 or MAML1 leads to a dose dependent increase in signal, indicating the requirement of Notch in the association of MAML1 to the NTC.
Figure 1D:
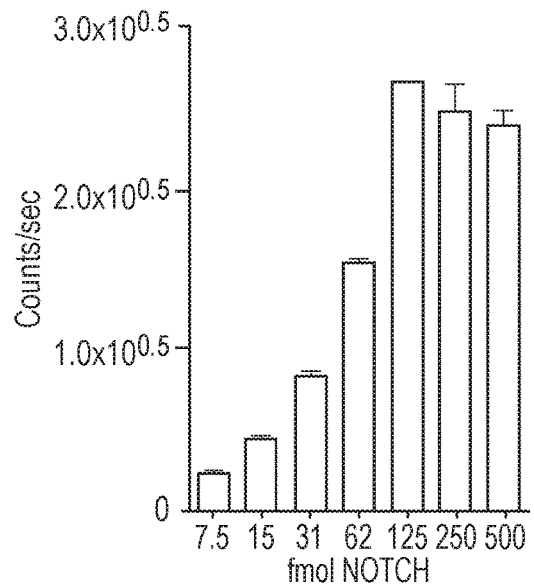
Figure 1E:
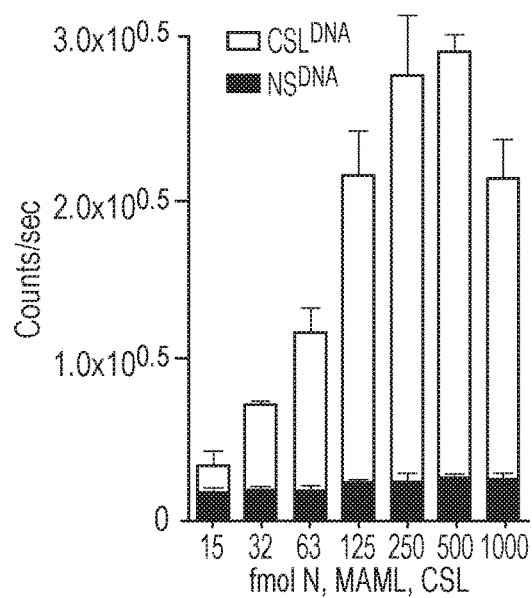
FIG. 1E illustrates that the CSL consensus sequence is required for assembly of complex on DNA. An increase of all NTC components leads to an increase in signal only when the reaction contains an oligonucleotide harboring the CSL consensus sequence.
Figure 1F:
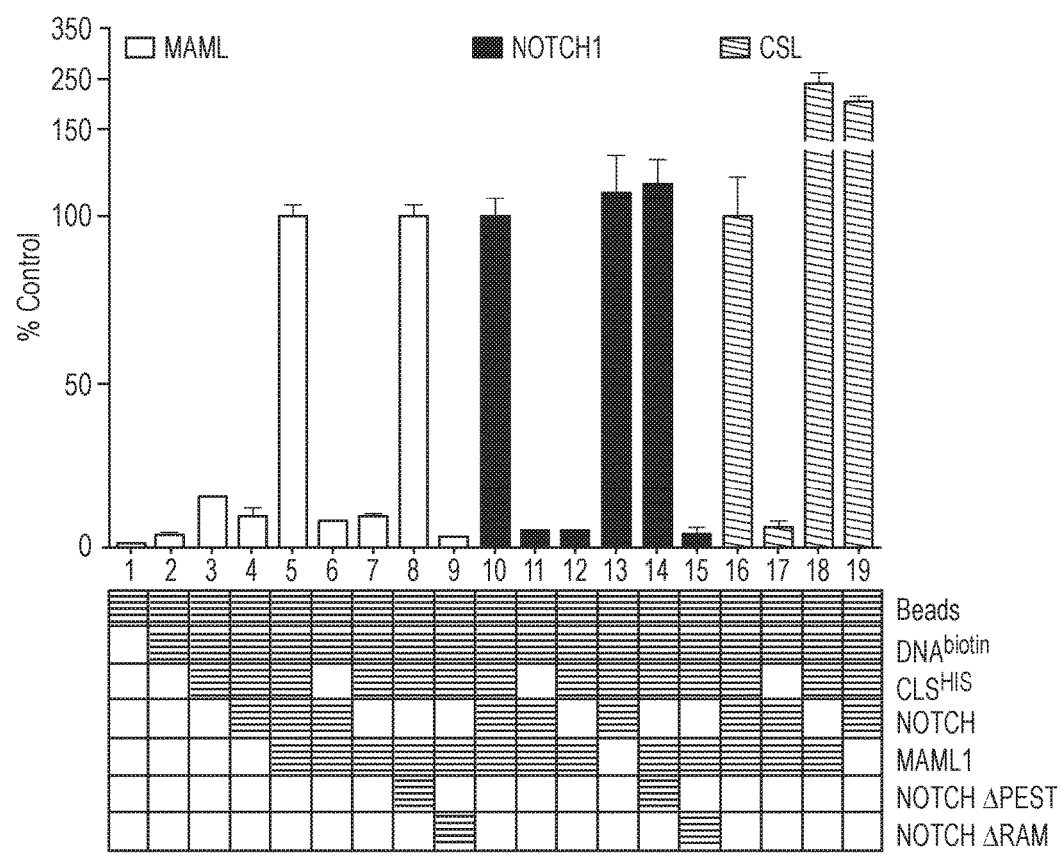
FIG. 1F illustrates that recruitment of MAML1 to the NTC requires the RAM domain of Notch1 (Lanes 1-9), binding of MAML1 requires all components of the NTC (Lanes 1-5), removal of either CSL (Lane 6) or Notch (Lane 7) causes a loss in MAML1 binding, and use of a Notch protein that lacks the pest domain has no effect on NTC assembly (lane 8). However, assembly of the complex depends on the Ram domain of Notch (Lane 9). Notch requires CSL to bind to DNA. Removal of CSL from the reaction prevents Notch from binding to DNA (Lane 11), while removal of MAML1 or use of Notch protein with a mutant pest domain does not alter its association to DNA (lanes 13 and 14). Deletion of the Ram domain causes a loss in Notch binding to DNA (lane 15). The binding of CSL to DNA is not lost if either MAML1 or Notch1 are omitted from the reaction (lanes 18 and 19).

To demonstrate that the signal observed was due to the recruitment of MAML1 to the complex, MAML1 was titrated against a fixed amount of the remaining reaction components. Increasing MAML1 in the reaction resulted in a dose-dependent increase in signal up to the stoichiometric equivalence point (250 fmol) (FIGS. 1C and 1D). Titrating Notch1 also displayed a dose response, indicating that recruitment of MAML1 depends on Notch1 binding to CSL. Furthermore, complex assembly is dependent on CSL binding to DNA, as an oligonucleotide that harbors a mutant CSL binding does not generate an appreciable signal (FIG. 1E). A signal is only observed when all components of the NTC are present in the reaction (FIG. 1F, lanes 1-5), and omission of either CSL or Notch from the reaction resulted in loss of signal (FIG. 1F, lanes 6-7), indicating that binding of MAML1 to the complex requires both CSL and Notch. CSL binding to DNA in the absence of the other NTC components (FIG. 1F, lanes 16-19) and Notch requires CSL, but not MAML1, to bind to DNA (FIG. 1F, lanes 11-13).

The requirement of specific protein domains was also tested. Deletion of the Notch RAM domain caused a loss in the binding of both Notch and MAML1 to the complex (FIG. 1F, lanes 9 and 15) whereas the deletion of the Notch PEST domain did not alter the assembly of the NTC (FIG. 1F, lanes 8 & 14). Therefore, the assay is measuring the assembly of a bona fide NTC, as the recruitment of MAML1 to the NTC is dependent on the high affinity binding of Notch to CSL through its RAM domain.

Disruption of MAML1 Recruitment to Chromatin.

Figure 2A:
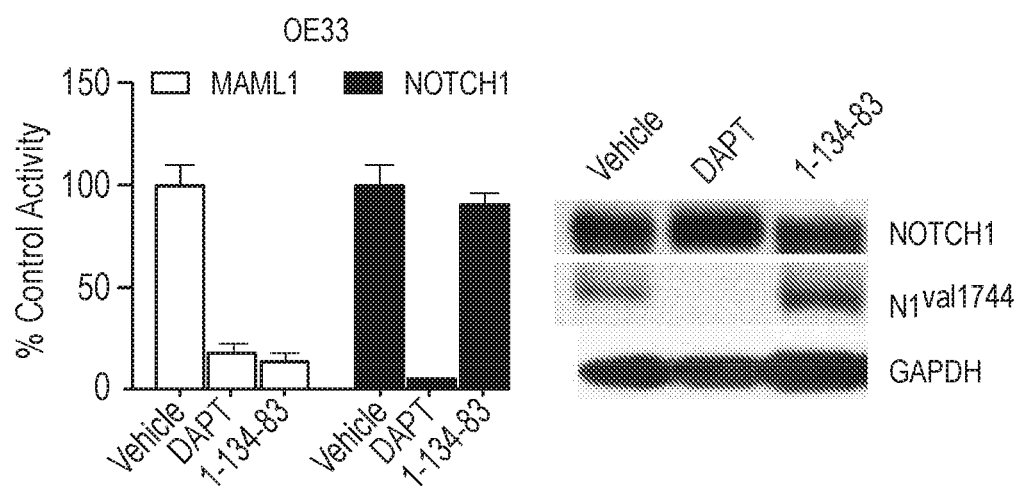
FIGS. 2A and 2B illustrate that treatment with DAPT caused a decrease in MAML1 and Notch1 recruitment to Hes1 promoter (left, green bars). The inhibition of γ-secretase caused a decrease in the NICD pool (right), and thus prevented the Notch-mediated association of MAML1 to promoter-bound CSL. Treatment with Inhibitor No. 1-134-83 caused a drop in MAML1 recruitment to Hes1 promoter (orange bars) without any change in the cleavage or recruitment of Notch1 to the Hes1 promoter.
Figure 2B:
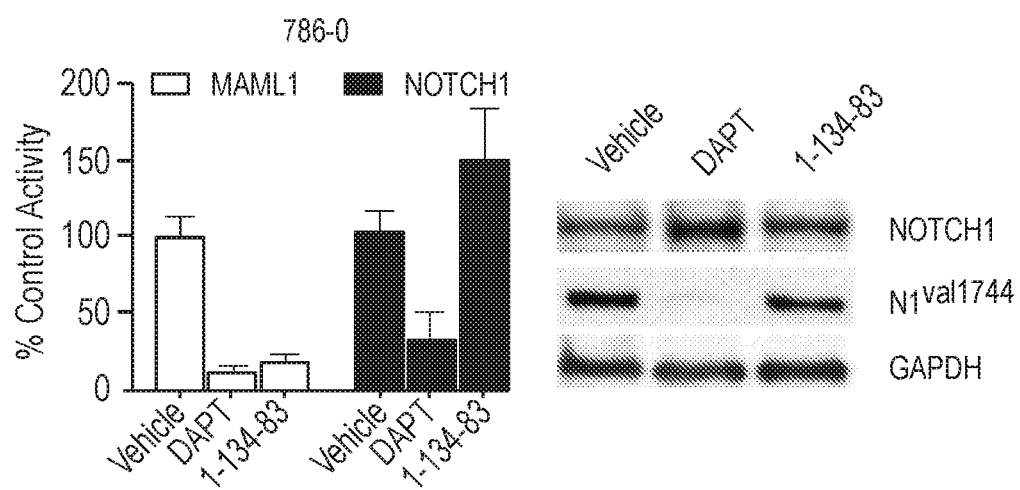

The effect of inhibitor treatment on the assembly of the NTC in cells was investigated. Notch dependent cell lines OE33 and 786-0 were treated with the γ-secretase inhibitor ("GSI") (N—[N-(3,5-difluorophenacetyl)-L-alanyl]-S-phenylglycine t-butyl ester ("DAPT") or Inhibitor No. 1-134-83, (previously disclosed herein). The occupancy of Notch and MAML1 on the HES1 locus was determined using a chromatin immunoprecipitation ("ChIP") assay. DAPT treatment decreased NOTCH1 and MAML1 occupancy on the HES1 promoter (FIGS. 2A and 2B), which was caused by a decrease in the NICD pool, due to the inhibition of presenilin-dependent γ-secretase (FIGS. 2A and 2B, right panel). Although treatment with Inhibitor No. 1-134-83 also decreased the occupancy of MAML1 on the HES1 promoter, inhibitor treatment did not affect the occupancy of NOTCH1 on HES1 promoter (FIGS. 2A and 2B). Western analysis of the lysates demonstrates that inhibitor treatment does not change the levels of NICD in cells (FIGS. 2A and 2B, right panel). Therefore, these data indicate that the inhibitors of the disclosure can disrupt the recruitment of MAML1 to chromatin, while the binding of NICD to CSL is unaffected.

Figure 2C:
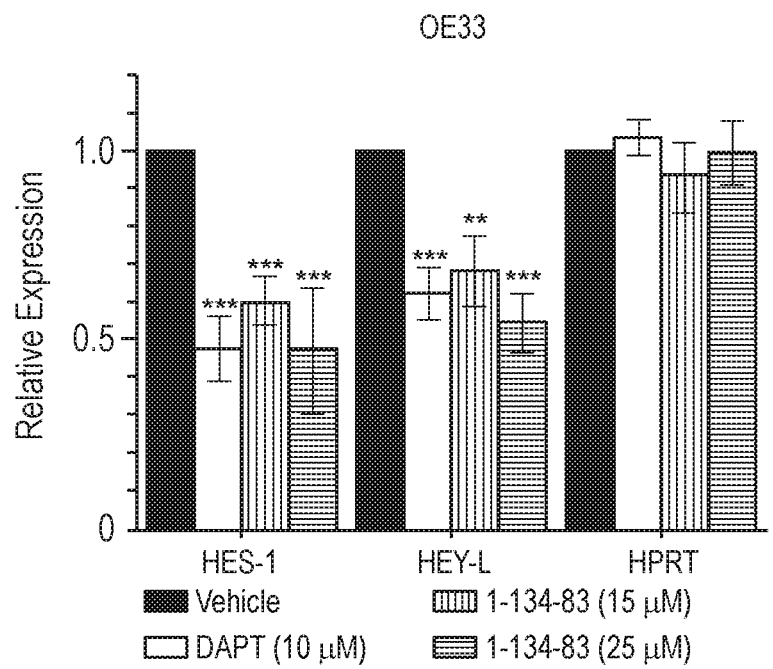
FIGS. 2C and 2D depict qPCR analysis of Notch target genes from treated cells. DAPT treatment caused a significant decrease in Notch target gene transcription. Similarly, Inhibitor No. 1-134-83 caused a dose-dependent decrease in Notch target get transcription. Transcription of control gene (HPRT) was not affected by either treatment.
Figure 2D:
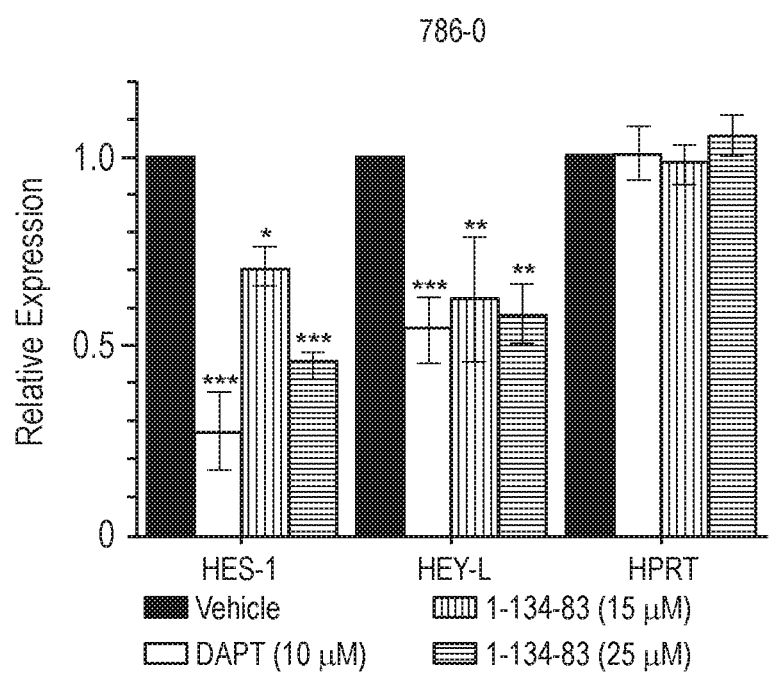
Figure 2E:
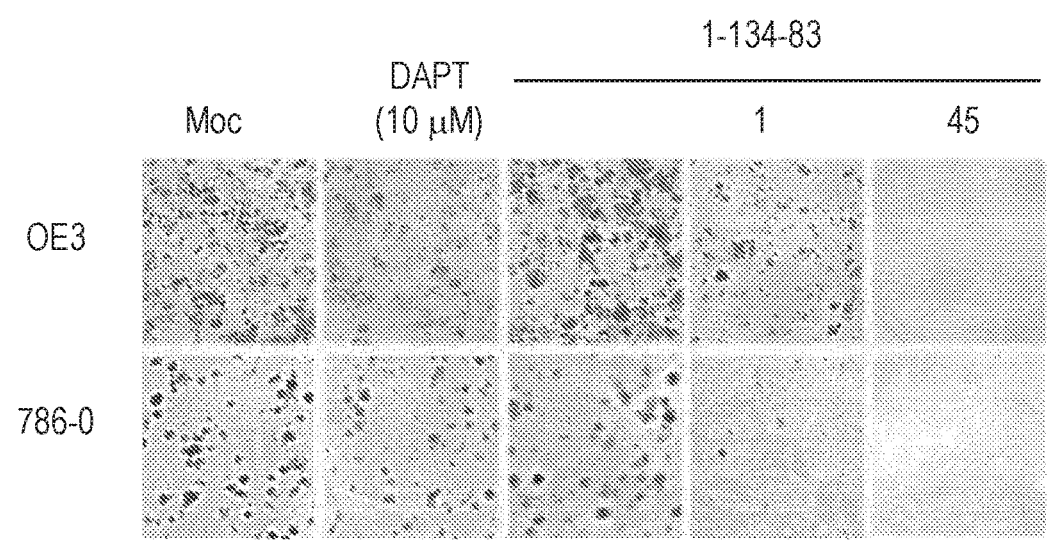
FIG. 2E depicts a colony formation assay of cells treated with DAPT or Inhibitor No. 1-134-83 for 7 days. DAPT inhibited the cell colony forming ability of cells. Inhibitor No. 1-134-83 exhibited a dose-dependent decrease in cell colony formation.

The effect of inhibitor treatment on Notch-target gene transcription also was investigated (FIGS. 2C and 2D). Cells that were treated with Inhibitor No. 1-134-83 displayed a dose-dependent decrease in Notch target gene transcription, similar to the control cells treated with DAPT. As proof of specificity, transcription of the housekeeping gene, HPRT, was unaltered in treated cells. To test the effects of Notch inhibition on proliferation, a colony formation assay was performed. Treatment of cells with Inhibitor No. 1-134-83 displayed a dose-dependent reduction in colony formation for both 786 and OE33 cell lines (FIG. 2E).

Figure 3C:
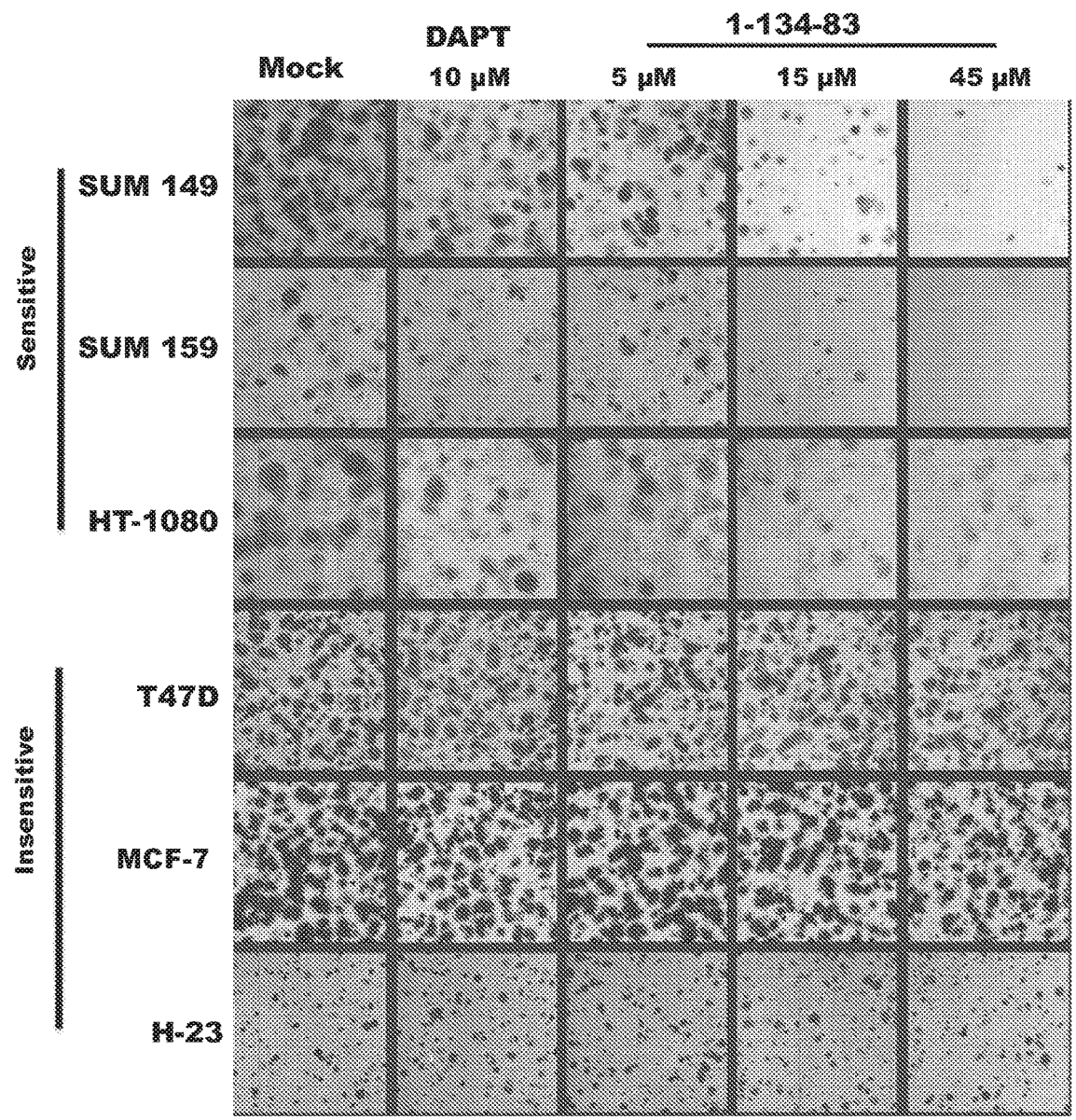
FIG. 3C illustrates that GSI and Inhibitor No. 1-134-83 inhibit colony formation in Notch dependent cell lines. Colony formation assay was performed by treating 150 cells/cm$^2$ with either DAPT or Inhibitor No. 1-134-83 for 7 days. Cells were stained with crystal violet. Sensitive cell lines showed a decrease in colony formation upon treatment with DAPT, and show a dose-dependent decrease in colony formation upon treatment with Inhibitor No. 1-134-83. Insensitive cell lines do not show changes in colony formation ability, even when treated with high doses of Inhibitor No. 1-134-83.
Figure 4A:
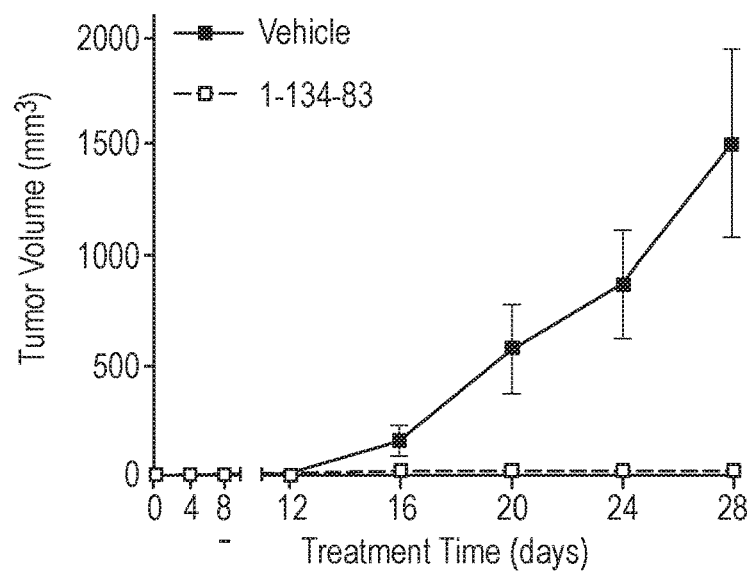
FIG. 4 illustrates that the treatment tumor xenografts with Inhibitor No. 1-134-83 reduces tumor growth and decreases transcription of Notch target genes. A PDX tumor from an esophageal adenocarcinoma was injected into mice and a treated with vehicle (blue line) or Inhibitor No. 1-134-83 (red line). Tumors treated with Inhibitor No. 1-134-83 showed a reduced volume at 16 weeks. By 20 weeks, the reduction in volume in treated tumors was statistically significant, with a decrease in tumor volume of three-fold by the experimental endpoint (FIGS. 4B, and 4C). Treated animals did not show any sign of stress or weight loss throughout the experiment (FIGS. 4F and 4G). qPCR analysis shows that Notch target gene transcription is reduced in treated tumors, while the transcription of the control gene (TBP2) is unaffected (FIGS. 4D and 4E). Transcript levels are plotted as the normalized value $\Delta C_t$. 1 Million OE19 cells were injected into the mouse flank and Inhibitor No. 1-134-83 treatment started 2 days thereafter. Treated tumors did not show any sign of growth (FIG. 4A).
Figure 4B:
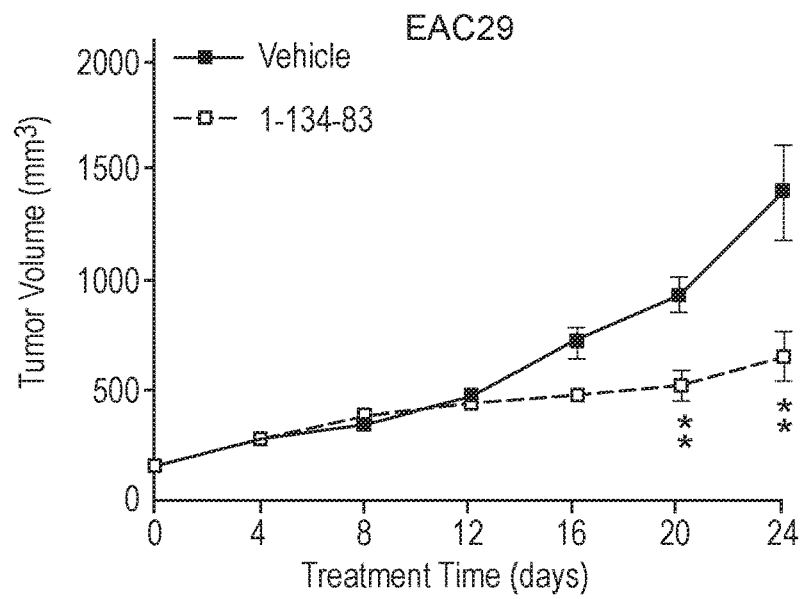
Figure 4B:
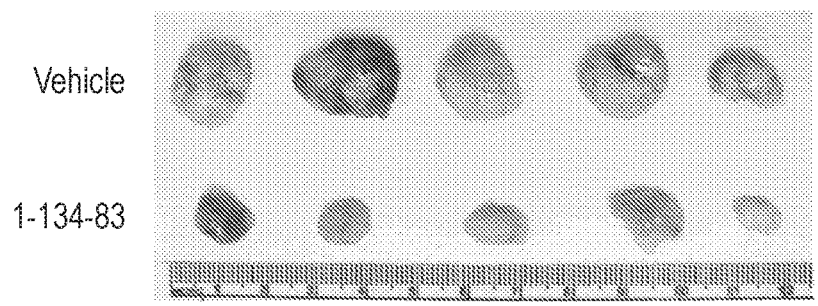
Figure 4C:
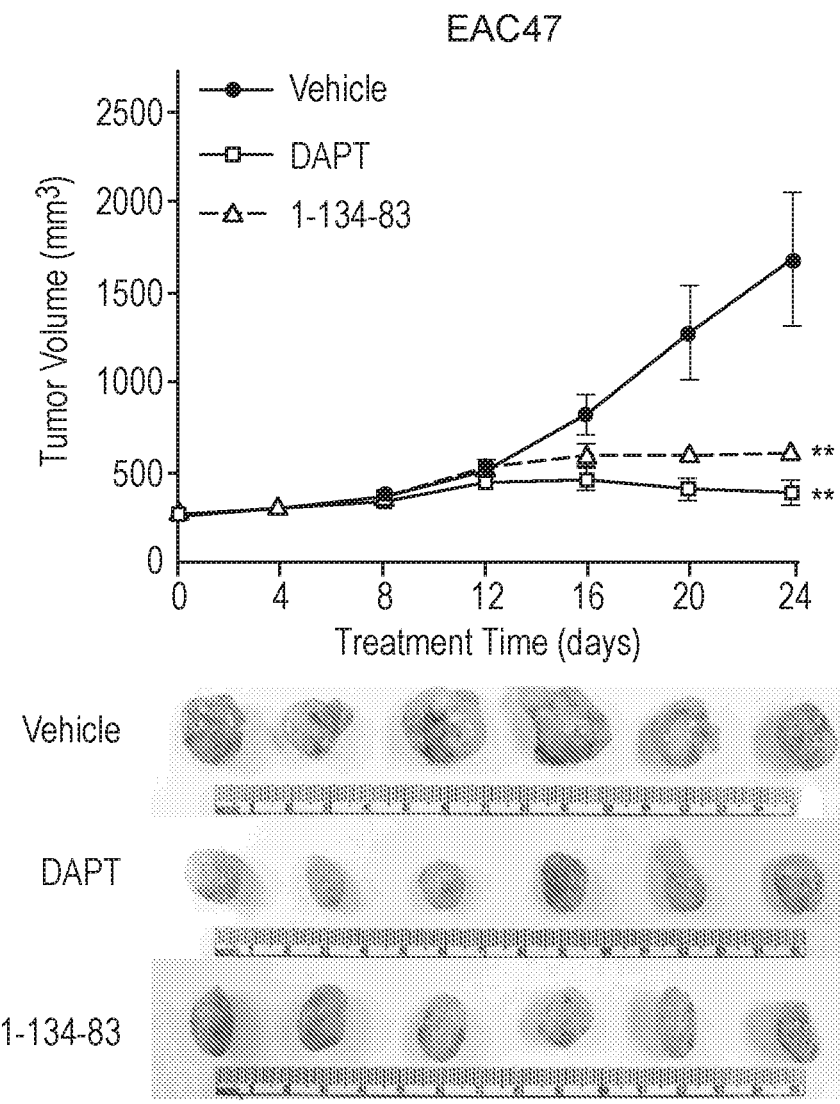
Figure 4D:
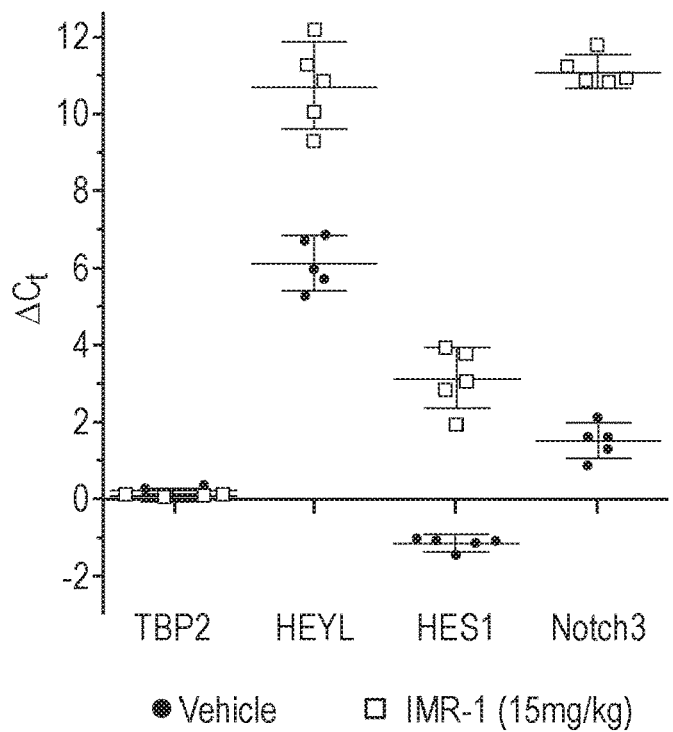
Figure 4E:
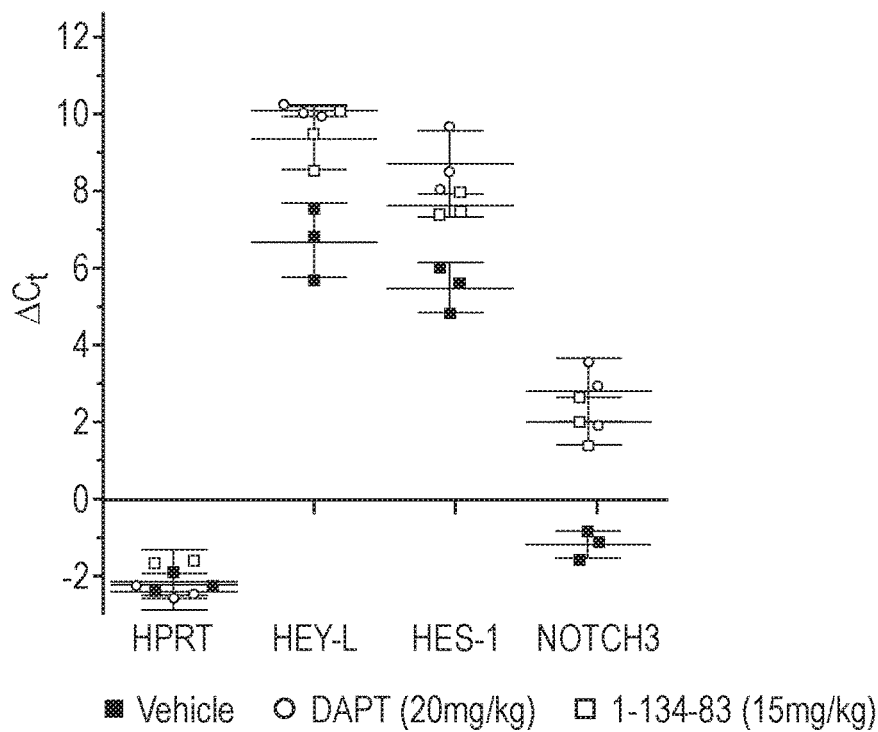
Figure 4F:
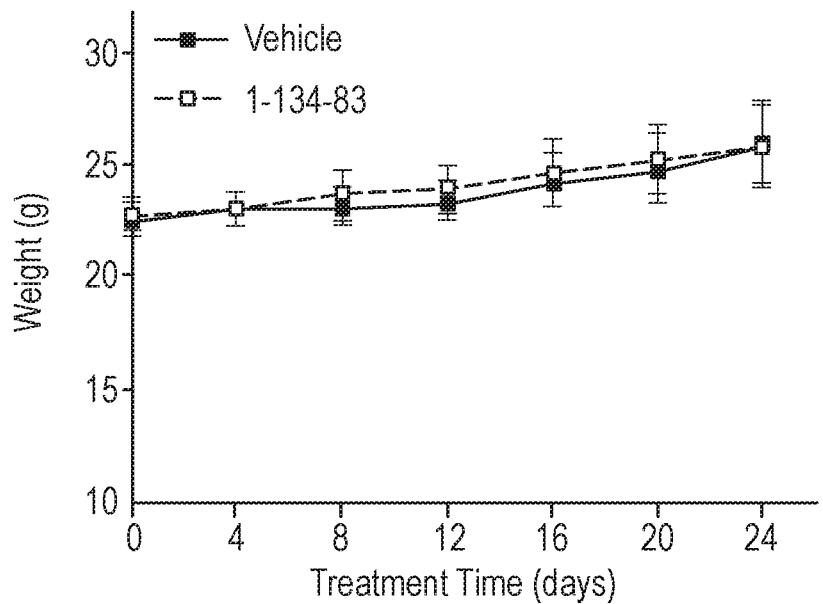
Figure 4G:
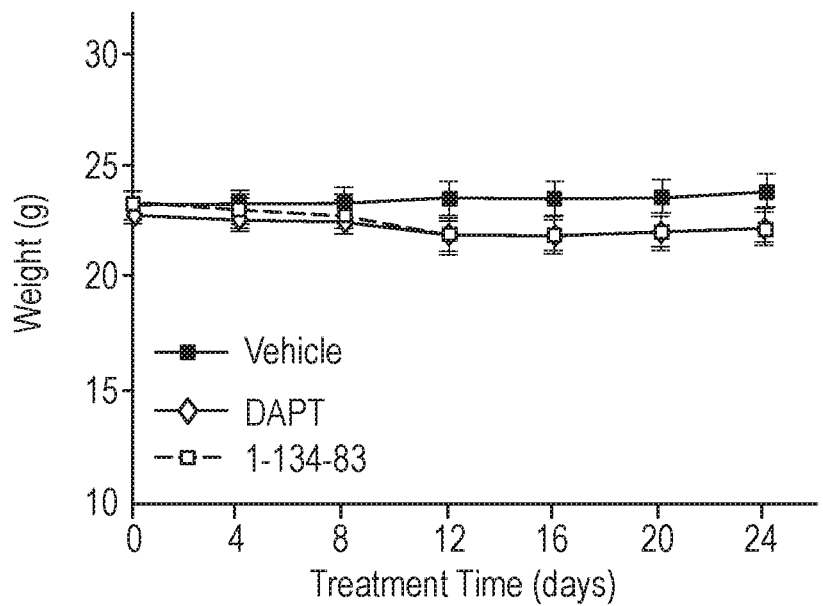

To extend the analysis of tumor cell growth inhibition, several commonly used cancer cell lines were selected to test for sensitivity to Inhibitor No. 1-134-83 (FIGS. 3A and 3B). These cell lines separated into two groups: (1) those whose transcription of Notch target genes were affected by treatment with Inhibitor No. 1-134-83 as well as DAPT, and (2) those whose transcription did not significantly change upon treatment. In this analysis, sensitivity to DAPT is taken to indicate specific inhibition of Notch activity. The sensitivity profile for cells treated with either Inhibitor No. 1-134-83 or DAPT was the same, indicating that Inhibitor No. 1-134-83 is specifically inhibiting Notch activity. Similarly, the colony formation displayed a similar stratification: cells whose transcription was sensitive to Inhibitor No. 1-134-83 and DAPT treatment were also impaired in their colony forming ability (FIG. 3C). Cells that are refractory to DAPT were equally resistant to Inhibitor No. 1-134-83. Even at a dose nearly 10× the effective concentration of 5

μM, Inhibitor No. 1-134-83 did not induce any cellular toxicity, strongly indicating that Inhibitor No. 1-134-83 is a specific inhibitor of Notch activity, and that it does not display off target effects. Taken together, these data indicate that the inhibitors disclosed herein selectively kill Notch-dependent cell lines via the inhibition of Notch-directed transcriptional activation by blocking the recruitment of MAML1 to the notch transcriptional complex on Chromatin.

Inhibition of Xenograft Tumor Growth

The effect of the inhibitors of the disclosure on tumor formation in an animal was investigated using a xenograft model. When introduced into the flank of nude mouse $5 \times 10^6$ OE19 cells, a human esophageal adenocarcinoma cell line readily forms tumors over the course of 4 weeks. When the animals were treated with 15 mg/kg of Inhibitor No. 1-134-83 beginning on the second day following transplantation, and continuing every day, tumor establishment was blocked. In contrast, treatment under the same regimen with a DMSO control had no effect on tumor growth. In addition, no adverse effects on the animal (e.g., a change in body weight) was observed throughout the course of treatment. (FIG. 4)

The effect of the inhibitors of the disclosure on the growth of an established tumor also was investigated using two independent esophageal adenocarcinoma patient-derived xenograft ("PDX") models. Tumors were established in NSG mice to the size of 250 mm$^3$ prior to the initiation of treatment. Mice were dosed daily via intraperitoneal ("IP") injection with either Inhibitor No. 1-134-83 (15 mg/kg) or DAPT (20 mg/kg), and compared to DMSO vehicle control. Treatment of both PDX tumors with Inhibitor No. 1-134-83 displayed significantly stunted growth to a similar level achieved with DAPT treatment, without any significant weight loss or other visible signs of stress in the treated animals. Following 24 days of treatment, tumors were harvested and Notch-target gene transcription was evaluated. In both PDX models, treatment with Inhibitor No. 1-134-83 dramatically reduced the level of the tested Notch target genes (Hes1, HeyL, Notch3). Similar reductions in Notch transcription were observed in DAPT treated tumors (right panel). Therefore, these data demonstrate that the inhibitors of the disclosure are first-in-class inhibitors of the Notch transcriptional activation complex with demonstrated efficacy in an animal tumor model. (FIG. 4)

Inhibition of Notch-Dependent Somite Development in Zebrafish.

The in vivo effects of the inhibitors of the disclosure also were investigated using *D. rerio*. Notch signaling plays a role in somite formation in developing vertebrate embryos. Changes in levels of Notch signaling (either increased or decreased) during development of the zebrafish embryo result in disruption of the symmetric, bilaterally formed somites, which can be readily observed. Thus, disruption of somitogenesis in zebrafish represents a convenient dose-sensitive readout for Notch pathway stimulation or inhibition.

Figure 5A:
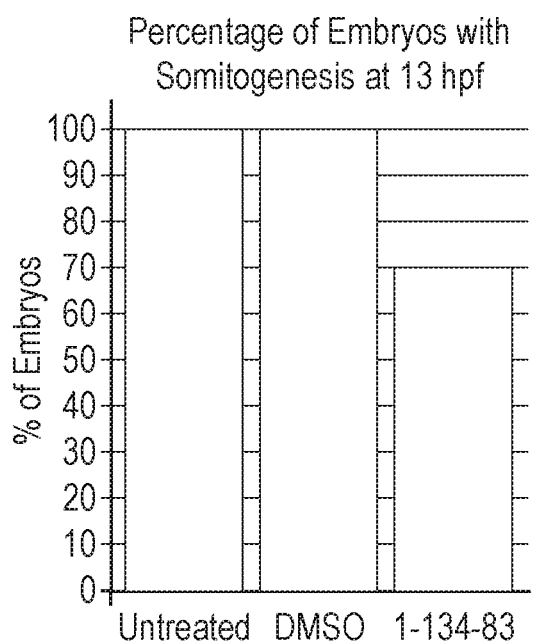
FIG. 5 illustrates that treatment of zebrafish embryos with Inhibitor No. 1-134-83 disrupts Notch-dependent somite formation in the zebrafish. Somite formation in zebrafish is sensitive to perturbations in Notch signaling. Coronal view of 13 hours post-fertilization ("hPF") zebrafish exposed to Inhibitor No. 1-134-83 at 8 hPF. Anterior to the left. Arrowheads denote somites. Negative controls are WT (untreated)
Figure 5B:
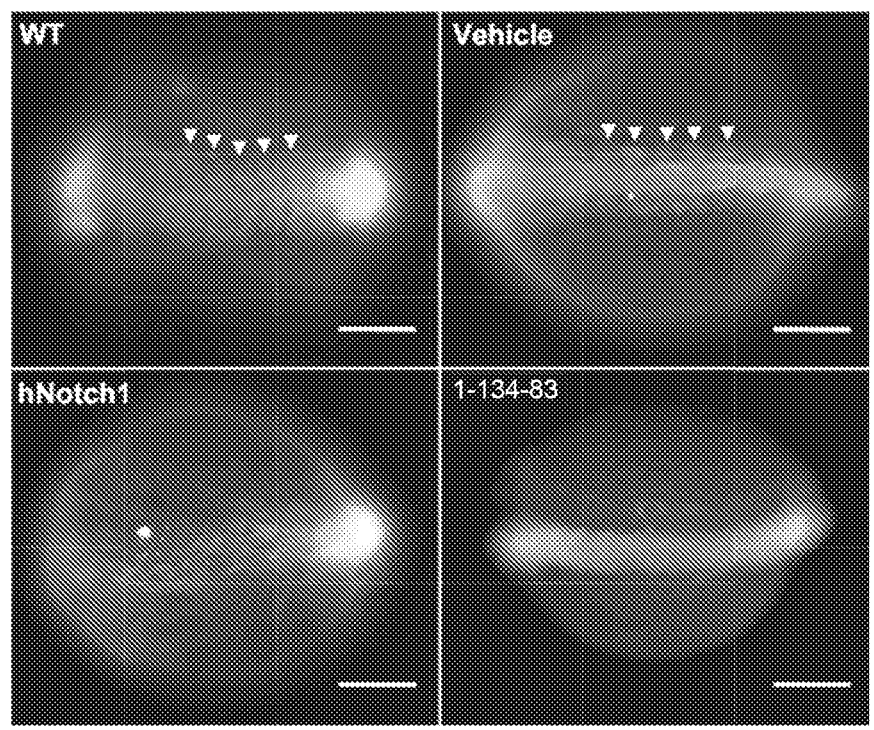

When 100 pg of mNotch1 was injected in mRNA, defects in somitogenesis in 90% of the embryos resulted (compared to 0% disrupted embryos in the control group) (FIG. 5). In contrast, embryos soaked in 40 μM Inhibitor No. 1-134-83 resulted in embryos with disrupted somites, consistent with alteration in Notch signaling. Disruption of somite formation was not observed, however, when embryos were soaked in vehicle control (DMSO). These results demonstrate that the inhibitors of the disclosure inhibit Notch signaling in vivo.

Further guidance for using the inhibitors of the disclosure can be found in the Examples section, below.

Pharmaceutical Formulations

Also provided herein are pharmaceutical formulations that include the inhibitors of the disclosure, and one or more pharmaceutically acceptable excipients.

The inhibitors of the disclosure can be administered to a subject or patient in a therapeutically effective amount. The inhibitors can be administered alone or as part of a pharmaceutically acceptable composition or formulation. In addition, the inhibitors can be administered all at once, as for example, by a bolus injection, multiple times, e.g. by a series of tablets, or delivered substantially uniformly over a period of time, as for example, using transdermal delivery. It is also noted that the dose of the compound can be varied over time.

The inhibitors disclosed herein can be administered in combination with one or more additional pharmaceutically active compounds/agents. The additional pharmaceutically active compounds/agents may be traditional small organic chemical molecules or can be macromolecules such as a proteins, antibodies, peptibodies, DNA, RNA or fragments of such macromolecules.

The inhibitors disclosed herein and other pharmaceutically active compounds, if desired, can be administered to a subject or patient by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. eneteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The inhibitors of the disclosure can be administered to a subject or patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the subject or patient, the severity of the condition or disease being treated, and the pharmacological activity of the compound being administered. The determination of dosage ranges and optimal dosages for a particular subject or patient is within the ordinary skill in the art.

When a subject or patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

In jurisdictions that forbid the patenting of methods that are practiced on the human body, the meaning of "administering" of a composition to a human subject or patient shall be restricted to prescribing a controlled substance that a human subject or patient will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

EXAMPLES

The following examples are provided for illustration and are not intended to limit the scope of the invention.

Notch Complex Assembly Assay

All recombinant proteins were expressed using baculovirus expression vectors in SF21 cells and purified. Unless otherwise stated, all assays contained 125 fmol of double stranded oligonucleotide, CSL, Notch1 and MAML1 proteins. Reactions were carried out in Tris-buffered saline with 0.1% Tween ("TBS-T") buffer containing 0.2% bovine serum albumin ("BSA") and 100 ug/mL salmon sperm DNA. Briefly, the Notch complex was assembled on a biotinylated double stranded ("DS") oligonucleotide harboring one CSL binding site (5'-AAACACGC-CGTGGGAAAAAATTTATG-3'). Complex assembly was quantitated using ALPHASCREEN technology (Perkin Elmer). Proteins in the complexes were detected using specific antibodies to either MAML1 (Cell signaling, D3K7B), Notch1 (Abcam, 52627) or CSL (anti-His, Abcam 18184). Streptavidin conjugated acceptor beads (Perkin Elmer, 6760002) were used to bind the DS oligonucleotide, and Protein-A conjugated donor beads (Perkin Elmer, 6760137) were used to detect antibody-coated proteins. For screening compounds, Notch transcriptional activation complex ("NTC") components were added to wells that already contained the inhibitor to be assayed and allowed to incubate for 30 minutes. The ALPHASCREEN plate (Perkin Elmer, 6008350) was then read on an Envision Plate reader (Perkin Elmer) as specified by the manufacturer.

Western Analysis

Protein analysis was carried out using conventional SDS-PAGE and transfer techniques. Blots were probed with the indicated antibody ("Ab"), using standard conditions, and detected using enhanced chemiluminescence ("ECL"). The following Ab were used: anti-Notch1 (ab52627, abcam), anti-Notch1$^{val1744}$ (4147S, Cell Signaling Technology) and anti-GAPDH (ab9483, Abcam).

Cell Lines

OE19 and OE33, human esophageal adenocarcinoma cell lines, were obtained from the European Collection of Cell Culture. SUM-149 and SUM-159, breast cancer cell lines, were obtained from Dr. Joyce Slingerland at the University of Miami School of Medicine. The following cell lines were obtained directly from the ATCC: 786-0, a human renal cell adenocarcinoma cell line; HT-1080, a human fibrosarcoma cell line; MCF-7, a mammary gland adenocarcinoma; T47D, a human mammary ductal carcinoma cell line; and H-23 a non-small cell lung adenocarcinoma cell line. All cell lines were propagated in growth media as specified.

Chromatin Immunoprecipitation ("ChIP") Analysis.

Cells ($8 \times 10^6$ $^{OE}33$ cells or $10 \times 10^6$ 786-0 cells) were plated onto a 15 cm tissue culture dish a day prior to treatment. Cells were then treated for 24 hours with (N—[N-(3,5-difluorophenacetyl)-L-alanyl]-S-phenylglycine t-butyl ester ("DAPT", 5 µM), Inhibitor No. 1-134-83 (25 µM), or DMSO vehicle. Following treatment, cells were cross-linked for 10 minutes with 1% formaldehyde. The reaction was then stopped by adding 0.125 NI glycine. Cells were collected in SDS lysis buffer (1% SDS, 10 mM EDTA, 50 mM Tris-HCl pH 8.0) and sonicated to yield chromatin fragments of approximately 300 to 800 bp (8 minutes at high level for OE33 cells; 5 minutes at medium level for 786-0 cells in BIORUPTOR UCD-200 sonicator). Lysates were divided into equal parts and immunoprecipitated with either α-Notch1 (A301-894A, Bethyl Laboratories) or α-MAML1 (12166s, Cell Signaling Technology) antibody. Protein: DNA immunoprecipitates were then reverse cross-linked at 65° C. in 200 mM NaCl for 4 hours, followed by incubation with RNase A and proteinase K. DNA was then purified using a PCR purification kit (28104, Qiagen). Immunoprecipitated DNA was then detected by SYBR green qPCR using HES1 specific oligonucleotide primers (forward: 5'CGTGTCTCCTCCTCCCATT3'; reverse: 5'GGGGGATTCCGCTGTTAT3').

RT-qPCR Analysis.

RT-PCR analysis was performed using TaqMan probes according to manufacturer's instructions. In particular, 80 ng of RNA equivalent was used per reaction. Gene expression was normalized to the TATA-binding protein ("TBP") gene. As a control, hypoxanthine phosphoribosyltransferase 1 ("HPRT") gene expression was also monitored.

Colony Assay

Cells were plated into a 6 well plate at a density of 2000 cells/cm². Inhibitor treatment commenced 24 hours post seeding, and the media containing inhibitor was changed every 48 hours thereafter. After 168 hours, cells were fixed with ice cold methanol for 10 minutes, stained for 1 hour with crystal violet, de-stained with water, and allowed to dry.

Mouse Xenograft Studies

Six-week-old NOD-SCID gamma ("NSG") mice were purchased from Jackson Laboratories and CD-1 Nude mice were purchased from Charles River Laboratories. For the cell line based xenografts assay, $5 \times 10^6$ $^{OE}19$ cells in 200 µl serum-free culture medium were injected subcutaneously per mouse. The mice in the treatment group were injected with 15 mg/kg of Inhibitor No. 1-134-83 daily, and the mice in the control group were injected with the same volume of vehicle (DMSO). Subcutaneous tumor growth was measured once every 4 days using calipers along with body weight. The experiment was discontinued on day 28. PDX cancer models were established, as described in Zhang et al, Establishment of Patient-Derived Xenograft (PDX) Models of Human Breast Cancer, Current Protocols in Mouse Biology, 3:21-29 (2013), in NSG mice. Briefly, 10 mm³ pieces of primary EAC29 PDX tumor were transplanted subcutaneously into the flanks of NSG mice using a 13G telescopic needle. When the tumors reached 200 mm³, the mice were split into two uniform groups for treatment. Compound 1-134-83 (15 mg/kg) and vehicle were administered daily by inraperitoneal ("IP") injection for 24 days. Tumor growth was monitored every 4 days and tumor volume was measured by the formula: Volume=(S×S×L)/2, where S and L are the short and long dimensions. The xenograft tumors were harvested, weighed and samples were subjected to histological examination and by qPCR.

Zebrafish Methodology

On three separate days, multiple clutches of embryos from two or more breeding pairs of the AB wild type line were combined and incubated at 28.5° C. for 8 hours in E3 medium with 0.1% (w/v) methylene blue. The embryos were then placed into fresh E3 medium with 0.1% (w/v) methylene blue containing 50 µM DMSO, 40 µM compound 1-134-83, or nothing. Zygotes were injected with 100 pg of human Notch1 intracellular domain mRNA mixed with 0.05% phenol red and using the MPPI-2 injection system from ASI, as a positive control. At 13 hours post fertilization, samples were collected and scored for the presence of discrete somite boarders on a Zeiss Stemi 2000-CS scope. Data was analyzed using Fisher's exact test in R3.1.0. Immunofluoresence was used to visualize the phenotype. Embryos were permeabilized with 10 µg/ml Proteinase K for 1 min and stained with EphA4 (Tyr-602), phosphor-specific Rabbit Polyclonal antibody from ECM Biosciences, for two days at 4° C. and 1:100 concentration. Embryos were then stained with ALEXA-488 anti-rabbit at 1:200 overnight. Samples were visualized on a Nikon Eclipse 801 and imaged with a photometrics cool snap ES.

Example 1

Synthetic Scheme for Targets NADi-094 and NADi-095

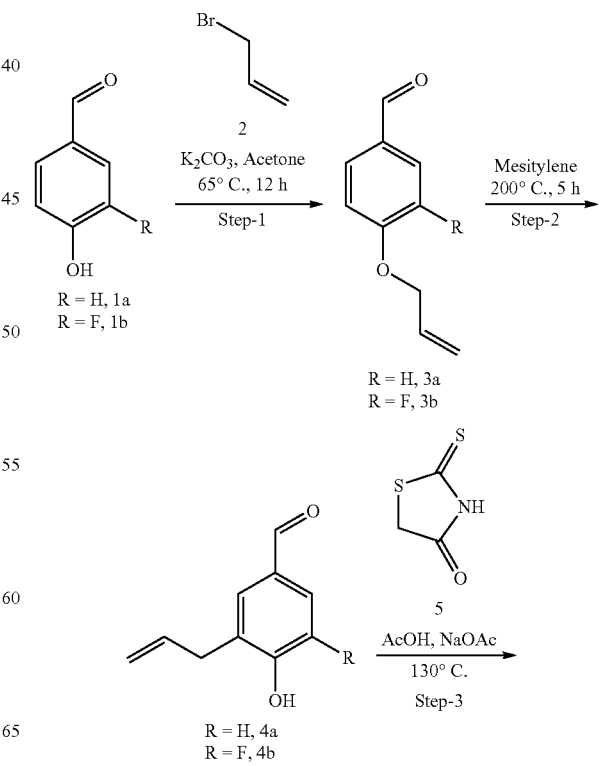

-continued

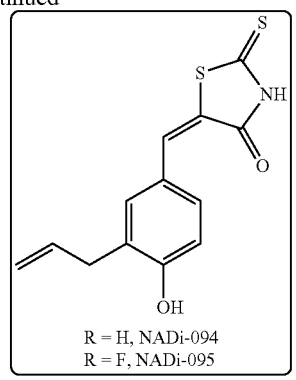

R = H, NADi-094
R = F, NADi-095

Preparation of 4-(Allyloxy)benzaldehyde (3a)

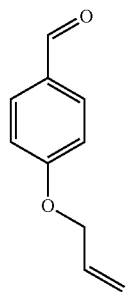

General Procedure 1:

To a solution of 4-hydroxybenzaldehyde 1a (500 mg, 4.09 mmol) in acetone (10 mL) was added 3-bromoprop-1-ene 2 (0.53 mL, 6.14 mmol) followed by potassium carbonate (848 mg, 6.14 mmol). The reaction mixture was heated at 65° C. for 12 h whereupon TLC showed the completion of the reaction. The reaction mixture was cooled to room temperature, filtered and concentrated in vacuo resulting in a crude residue which was treated with water and extracted with dichloromethane ("DCM"). The organic layer was washed with brine, dried over anhydrous $Na_2SO_4$ and concentrated in vacuo to afford 620 mg (93% yield) of the title compound 3a as a colourless oil. The crude compound was used in the next step without further purification. MS (ES+): m/z=204.10 $[M+ACN]^+$.

Preparation of 3-Allyl-4-hydroxybenzaldehyde (4a)

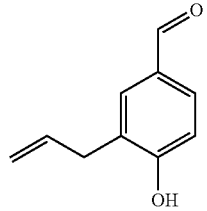

General Procedure 2:

A solution of 4-(allyloxy)benzaldehyde 3a (300 mg, 1.84 mmol) in mesitylene (3 mL) was heated at 200-205° C. for 5 h. The reaction mixture was allowed to cool to room temperature and concentrated in vacuo and purified by silica gel column chromatography eluting with 15-20% ethyl acetate in n-hexane to afford 180 mg (60% yield) of the title compound 4a as colourless oil. MS (ES+): m/z=163 [M+H].

Preparation of (Z)-5-(3-Allyl-4-hydroxybenzylidene)-2-thioxothiazolidin-4-one (NADi-094)

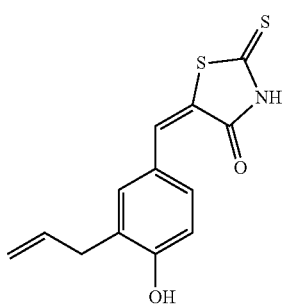 [SMILES: C=CCc1cc(/C=C2/SC(=S)NC2=O)ccc1O]

General Procedure 3:

To a solution of 3-allyl-4-hydroxybenzaldehyde 4a (180 mg, 1.10 mmol) and 2-thioxothiazolidin-4-one 5 (147 mg, 1.10 mmol) in glacial acetic acid (2 mL) was added sodium acetate (135 mg, 1.65 mmol). The reaction was heated to 130° C. for 16 h. The reaction mixture was poured into ice-cooled water and stirred for 15 min. The resultant precipitate was filtered, washed with diethyl ether/n-hexane and dried in vacuo to afford 60 mg (19% yield) of NADi-094 as a yellow solid. $^1$H NMR (400 MHz, $CD_3OD$) δ=7.52 (s, 1H), 7.22-7.32 (m, 2H), 6.90 (d, J=9.04 Hz, 1H), 6.01 (dd, J=10.25, 16.87 Hz, 1H), 5.05-5.14 (m, 2H), 3.39 (d, J=6.62 Hz, 2H); MS (ES+): m/z=276 [M−H]; HPLC=97.98%.

Preparation of 4-(Allyloxy)-3-fluorobenzaldehyde (3b)

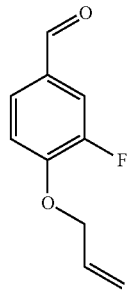

In a similar fashion as general procedure 1, a mixture of 3-fluoro-4-hydroxybenzaldehyde 1b (200 mg, 1.42 mmol, 3-bromoprop-1-ene 2 (0.18 mL, 2.14 mmol) and potassium carbonate (295 mg, 2.14 mmol) in acetone (10 mL) was heated at 65° C. for 12 h. After workup, the title compound 3b was isolated as a colourless oil (240 mg, 93%). The crude compound was used in the next step without further purification. MS (ES+): m/z=222 $[M+ACN]^+$.

Preparation of
3-Allyl-5-fluoro-4-hydroxybenzaldehyde (4b)

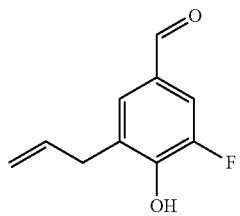

In a similar fashion as general procedure 2, a mixture of 2, 4-(allyloxy)-3-fluorobenzaldehyde 3b (50 mg, 0.55 mmol) in mesitylene (1 mL) was heated at 200-205° C. for 5 h. After workup and purification, the title compound 4b was isolated as a colourless oil (50 mg, 98% yield). MS (ES+): m/z=221 [M+ACN].

Preparation of (Z)-5-(3-Allyl-5-fluoro-4-hydroxy-benzylidene)-2-thioxothiazolidin-4-one (NADi-095) 2

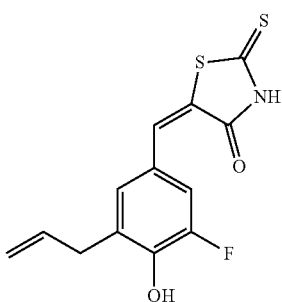 [SMILES: C=CCc1cc(/C=C2/SC(=S)NC2=O)cc(F)c1O]

In a similar fashion as general procedure 3, a mixture of 3-allyl-5-fluoro-4-hydroxybenzaldehyde 4b (50 mg, 0.27 mmol), 2-thioxothiazolidin-4-one 5 (37 mg, 0.27 mmol) and sodium acetate (34 mg, 0.41 mmol) in glacial acetic acid (1 mL) was heated at 130° C. for 16 h. After workup and purification, the title compound NADi-095 was isolated as a yellow solid (55 mg, 67% yield). $^1$H NMR (400 MHz, CD$_3$OD) δ 7.48 (s, 1H), 7.16 (d, J=11.47 Hz, 1H), 7.11 (s, 1H), 6.00 (dd, J=10.03, 16.87 Hz, 1H), 5.13 (d, J=5.29 Hz, 1H), 5.10 (s, 1H), 3.44 (d, J=6.39 Hz, 2H)=; MS (ES+): m/z=294 [M−H]; HPLC=96.81%.

Example 2

Synthetic Scheme for Target NADi-098

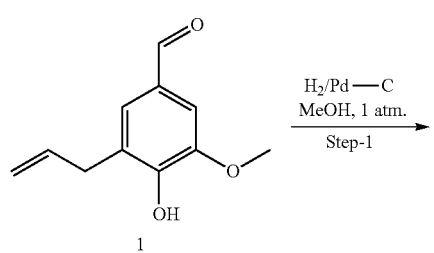

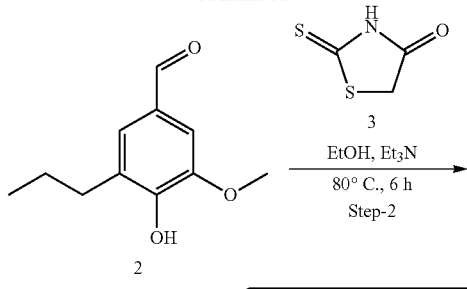

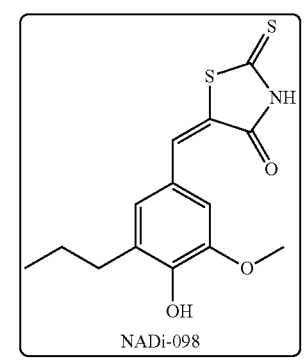

Preparation of
4-Hydroxy-3-methoxy-5-propylbenzaldehyde (2)

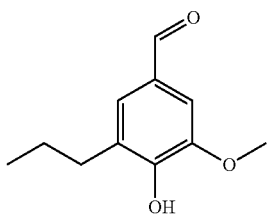

To a solution of 3-allyl-4-hydroxy-5-methoxybenzaldehyde 1 (300 mg, 1.56 mmol) in ethyl acetate (5 mL) was added 10% Pd/C (60 mg) under argon atmosphere. The resulting solution was stirred under a hydrogen atmosphere at room temperature for 12 h. The reaction mixture was filtered through a Celite pad and the filtrate was concentrated in vacuo to afford 250 mg (82% yield) of the title compound 2 as a pale yellow solid. The crude compound was used in the next step without further purification. MS (ES+): m/z=195 [M+H].

Preparation of (Z)-5-(4-Hydroxy-3-methoxy-5-propylbenzylidene)-2-thioxothiazolidin-4-one (NADi-098)

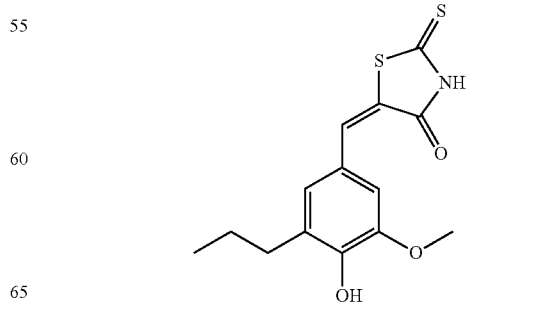

General Procedure 4:

To a solution of 2-thioxothiazolidin-4-one 3 (69 mg, 0.51 mmol) in ethanol (4 mL) was added 4-hydroxy-3-methoxy-5-propylbenzaldehyde 2 (100 mg, 0.51 mmol) followed by triethylamine (0.14 mL, 1.02 mmol). The reaction mixture was heated at 80° C. for 6 h, at which time TLC analysis showed completion of the reaction. The reaction mixture was concentrated in vacuo to dryness resulting in a crude solid, which was washed with water and purified by recrystallization using acetonitrile to afford 34 mg (21% yield) of NADi-098 as a yellow solid. $^1$H NMR (400 MHz, DMSO-$d_6$) δ=13.70 (br. s, 1H), 9.52 (s, 1H), 7.56 (s, 1H), 7.06 (d, J=1.78 Hz, 1H), 6.98 (d, J=1.78 Hz, 1H), 3.86 (s, 3H), 2.53-2.58 (m, 2H), 1.50-1.62 (m, 2H), 0.91 (t, J=7.36 Hz, 3H); MS (ES+): m/z=310 [M+H]; HPLC=92.18%.

Example 3

Synthetic Scheme for Target NADi-117

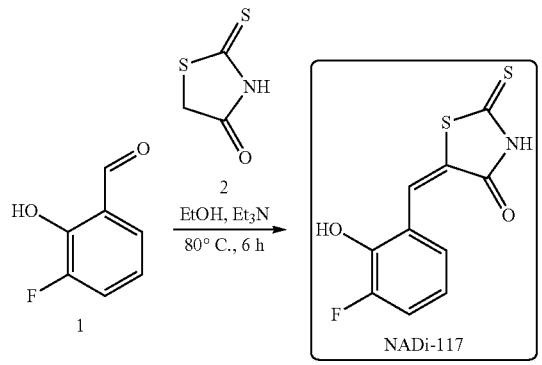

Preparation of (Z)-5-(3-Fluoro-2-hydroxybenzylidene)-2-thioxothiazolidin-4-one (NADi-117)

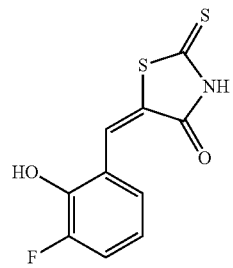 [SMILES: O=C1NC(=S)S/C1=C/c1cccc(F)c1O]

In a similar fashion as general procedure 4, a mixture of 2-thioxothiazolidin-4-one 2 (150 mg, 1.12 mmol) 3-fluoro-2-hydroxybenzaldehyde 1 (158 mg, 1.12 mmol) and triethylamine (0.3 mL, 2.25 mmol) in ethanol (4 mL) was heated at 80° C. for 6 h. After workup and recrystallization, the title compound NADi-117 was isolated as a yellow solid (15 mg, 6% yield). $^1$H NMR (400 MHz, DMSO-$d_6$) δ=13.80 (br. s, 1H), 10.81 (s, 1H), 7.83 (s, 1H), 7.25-7.41 (m, 1H), 7.16 (d, J=7.94 Hz, 1H), 6.98 (dt, J=5.29, 7.94 Hz, 1H); MS (ES+): m/z=254 [M−H]; HPLC=96.54%.

Example 4

Synthetic Scheme for Target NADi-140

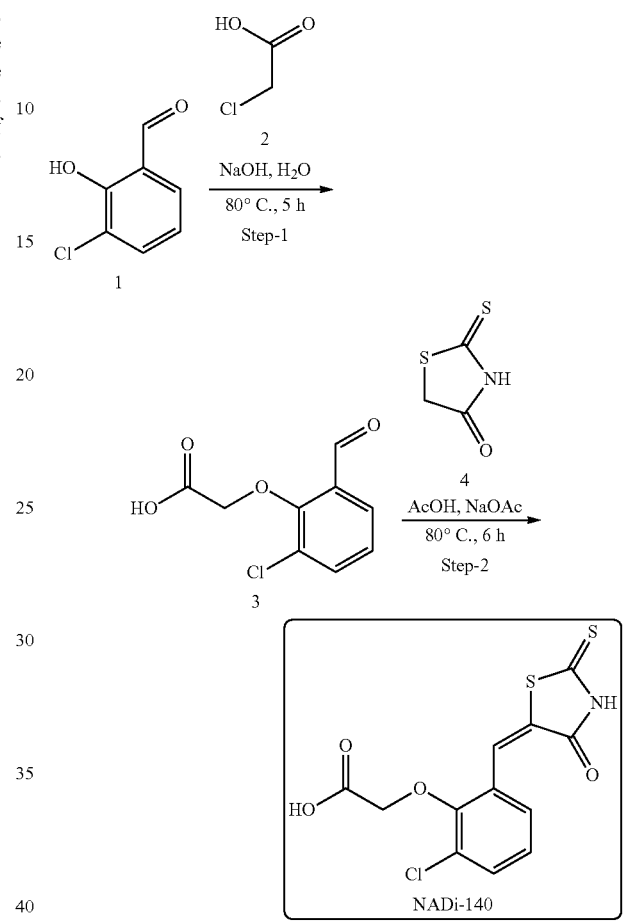

Preparation of 2-(2-Chloro-6-formylphenoxy)acetic acid (3)

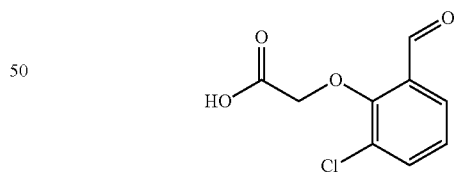

To a solution of 3-chloro-2-hydroxybenzaldehyde 1 (500 mg, 3.19 mmol) in water (6 mL) was added sodium hydroxide (255 mg, 6.38 mmol) followed by 2-chloroacetic acid 2 (301 mg, 3.19 mmol). The reaction mixture was heated to 80° C. for 5 h, at which time TLC analysis showed completion of reaction. The reaction mixture was acidified with 1M HCl and extracted with ethyl acetate (3×15 mL). The combined fractions were dried over anhydrous $Na_2SO_4$, filtered and concentrated in vacuo. The crude product was purified by combiflash eluting with 20-25% ethyl acetate in hexane to afford 310 mg (45% yield) of the title compound 3 as a yellow solid. MS (ES+): m/z=213.95 [M+H]$^+$.

Preparation of (Z)-2-(2-Chloro-6-((4-oxo-2-thio-xothiazolidin-5-ylidene)methyl)phenoxy)acetic acid (NADi-140)

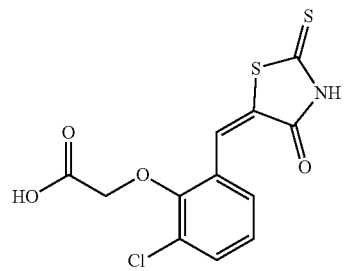 [SMILES: O=C(O)COc1c(Cl)cccc1/C=C1/SC(=S)NC1=O]

In a similar fashion as general procedure 3, a mixture of 2-(2-chloro-6-formylphenoxy)acetic acid 3 (250 mg, 1.16 mmol), 2-thioxothiazolidin-4-one 4 (155 mg, 1.16 mmol) and sodium acetate (143 mg, 1.74 mmol) in glacial acetic acid (5 mL) was heated at 90° C. for 6 h. After workup and purification, the title compound NADi-140 was isolated as a yellow solid (154 mg, 40% yield). $^1$H NMR (400 MHz, DMSO-$d_6$) δ=7.62 (s, 1H), 7.42 (d, J=8.03 Hz, 1H), 7.36 (d, J=8.03 Hz, 1H), 7.16-7.24 (m, 1H), 4.07 (s, 2H); MS (ES+): m/z=328 [M−H]; HPLC=96.33%.

Example 5

Synthetic Scheme for Target NADi-158

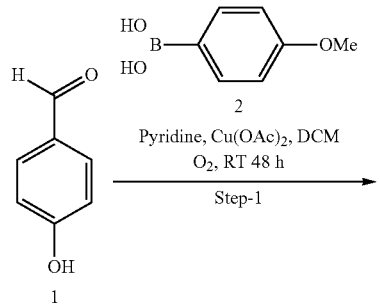

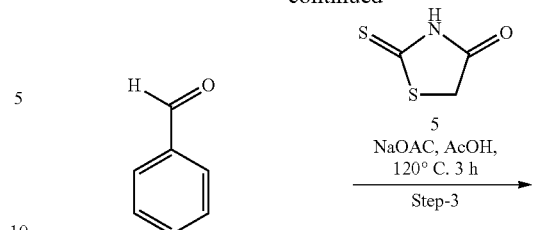

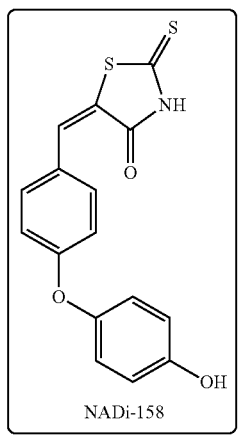

NADi-158

Preparation of 4-(4-Methoxyphenoxy)benzaldehyde (3)

To a solution of 4-hydroxybenzaldehyde 1 (250 mg, 1.86 mmol) in DCM (15 mL) was added pyridine (0.3 mL, 3.72 mmol) and (4-methoxyphenyl)boronic acid 2 (312 mg, 2.05 mmol). The solution was purged with oxygen for 15 min. To this solution was added copper acetate (490 mg, 2.79 mmol) and the reaction mixture was stirred at room temperature under oxygen atmosphere for 48 h. The reaction mixture was filtered through a Celite pad and washed with DCM. The filtrate was concentrated under reduced pressure and the residue was purified by silica gel column chromatography eluting with 10-15% ethyl acetate in n-hexane to afford 160 mg (36% yield) of the title compound 3 as an off white solid. MS (ES+): m/z=292 [M+ACN+Na].

Preparation of 4-(4-Hydroxyphenoxy)benzaldehyde (4)

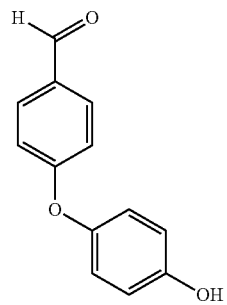 [SMILES: O=Cc1ccc(Oc2ccc(O)cc2)cc1]

General Procedure 5:

To a solution of 4-(4-methoxyphenoxy)benzaldehyde 3 (160 mg, 0.70 mmol) in DCM (5 mL) was added boron tribromide (1M in DCM, 2.1 mL, 2.10 mmol) at 0° C., and the reaction was stirred at room temperature for 18 h. TLC showed completion of reaction. The reaction mixture was quenched with saturated aqueous NaHCO$_3$ solution and extracted repeatedly with DCM. The combined organics were dried over anhydrous Na$_2$SO$_4$, filtered and concentrated in vacuo. The resultant residue was purified by silica gel column chromatography eluting with 10-15% ethyl acetate in n-hexane to afford 90 mg (60% yield) of the title compound 4 as an off white solid. $^1$H NMR (400 MHz, CDCl$_3$) δ=9.91 (s, 1H), 7.83 (d, J=8.87 Hz, 2H), 7.00 (dd, J=8.87, 11.09 Hz, 4H), 6.85-6.92 (m, 2H).

Preparation of (Z)-5-(4-(4-Hydroxyphenoxy)benzylidene)-2-thioxothiazolidin-4-one (NADi-158)

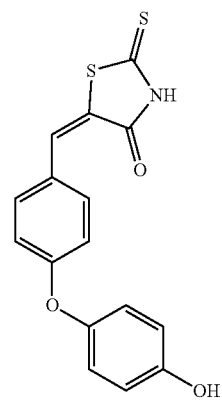 [SMILES: O=C1NC(=S)S/C1=C/c1ccc(Oc2ccc(O)cc2)cc1]

In a similar fashion as general procedure 3, a mixture of 4-(4-hydroxyphenoxy)benzaldehyde 4 (80 mg, 0.37 mmol), 2-thioxothiazolidin-4-one 5 (50 mg, 0.37 mmol) and sodium acetate (46 mg, 0.55 mmol) in glacial acetic acid (2 mL) was heated at 120° C. for 3 h. After workup, the crude residue was purified by preparative HPLC to provide the title compound NADi-158 as a yellow solid (40 mg, 33% yield). $^1$H NMR (400 MHz, DMSO-d$_6$) δ=13.78 (br. s, 1H), 9.47 (s, 1H), 7.54-7.63 (m, 3H), 7.01 (d, J=7.94 Hz, 2H), 6.97 (d, J=8.38 Hz, 2H), 6.82 (d, J=7.50 Hz, 2H); HPLC=98.85%.

Example 6

Synthetic Scheme for Target NADi-163

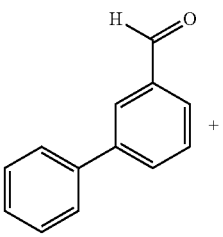
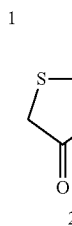
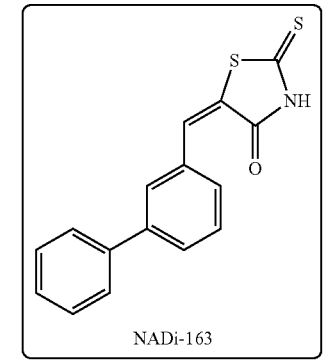

Preparation of (Z)-5-([1,1'-Biphenyl]-3-ylmethylene)-2-thioxothiazolidin-4-one (NADi-163)

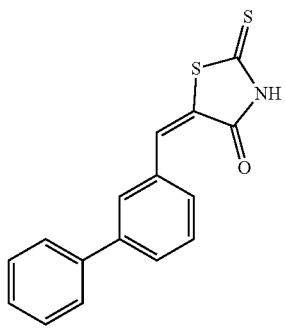 [SMILES: O=C1NC(=S)S/C1=C/c1cccc(-c2ccccc2)c1]

In a similar fashion as general procedure 3, a mixture of [1,1'-biphenyl]-3-carbaldehyde 1 (200 mg, 1.09 mmol), 2-thioxothiazolidin-4-one 2 (133 mg, 1.09 mmol) and sodium acetate (123 mg, 1.63 mmol) in glacial acetic acid (2 mL) was heated at 120° C. for 12 h. After workup and purification, the title compound NADi-163 was isolated as a yellow solid (60 mg, 18% yield). $^1$H NMR (400 MHz, DMSO-d$_6$) δ=13.88 (br. s, 1H), 7.89 (s, 1H), 7.80 (d, J=7.94 Hz, 1H), 7.70-7.76 (m, 3H), 7.62-7.68 (m, 1H), 7.56-7.60

(m, 1H), 7.51 (t, J=7.50 Hz, 2H), 7.43 (d, J=7.50 Hz, 1H); MS (ES+): m/z=296 [M−H]; HPLC=99.51%.

Example 7

Synthetic Scheme for Target NADi-170

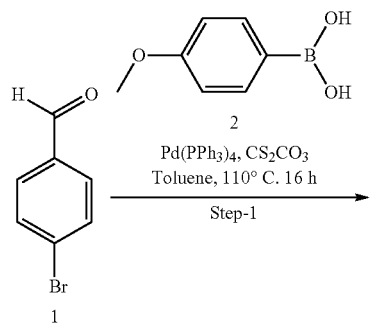

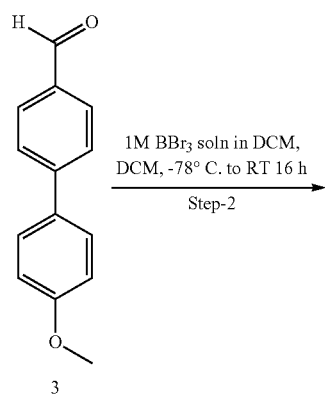

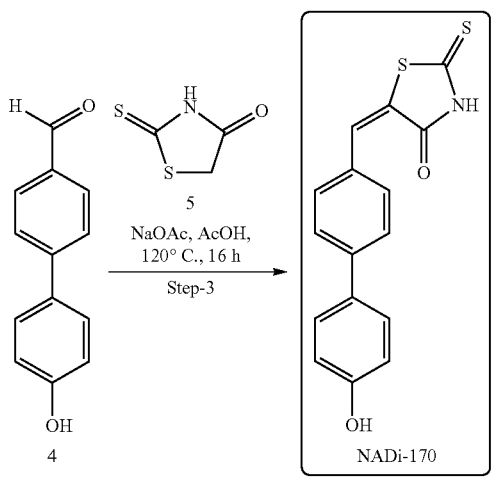

Preparation of 4'-Methoxy-[1,1'-biphenyl]-4-carbaldehyde (3)

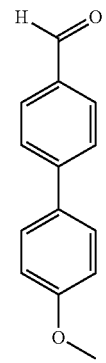

To a solution of 4-bromobenzaldehyde 1 (1 g, 5.40 mmol) in toluene (20 mL) was added (4-methoxyphenyl)boronic acid 2 (1.05 g, 7.02 mmol) and the solution was degassed with argon for 15 min. To the resulting solution was added tetrakis(triphenyl phosphine)palladium(0) (600 mg, 5.40 mmol) and cesium carbonate (5.3 g, 16.2 mmol). The mixture was heated to reflux at 110° C. for 16 h. The reaction mixture was cooled to room temperature and filtered through a pad of Celite. The filter cake was washed with ethyl acetate. The filtrate and washings were combined, washed with water, brine, dried over anhydrous $Na_2SO_4$, filtered and concentrated in vacuo. The residue was purified by silica gel column chromatography eluting with 2-4% ethyl acetate in n-hexane to afford 810 mg (71% yield) of the title compound 3 as an off white solid. MS (ES+): m/z=213 [M+H].

Preparation of 4'-Hydroxy-[1,1'-biphenyl]-4-carbaldehyde (4)

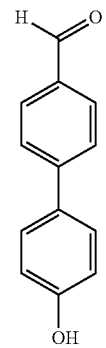

In a similar fashion as general procedure 5, a mixture of 4'-methoxy-[1,1'-biphenyl]-4-carbaldehyde 3 (530 mg, 2.12 mmol) and boron tribromide (1M in DCM, 2.1 mL, 2.10 mmol) in DCM (4 mL) was stirred at −78° C. for 16 h. After workup, the crude product was purified by silica gel column chromatography eluting with 8-10% ethyl acetate in n-hexane to provide the title compound 4 as an off-white solid (100 mg, 72%). $^1$H NMR (400 MHz, $CDCl_3$) δ=10.04 (s, 1H), 7.93 (d, J=8.43 Hz, 2H), 7.71 (d, J=8.43 Hz, 2H), 7.51-7.57 (m, 2H), 6.92-6.97 (m, 2H).

137

Preparation of (Z)-5-((4'-Hydroxy-[1,1'-biphenyl]-4-yl)methylene)-2-thioxothiazolidin-4-one (NADi-170)

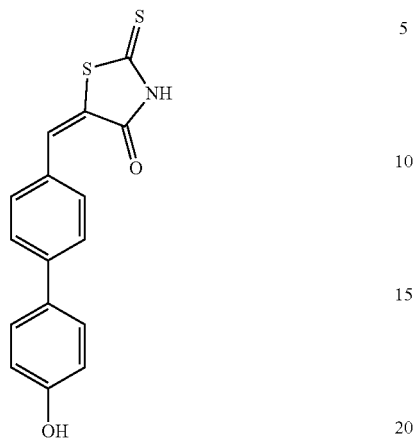

In a similar fashion as general procedure 3, a mixture of 4'-hydroxy-[1,1'-biphenyl]-4-carbaldehyde 4 (60 mg, 0.30 mmol), 2-thioxothiazolidin-4-one 5 (40 mg, 0.30 mmol) and sodium acetate (36 mg, 0.45 mmol) in glacial acetic acid (2 mL) was heated at 120° C. for 16 h. After workup, the crude product was purified by triturating with ethanol. The title compound NADi-170, 6 mg (19% yield) was isolated as a yellow solid. $^1$H NMR (400 MHz, DMSO-$d_6$) δ=13.83 (br. s, 1H), 9.73 (s, 1H), 7.79 (d, J=8.38 Hz, 2H), 7.57-7.70 (m, 5H), 6.83-6.91 (m, 2H); MS (ES+): m/z=312 [M−H]; HPLC=96.82%.

Example 8

Synthetic Scheme for Targets NADi-177 and NADi-184

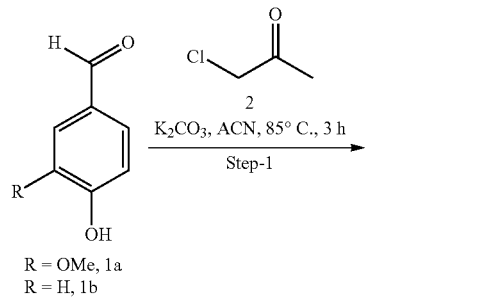

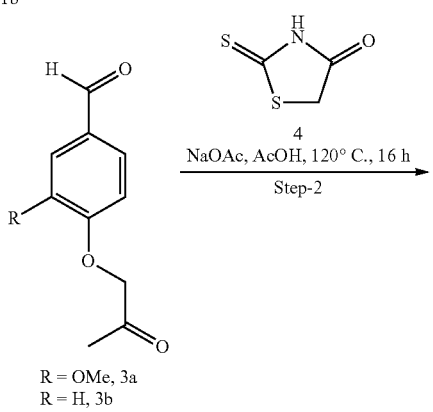

138

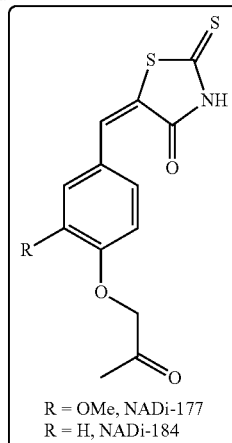

R = OMe, NADi-177
R = H, NADi-184

Preparation of 3-Methoxy-4-(2-oxopropoxy)benzaldehyde (3b)

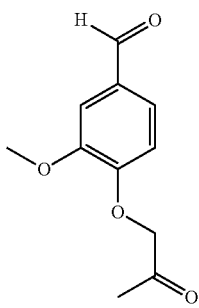

General Procedure 6:

To a solution of 4-hydroxy-3-methoxybenzaldehyde 1a (600 mg, 3.94 mmol) in acetonitrile (10 mL) was added 1-chloropropan-2-one 2 (0.48 mL, 5.91 mmol) and potassium carbonate (815 mg, 5.91 mmol). The reaction mixture was heated at 85° C. for 3 h. The reaction mixture was cooled to room temperature and concentrated in vacuo. The crude residue was diluted with water, and the aqueous mixture was extracted with ethyl acetate. The combined organic fractions layer were dried over anhydrous $Na_2SO_4$, filtered and concentrated in vacuo. The residue was purified by silica gel column chromatography eluting with 10-15% ethyl acetate in n-hexane to afford 500 mg (56% yield) of the title compound 3a as a colourless thick liquid. $^1$H NMR (400 MHz, CDCl$_3$) δ=9.87 (s, 1H), 7.46 (d, J=1.71 Hz, 1H), 7.43 (d, J=1.71 Hz, 1H), 7.41 (d, J=1.71 Hz, 1H), 4.70 (s, 2H), 3.96 (s, 3H), 2.30 (s, 3H).

Preparation of (Z)-5-(3-Methoxy-4-(2-oxopropoxy)benzylidene)-2-thioxothiazolidin-4-one (NADi-177)

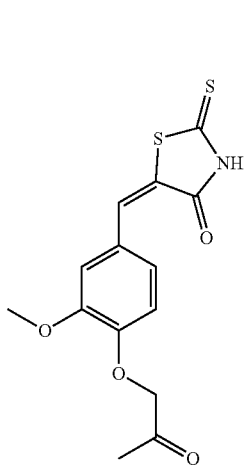 [SMILES: COc1cc(/C=C2/SC(=S)NC2=O)ccc1OCC(C)=O]

In a similar fashion as general procedure 3, a mixture of 3-methoxy-4-(2-oxopropoxy)benzaldehyde 3a (400 mg, 1.78 mmol), 2-thioxothiazolidin-4-one 4 (237 mg, 1.78 mmol) and sodium acetate (219 mg, 2.67 mmol) in glacial acetic acid (10 mL) was heated at 120° C. for 16 h. After workup and trituration with ethanol, the title compound NADi-177 was isolated as a yellow solid (200 mg, 35% yield). $^1$H NMR (400 MHz, CDCl$_3$) δ=13.76 (br. s, 1H), 7.61 (s, 1H), 7.20 (s, 1H), 7.13 (d, J=8.38 Hz, 1H), 6.98 (d, J=8.38 Hz, 1H), 4.93 (s, 2H), 3.85 (s, 3H), 2.16 (s, 3H); MS (ES+): m/z=323 [M−H]; HPLC=95.79%.

Preparation of 4-(2-Oxopropoxy)benzaldehyde (3a)

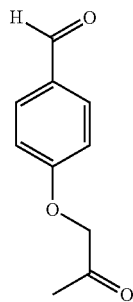

In a similar fashion as general procedure 6, a mixture of 4-hydroxybenzaldehyde 1b (500 mg, 4.09 mmol), 4-chlorobutan-2-one 2 (0.49 mL, 6.13 mmol) and potassium carbonate (846 mg, 6.13 mmol) in acetonitrile (10 mL) was heated at 85° C. for 2 h. After workup, the title compound 3b was isolated as sticky mass (700 mg, 96% yield). The crude compound was used in the next step without further purification. $^1$H NMR (400 MHz, DMSO-d$_6$) δ=9.87 (s, 1H), 7.85 (d, J=8.38 Hz, 2H), 7.09 (d, J=8.38 Hz, 2H), 4.99 (s, 2H), 2.50 (s, 3H); MS (ES+): m/z=179.10 [M+H]$^+$.

Preparation of (Z)-5-(4-(2-Oxopropoxy)benzylidene)-2-thioxothiazolidin-4-one (NADi-184)

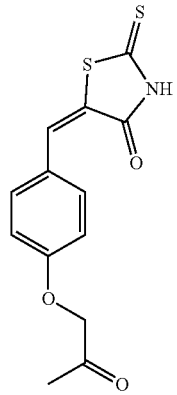 [SMILES: CC(=O)COc1ccc(/C=C2/SC(=S)NC2=O)cc1]

In a similar fashion as general procedure 3, to a mixture of 4-(2-oxopropoxy)benzaldehyde 3b (150 mg, 0.84 mmol) and 2-thioxothiazolidin-4-one 4 (112 mg, 0.84 mmol) in glacial acetic acid (2 mL) was added sodium acetate (103 mg, 1.26 mmol). The reaction mixture was heated to 120° C. for 16 h. The reaction mixture was poured into ice cooled water and stirred for 15 min. The solid was collected by filtration, washed with diethyl ether/n-hexane and dried to afford 35 mg (14% yield) of NADi-184 as a yellow solid. $^1$H NMR (400 MHz, DMSO-d$_6$)=13.76 (br. s, 1H), 7.61 (s, 1H), 7.55 (d, J=8.82 Hz, 2H), 7.07 (d, J=8.82 Hz, 2H), 4.95 (s, 2H), 2.17 (s, 3H); MS (ES+): m/z=292 [M−H]; HPLC=95.84%.

Example 9

Synthetic Scheme for Targets NADi-181, NADi-187 and NADi-188

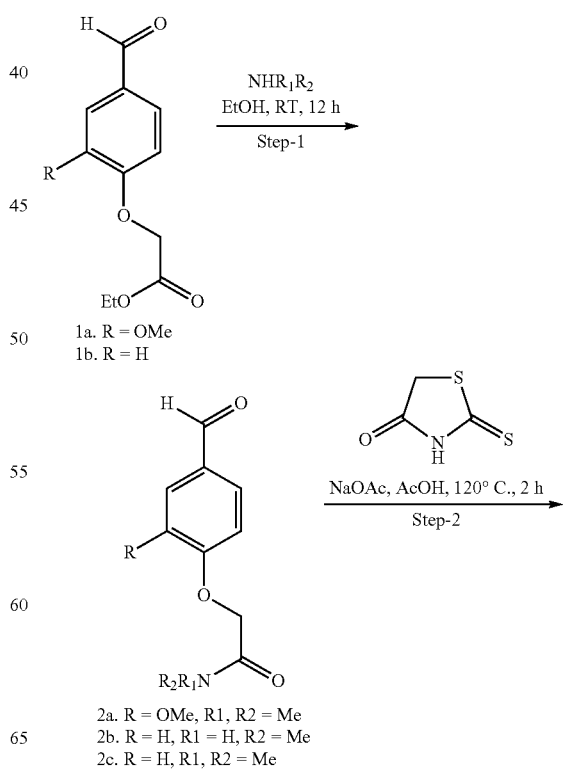

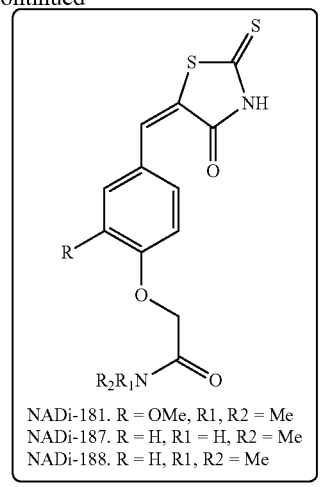

NADi-181. R = OMe, R1, R2 = Me
NADi-187. R = H, R1 = H, R2 = Me
NADi-188. R = H, R1, R2 = Me

Preparation of 2-(4-Formyl-2-methoxyphenoxy)-N,N-dimethylacetamide (2a)

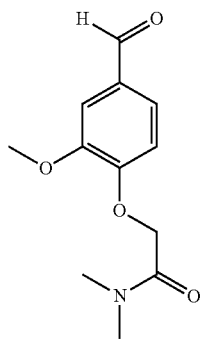 [SMILES: COc1cc(C=O)ccc1OCC(=O)N(C)C]

General Procedure 7:

To a solution of ethyl 2-(4-formyl-2-methoxyphenoxy) acetate 1a (200 mg, 0.84 mmol) in ethanol (2 mL) was added 2M solution of dimethyl amine in THF (5 mL, 10.0 mmol) and the mixture was stirred at room temperature for 12 h. The reaction was monitored by TLC (100% ethyl acetate $R_f$=0.3). The reaction mixture was concentrated in vacuo to dryness resulting in 170 mg of the crude compound 2a. The crude compound was used in the next step without further purification.

Preparation of (Z)-2-(2-Methoxy-4-((4-oxo-2-thioxothiazolidin-5-ylidene)methyl)phenoxy)-N,N-dimethylacetamide (NADi-181)

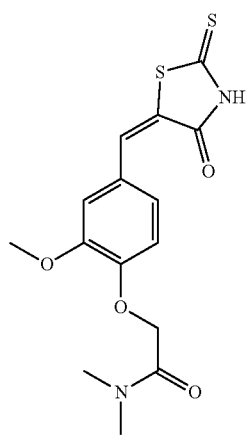 [SMILES: COc1cc(/C=C2/SC(=S)NC2=O)ccc1OCC(=O)N(C)C]

In a similar fashion as general procedure 3, a mixture of 2-(4-formyl-2-methoxyphenoxy)-N,N-dimethylacetamide 2a (200 mg, 0.84 mmol), 2-thioxothiazolidin-4-one 3 (122 mg, 0.92 mmol) and sodium acetate (103 mg, 1.25 mmol) in acetic acid (5 mL) was heated at 120° C. for 12 h. After workup and purification, the title compound NADi-181 was obtained as a yellow solid (70 mg, 24% yield). $^1$H NMR (400 MHz, DMSO-$d_6$): δ 13.75 (br. s, 1H), 7.61 (s, 1H), 7.19 (s, 1H), 7.15 (d, J=8.82 Hz, 1H), 7.00 (d, J=8.38 Hz, 1H), 4.93 (s, 2H), 3.85 (s, 3H), 3.00 (s, 3H), 2.84 (s, 3H); MS (ES+): m/z=353 [M+H]; HPLC=97.50%.

Preparation of 2-(4-formylphenoxy)-N-methylacetamide (2b)

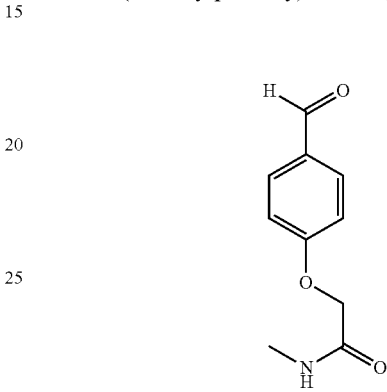

In a similar fashion as general procedure 7, a mixture of ethyl 2-(4-formylphenoxy)acetate 1b (150 mg, 0.72 mmol) and methyl amine (40% in water, 5 ml, 10 mmol) in ethanol (2 mL) was stirred at room temperature for 12 h. The reaction was monitored by TLC (100% ethyl acetate, $R_f$=0.3). The mixture was concentrated in vacuo to provide the title compound 2b as a pale yellow crude oil (145 mg, 83%).

Preparation of (Z)—N-methyl-2-(4-((4-oxo-2-thioxothiazolidin-5-ylidene)methyl)phenoxy) acetamide (NADi-187)

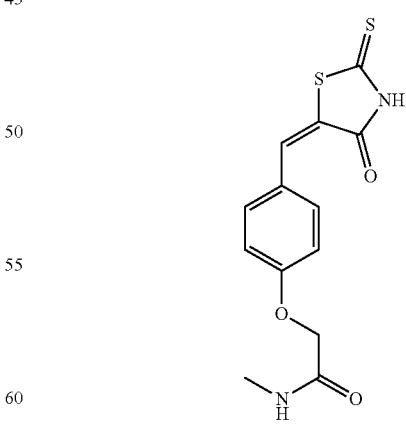

In a similar fashion as general procedure 3, a mixture of (4-formylphenoxy)-N-methylacetamide 2b (0.14 mg, 0.84 mmol), 2-thioxothiazolidin-4-one 3 (105 mg, 0.79 mmol) and sodium acetate (88 mg, 1.08 mmol) in acetic acid (5 mL) was heated at 120° C. for 12 h. After workup and purification, the title compound NADi-187 was obtained as a yellow solid (150 mg, 67% yield). $^1$H NMR (400 MHz, DMSO-$d_6$): δ 13.77 (br s, 1H), 8.09 (br s, 1H), 7.61 (s, 1H), 7.59 (d, J=8.82 Hz, 2H), 7.12 (d, J=8.82 Hz, 2H), 4.57 (s, 2H), 2.66 (d, J=4.41 Hz, 3H); MS (ES+): m/z=307 [M−H]; HPLC=99.79%.

Preparation of 2-(4-Formylphenoxy)-N,N-dimethylacetamide (2c)

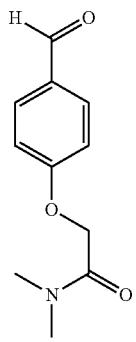

In a similar fashion as general procedure 7, a mixture of ethyl 2-(4-formylphenoxy)acetate 1 (150 mg, 0.72 mmol) and 2M solution of dimethylamine in THF (5 ml, 10 mmol) in ethanol (2 mL) was stirred at room temperature for 12 h. The reaction was monitored by TLC (100% ethyl acetate, $R_f$=0.4). The reaction mixture was concentrated in vacuo to provide the title compound as a pale yellow crude oil 2c (138 mg). The crude compound was used in the next step without further purification. The reaction Preparation of (Z)—N,N-dimethyl-2-(4-((4-oxo-2-thioxothiazolidin-5-ylidene)methyl)phenoxy) acetamide (NADi-188)

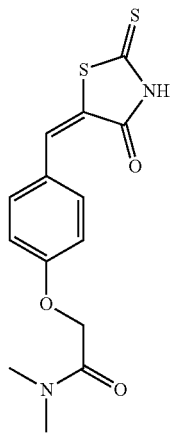 [SMILES: CN(C)C(=O)COc1ccc(/C=C2/SC(=S)NC2=O)cc1]

In a similar fashion as general procedure 3, a mixture of 2-(4-formylphenoxy)-N,N-dimethylacetamide 2c (0.14 mg, 0.84 mmol), 2-thioxothiazolidin-4-one 3 (105 mg, 0.79 mmol) and sodium acetate (88 mg, 1.08 mmol) in acetic acid (5 mL) was heated at 120° C. for 12 h. After workup and purification, the title compound NADi-188 was obtained as a yellow solid (90 mg, 38% yield. $^1$H NMR (400 MHz, DMSO-$d_6$): δ 13.75 (br. s, 1H), 7.61 (s, 1H), 7.55 (d, J=8.82 Hz, 2H), 7.07 (d, J=8.82 Hz, 2H), 4.94 (s, 2H), 3.00 (s, 3H), 2.85 (s, 3H); MS (ES+): m/z=323 [M+H]; HPLC=97.08%.

Example 10

Synthetic Scheme for Targets NADi-201, NADi-202 and NADi-203

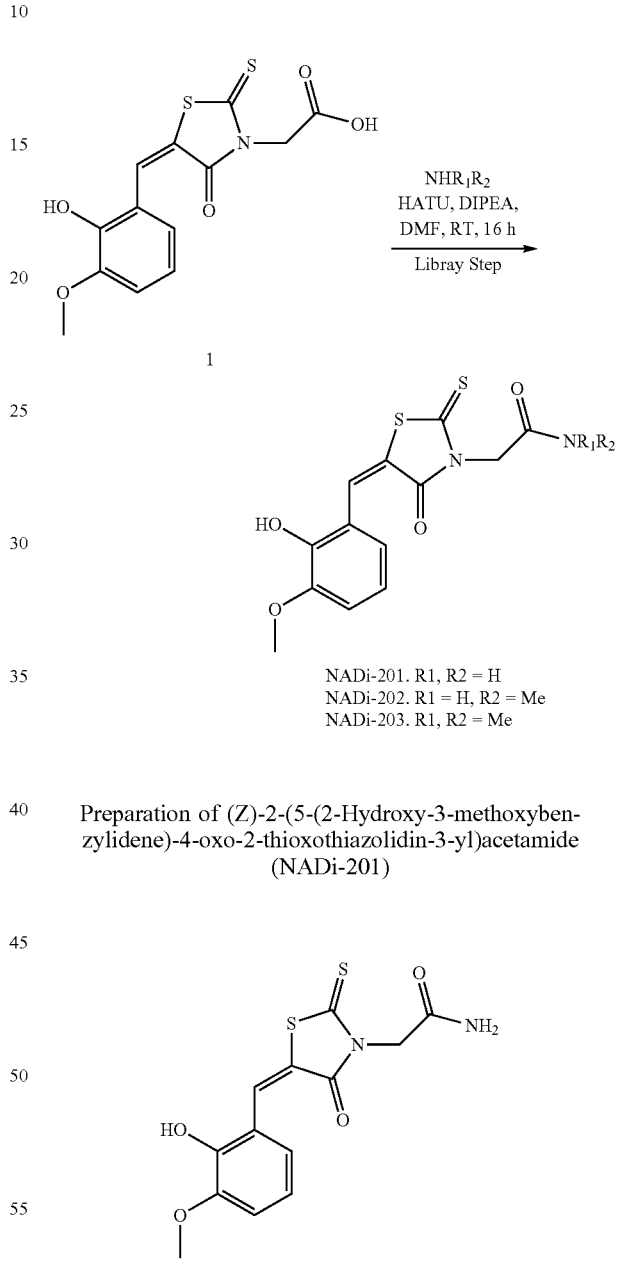

Preparation of (Z)-2-(5-(2-Hydroxy-3-methoxybenzylidene)-4-oxo-2-thioxothiazolidin-3-yl)acetamide (NADi-201)

General Procedure 8:

To a solution of (Z)-2-(5-(2-hydroxy-3-methoxybenzylidene)-4-oxo-2-thioxothiazolidin-3-yl)acetic acid 1 (150 mg, 0.46) in DMF (5 mL) was added NH$_4$Cl (37 mg, 0.69 mmol), HATU (0.263 g, 0.69 mmol) followed by DIPEA (0.35 ml, 2.07 mmol) and the reaction was stirred at room temperature for 16 h. TLC showed completion of reaction. The reaction mixture was diluted with water and stirred for 15 min. The solid precipitate was collected by filtration, washed with water, and dried to afford the titled compound NADi-201 (14 mg, 10%). ¹H NMR (400 MHz, DMSO-d$_6$): δ 9.99 (br. s, 1H), 8.04 (s, 1H), 7.74 (br. s, 1H), 7.31 (br. s, 1H), 7.14 (d, J=7.06 Hz, 1H), 6.88-7.03 (m, 2H), 4.61 (s, 2H), 3.86 (s, 3H); MS (ES+): m/z=325 [M+H]; HPLC=92.80%.

Preparation of (Z)-2-(5-(2-Hydroxy-3-methoxybenzylidene)-4-oxo-2-thioxothiazolidin-3-yl)-N-methylacetamide (NADi-202)

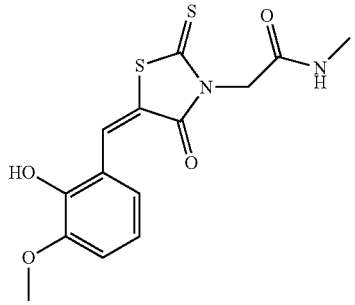 [SMILES: CNC(=O)CN1C(=O)/C(=C\c2cccc(OC)c2O)SC1=S]

In a similar fashion as general procedure 8, a mixture of (Z)-2-(5-(2-hydroxy-3-methoxybenzylidene)-4-oxo-2-thioxothiazolidin-3-yl)acetic acid 1 (200 mg, 0.61 mmol), methylamine (2M in THF, 0.46 ml, 0.72 mmol), HATU (0.280 g, 0.738 mmol) and DIPEA (0.32 ml, 1.84 mmol) in DMF (5 mL) was stirred at room temperature for 16 h. After workup and purification, the title compound was obtained as a yellow solid NADi-202 (50 mg, 24% yield). ¹H NMR (400 MHz, DMSO-d$_6$): δ 9.99 (br. s, 1H), 8.20 (br. s, 1H), 8.04 (s, 1H), 7.18 (d, J=7.06 Hz, 1H), 6.98-7.03 (m, 2H), 4.61 (s, 2H), 3.82 (s, 3H), 2.61 (s, 3H); MS (ES+): m/z=339 [M+H]; HPLC=97.09%.

Preparation of (Z)-2-(5-(2-Hydroxy-3-methoxybenzylidene)-4-oxo-2-thioxothiazolidin-3-yl)-N,N-dimethylacetamide (NADi-203)

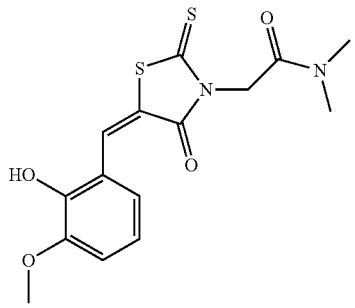 [SMILES: COc1cccc(/C=C2/SC(=S)N(CC(=O)N(C)C)C2=O)c1O]

In a similar fashion as general procedure 8, a mixture of (Z)-2-(5-(2-hydroxy-3-methoxybenzylidene)-4-oxo-2-thioxothiazolidin-3-yl)acetic acid (150 mg, 0.61), N,N-dimethyl amine hydrochloride (56.42 mg, 0.92 mmol), HATU (0.263 g, 0.692 mmol) and DIPEA (0.35 ml, 2.07 mmol) in DMF (5 mL) was stirred at room temperature for 16 h. After workup and purification, the title compound was obtained as a yellow solid NADi-203 (20 mg, 12.5% yield). ¹H NMR (400 MHz, DMSO-d$_6$): δ 10.01 (s, 1H), 8.05 (s, 1H), 7.15 (d, J=7.06 Hz, 1H), 6.91-7.01 (m, 2H), 4.92 (s, 2H), 3.86 (s, 3H), 3.09 (s, 3H), 2.84 (s, 3H); MS (ES+): m/z=353 [M+H]; HPLC=90.80%.

Example 11

Synthetic Scheme for Target NADi-213

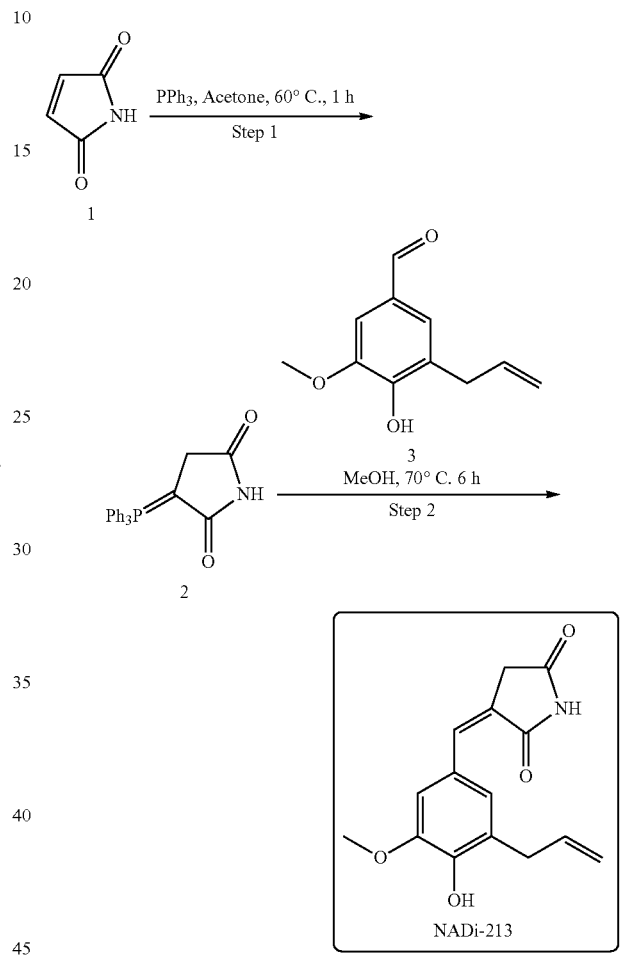

Preparation of 3-(Triphenyl-15-phosphanylidene)pyrrolidine-2,5-dione (2)

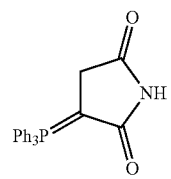

To a solution of 1H-pyrrole-2,5-dione 1 (100 mg, 1.03 mmol) in acetone (10 mL) was added triphenyl phosphine (269 mg, 1.03 mmol) and the reaction was heated under reflux for 2 h. The reaction mixture was cooled to room temperature and the resultant precipitate filtered, washed with acetone and dried to afford 300 mg (83% yield) of the title compound 3 as a white solid. The crude compound was used in the next step without further purification. The compound did not show ionization in LCMS.

Preparation of (Z)-3-(3-Allyl-4-hydroxy-5-methoxy-benzylidene)pyrrolidine-2,5-dione (NADi-213)

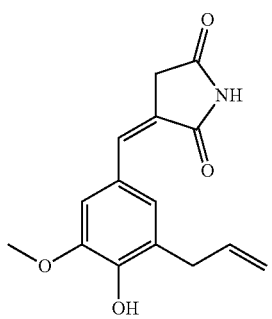 [SMILES: C=CCc1cc(/C=C2/CC(=O)NC2=O)cc(OC)c1O]

To a solution of 3-(triphenyl-15-phosphanylidene)pyrrolidine-2,5-dione 2 (220 mg, 0.61 mmol) in methanol (10 mL) was added 3-allyl-4-hydroxy-5-methoxybenzaldehyde 3 (117 mg, 0.61 mmol) and the reaction mixture was heated to reflux at 70° C. for 6 h. The reaction mixture was concentrated in vacuo. The crude compounds was purified by silica gel column chromatography eluting with 10-15% ethyl acetate in n-hexane to afford 45 mg (28% yield) of NADi-213 as a yellow solid. $^1$H NMR (400 MHz, DMSO-$d_6$) δ=11.30 (br s, 1H), 9.22 (br. s, 1H), 7.27 (s, 1H), 7.06 (s, 1H), 6.97 (s, 1H), 5.82-6.06 (m, 1H), 4.91-5.11 (m, 2H), 3.86 (s, 3H), 3.63 (d, J=2.21 Hz, 2H), 3.34 (s, 2H); HPLC=99.46%.

Example 12

Synthetic Scheme for Target NADi-136

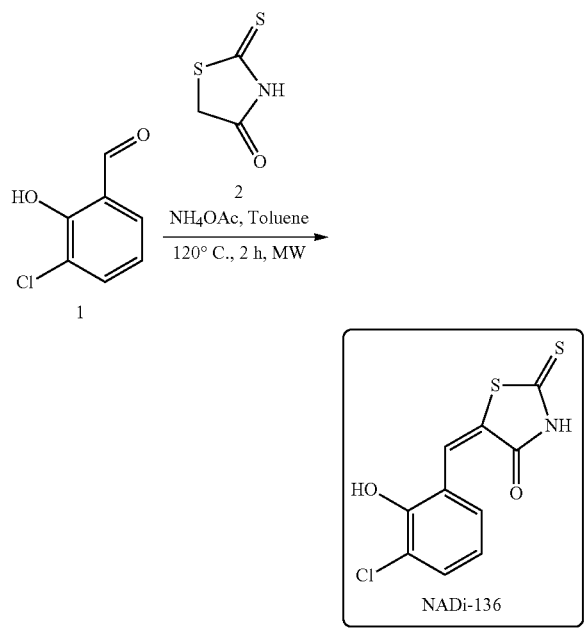

To a solution of 2-hydroxy-3-chlorobenzaldehyde 1 (118 g, 0.75 mmol) in toluene was added 2-thioxothiazolidin-4-one 2 (100 mg, 0.75 mmol) followed by ammonium acetate (116 mg, 1.5 mmol). The reaction mixture was heated in microwave at 120° C. for 2 h. TLC showed the completion of reaction. Water was added and the product was extracted with EtOAc (30 mL×2). The combined organic fractions were washed with brine, dried over anhydrous $Na_2SO_4$ and concentrated in vacuo to afford 45 mg (22% yield) of the title compound NADi-136 as a yellow solid. MS (ES+): m/z=270.00 [M−1]$^+$; $^1$H NMR (400 MHz, DMSO-$d_6$) δ=1H NMR (400 MHz, DMSO-d6) δ ppm 13.81 (brs, 1H), 10.41 (brs, 1H) 7.83 (s, 1H) 7.52 (d, J=7.72 Hz, 1H) 7.31 (d, J=7.94 Hz, 1H) 7.03 (t, J=8 Hz, 1H).

Example 13

Synthetic Scheme for Target NADi-211 and NADi-212

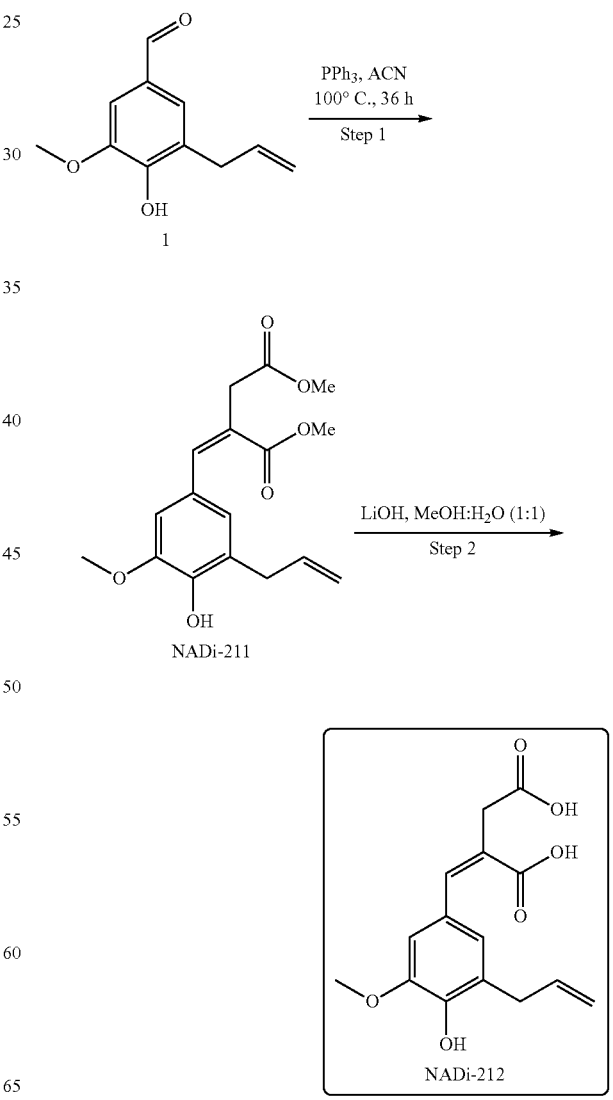

Preparation of Dimethyl (Z)-2-(3-allyl-4-hydroxy-5-methoxybenzylidene)succinate (NADi-211)

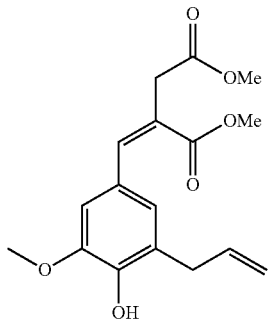 [SMILES: C=CCc1cc(/C=C(/CC(=O)OC)C(=O)OC)cc(OC)c1O]

To a solution of 3-allyl-4-hydroxy-5-methoxybenzaldehyde 1 (150 mg, 1.03 mmol) and dimethyl maleate (0.15 g, 0.78 mmol) in acetonitrile (5 mL) was added triphenyl phosphine (200 mg, 0.78 mmol). The reaction was heated in seal tube at 100° C. for 36 h. The reaction was monitored by TLC. After completion of the reaction, the mixture was concentrated in vacuo. The crude product obtained was purified by flash column chromatography to give 70 mg (28% yield) of title compound as yellow oil. MS (ES+): m/z=319.95 [M−1]$^+$; $^1$H NMR (400 MHz, DMSO-d$_6$) δ=7.82 (s, 1 H) 6.82 (d, J=15.44 Hz, 2 H) 5.97 (m, 1 H) 5.88 (s, 1 H) 5.03-5.14 (m, 2 H) 3.88 (s, 3 H) 3.82 (s, 3 H) 3.73 (s, 3 H) 3.59 (s, 2 H) 3.40 (d, J=6.17 Hz, 2 H)

Preparation of (Z)-2-(3-allyl-4-hydroxy-5-methoxybenzylidene)succinic acid (NADi-212)

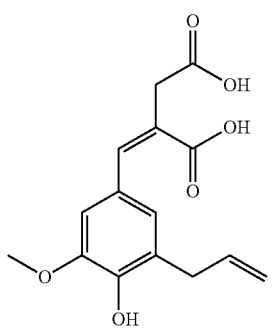 [SMILES: C=CCc1cc(/C=C(/CC(=O)O)C(=O)O)cc(OC)c1O]

To a solution of dimethyl (Z)-2-(3-allyl-4-hydroxy-5-methoxybenzylidene)succinate NADi-211 (70 mg, 0.218 mmol) in methanol (5 mL) was added a solution of LiOH (27.6 mg, 0.65 mmol) in water (5 mL). The reaction mixture was stirred at room temperature for 1 h. The methanol was evaporated and the reaction mixture was extracted with diethyl ether to remove any impurities formed. The aqueous fraction was acidified with 1N HCl and the mixture was extracted with EtOAc (30 mL×2). The combined organic fractions were washed with brine, dried over anhydrous Na$_2$SO$_4$ and concentrated in vacuo to afford 25 mg (39% yield) of title compound NADi-212 as an off-white solid. MS (ES+): m/z=291 [M−1]$^+$; $^1$H NMR (400 MHz, DMSO-d$_6$) δ 12.40 (brs, 2H) 9.05 (s, 1H) 7.64 (s, 1H) 6.94 (s, 1H), 6.79 (s, 1H), 5.92 (m, 1H) 4.88-5.14 (m, 2H) 3.8 (s, 3H) 3.42 (s, 2H) (2H's merged in solvent peak).

Example 13

Synthetic Scheme for Target NADi-226

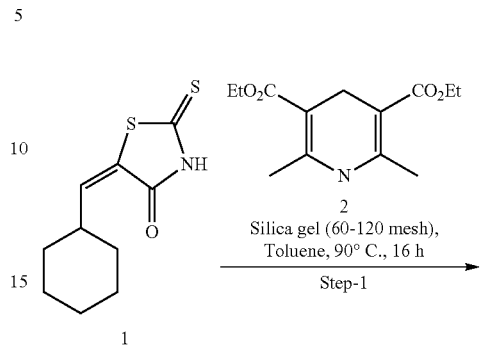

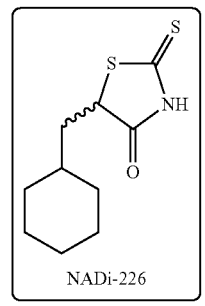

5-(Cyclohexylmethyl)-2-thioxothiazolidin-4-one (NADi-226)

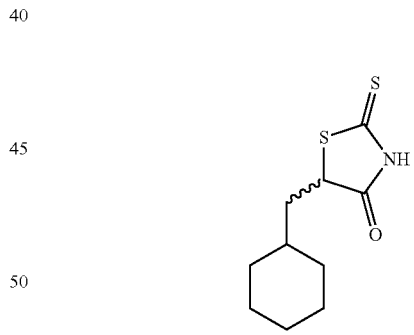

To a solution of (Z)-5-(cyclohexylmethylene)-2-thioxothiazolidin-4-one 1 (100 mg, 0.44 mmol) in toluene was added silica gel (60-120 mesh) (632 mg, 0.63 mmol) and ethidine 2 (208 mg, 0.82 mmol) at room temperature. The resulting solution was stirred at 90° C. for 16 h. The reaction mixture was concentrated in vacuo resulting in a crude compound which was purified using combiflash column chromatography to afford 40 mg (40% yield) of NADi-226 as yellow solid. $^1$H NMR (400 MHz, DMSO-d$_6$) δ 13.18 (br. s, 1 H), 4.70 (dd, J=4.62, 10.17 Hz, 1 H), 1.89-2.01 (m, 1 H), 1.55-1.79 (m, 7 H), 1.34 (d, J=2.31 Hz, 1 H), 1.06-1.25 (m, 4 H); MS (ES+): m/z=227.9 [M−H]; HPLC=98.40%.

Example 14

Synthetic Scheme for Target NADi-232 and 236

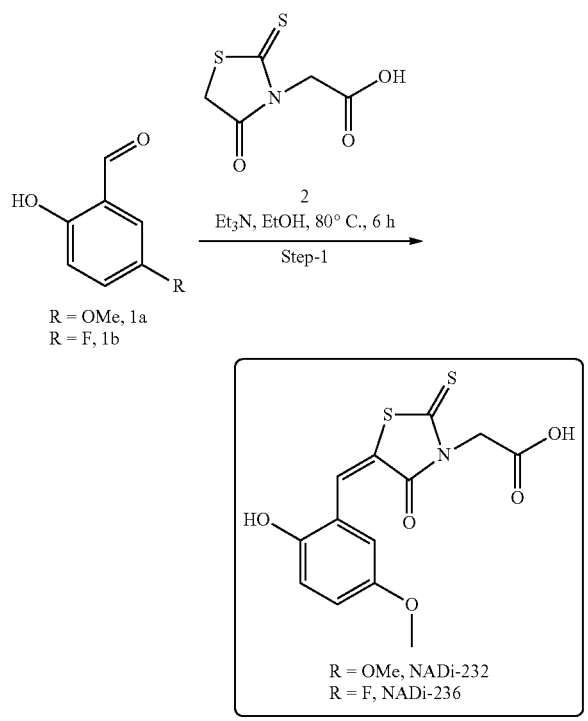

(Z)-2-(5-(2-Hydroxy-5-methoxybenzylidene)-4-oxo-2-thioxothiazolidin-3-yl)acetic acid (NADi-232)

General Procedure 9:

To a solution of 2-hydroxy-5-methoxybenzaldehyde 1a (1.19 g, 7.84 mmol) in ethanol was added 2-(4-oxo-2-thioxothiazolidin-3-yl)acetic acid 2 (1.5 g, 7.84 mmol) and triethyl amine (2.2 mL, 15.69 mmol) at room temperature. The resulting solution was heated to reflux at 80° C. for 6 h. The reaction mixture was allowed to attain room temperature and concentrated in vacuo to dryness resulting in crude compound which was washed with water. The crude compound after aqueous wash was purified by recrystallization in acetonitrile to afford 550 mg (21% yield) of NADi-232 as yellow solid. $^1$H NMR (400 MHz, DMSO-$d_6$) δ 10.52 (br. s, 1 H), 7.97 (s, 1 H), 6.99 (d, J=2.79 Hz, 1 H), 6.94 (s, 1 H), 6.92 (s, 1 H), 6.84 (d, J=2.79 Hz, 1 H), 4.61 (s, 2 H), 3.75 (s, 3 H); MS (ES+): m/z=347.85 [M+Na]; HPLC=99.68%.

(Z)-2-(5-(5-Fluoro-2-hydroxybenzylidene)-4-oxo-2-thioxothiazolidin-3-yl)acetic acid (NADi-236)

In a similar fashion using general procedure 9, 5-fluoro-2-hydroxybenzaldehyde 1b (1.1 g, 7.84 mmol), 2-(4-oxo-2-thioxothiazolidin-3-yl)acetic acid 2 (1.5 g, 7.84 mmol) and triethyl amine (2.2 mL, 15.96 mmol) at 80° C. for 6 h gave the title compound NADi-236 as yellow solid (730 mg, 29% yield). $^1$H NMR (400 MHz, DMSO-$d_6$) δ 13.52 (br. s, 1 H), 10.90 (br. s, 1 H), 7.94 (s, 1 H), 7.22-7.28 (m, 1 H), 7.19 (dd, J=2.77, 9.25 Hz, 1 H), 6.98 (dd, J=4.86, 9.02 Hz, 1 H), 4.72 (s, 2 H); MS (ES+): m/z=337 [M+Na]; HPLC=99.93%.

Example 15

Synthetic Scheme for Target NADi-235

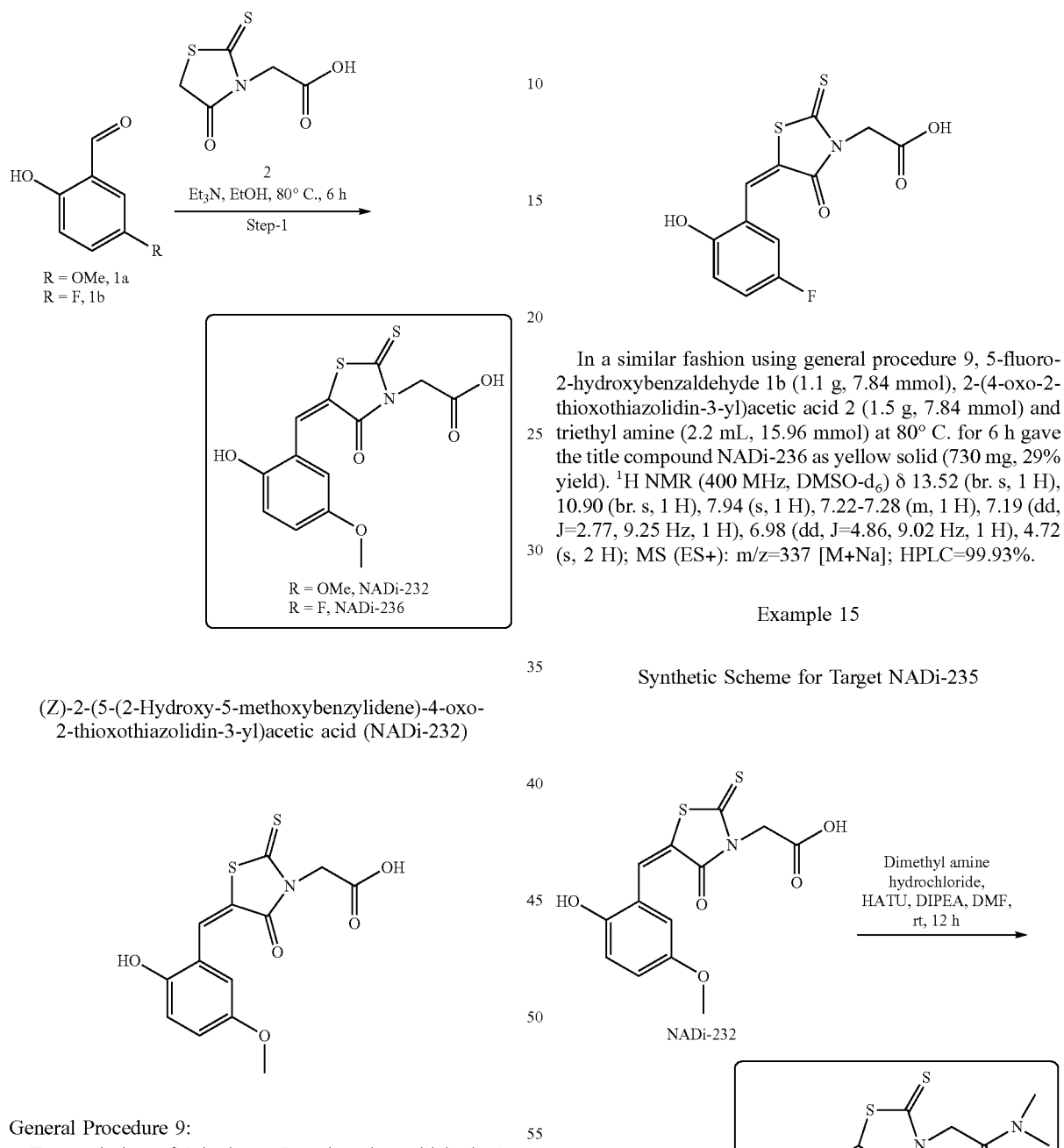

153

(Z)-2-(5-(2-Hydroxy-5-methoxybenzylidene)-4-oxo-2-thioxothiazolidin-3-yl)-N,N-dimethylacetamide (NADi-235)

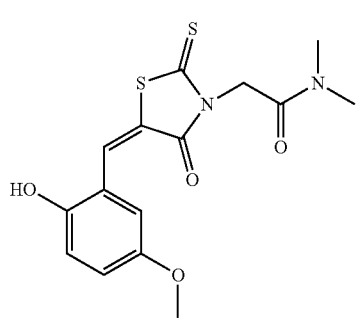 [SMILES: COc1ccc(O)c(/C=C2/SC(=S)N(CC(=O)N(C)C)C2=O)c1]

154

(Z)-2-(5-(5-Fluoro-2-hydroxybenzylidene)-4-oxo-2-thioxothiazolidin-3-yl)acetamide (NADi-237)

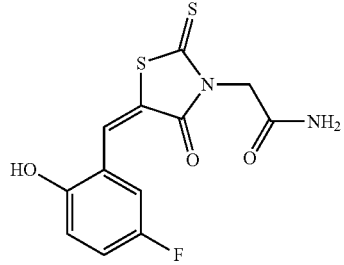 [SMILES: NC(=O)CN1C(=O)/C(=C\c2cc(F)ccc2O)SC1=S]

General Procedure 10:

To a solution of (Z)-2-(5-(2-hydroxy-5-methoxybenzylidene)-4-oxo-2-thioxothiazolidin-3-yl)acetic acid NADi-232 (150 mg, 0.46 mmol) in DMF (3 mL) was added dimethyl amine hydrochloride (56 mg, 0.69 mmol), DIPEA (0.2 mL, 1.38 mmol) and HATU (210 mg, 0.55 mmol) and stirred at room temperature for 12 h. The reaction mixture was diluted with water and stirred for 15 min. The solid precipitated out was collected by filtration and washed with diethyl ether and acetonitrile and dried in vacuo to afford 22 mg (13% yield) of NADi-235 as yellow solid. $^1$H NMR (400 MHz, DMSO-$d_6$) δ 10.35 (s, 1 H), 7.98 (s, 1 H), 7.00-7.05 (m, 1 H), 6.94 (s, 1 H), 6.86 (d, J=2.77 Hz, 1 H), 4.92 (s, 2 H), 3.76 (s, 3 H), 3.09 (s, 3 H), 2.84 (s, 3 H); MS (ES+): m/z=352.9 [M+H]; HPLC=94.26%.

In a similar fashion using general procedure 10, (Z)-2-(5-(5-fluoro-2-hydroxybenzylidene)-4-oxo-2-thioxothiazolidin-3-yl)acetic acid NADi-236 (150 mg, 0.47 mmol), ammonium chloride 2a (38 mg, 0.72 mmol), DIPEA (0.25 mL, 0.72 mmol) and HATU (218 mg, 0.72 mmol) at room temperature for 12 h furnished 15 mg (10% yield) of NADi-237 as yellow solid. $^1$H NMR (400 MHz, DMSO-$d_6$) δ 10.81 (s, 1 H), 7.91 (s, 1 H), 7.73 (br. s, 1 H), 7.31 (br. s, 1 H), 7.24 (dt, J=2.77, 8.55 Hz, 1 H), 7.17 (dd, J=2.77, 9.25 Hz, 1 H), 6.98 (dd, J=4.86, 9.02 Hz, 1 H), 4.61 (s, 2 H); MS (ES+): m/z=311 [M−H]; HPLC=95.84%.

Example 16

Synthetic Scheme for Target NADi-237, 238 and 239

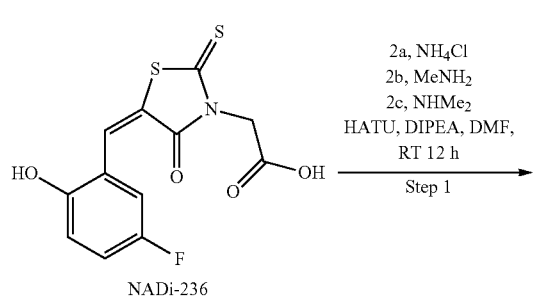

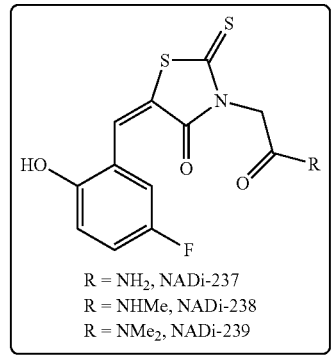

(Z)-2-(5-(5-Fluoro-2-hydroxybenzylidene)-4-oxo-2-thioxothiazolidin-3-yl)-N-methylacetamide (NADi-238)

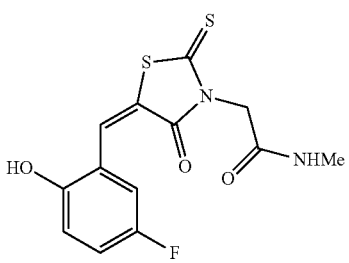 [SMILES: CNC(=O)CN1C(=O)/C(=C\c2cc(F)ccc2O)SC1=S]

In a similar fashion using general procedure 10, (Z)-2-(5-(5-fluoro-2-hydroxybenzylidene)-4-oxo-2-thioxothiazolidin-3-yl)acetic acid NADi-236 (150 mg, 0.47 mmol), methyl amine 2b (48 mg, 0.72 mmol), DIPEA (0.25 mL, 0.72 mmol) and HATU (218 mg, 0.72 mmol) at room temperature for 12 h afforded 45 mg (29% yield) of NADi-238 as yellow solid. $^1$H NMR (400 MHz, DMSO-$d_6$) δ 10.82 (br. s, 1 H), 8.18 (br. s, 1 H), 7.91 (s, 1 H), 7.25 (dt, J=3.01, 8.44 Hz, 1 H), 7.17 (dd, J=3.01, 9.48 Hz, 1 H), 6.98 (dd, J=4.86, 9.02 Hz, 1 H), 4.62 (s, 2 H), 2.60 (d, J=4.62 Hz, 3 H); MS (ES+): m/z=324.95 [M−H]; HPLC=94.49%.

155

(Z)-2-(5-(5-Fluoro-2-hydroxybenzylidene)-4-oxo-2-thioxothiazolidin-3-yl)-N,N-dimethylacetamide (NADi-239)

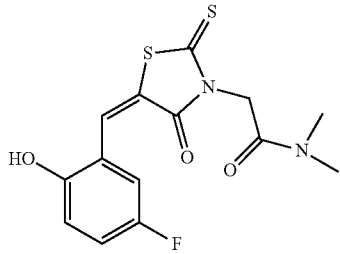 [SMILES: CN(C)C(=O)CN1C(=O)/C(=C\c2cc(F)ccc2O)SC1=S]

In a similar fashion using general procedure 10, (Z)-2-(5-(5-fluoro-2-hydroxybenzylidene)-4-oxo-2-thioxothiazolidin-3-yl)acetic acid NADi-236 (150 mg, 0.47 mmol), dimethyl amine hydrochloride 2c (58 mg, 0.72 mmol), DIPEA (0.25 mL, 0.72 mmol) and HATU (218 mg, 0.72 mmol) at room temperature for 12 h gave 14 mg (9% yield) of NADi-239 as yellow solid. $^1$H NMR (400 MHz, DMSO-$d_6$) δ 10.81 (s, 1 H), 7.91 (s, 1 H), 7.24 (dt, J=2.77, 8.55 Hz, 1 H), 7.17 (dd, J=2.77, 9.25 Hz, 1 H), 6.97 (dd, J=4.86, 9.02 Hz, 1 H), 4.92 (s, 2 H), 3.09 (s, 3 H), 2.84 (s, 3 H); MS (ES+): m/z=340.80 [M+H]; HPLC=94.81%.

Example 17

Synthetic Scheme for Target NADi-241

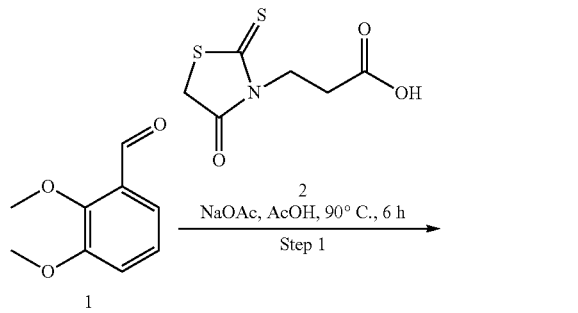

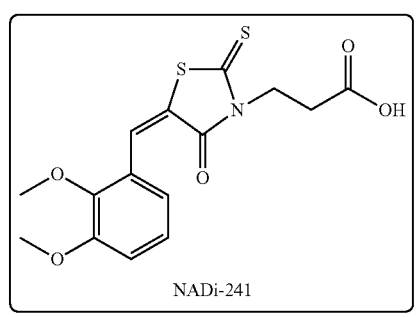

156

(Z)-3-(5-(2,3-Dimethoxybenzylidene)-4-oxo-2-thioxothiazolidin-3-yl)propanoic acid (NADi-241)

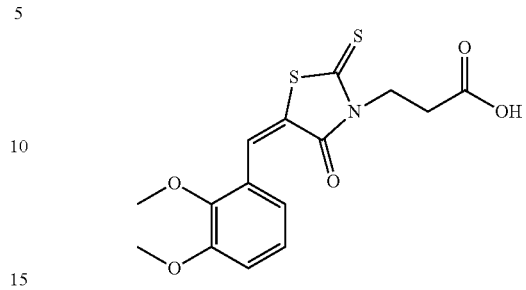

To a solution of 2,3-dimethoxybenzaldehyde 1 (200 mg, 1.20 mmol) and 3-(4-oxo-2-thioxothiazolidin-3-yl)propanoic acid 2 (247 mg, 1.20 mmol) in glacial acetic acid (4 mL) was added sodium acetate (197 mg, 2.41 mmol) and the reaction was heated at 90° C. for 6 h. After the completion of reaction (as monitored by LCMS) the reaction mixture was poured into ice cooled water, stirred for 15 min and the solid precipitated out was filtered, washed with diethyl ether and dried in vacuo to afford 235 mg (55% yield) of NADi-241 as yellow solid. $^1$H NMR (400 MHz, DMSO-$d_6$) δ 12.50 (s, 1 H), 7.89 (s, 1 H), 7.25 (d, J=1.87 Hz, 2 H), 7.06 (dd, J=3.74, 5.62 Hz, 1 H), 4.20-4.26 (m, 2 H), 3.86 (s, 3 H), 3.82 (s, 3 H), 2.61-2.66 (m, 2 H); MS (ES+): m/z=353.90 [M+H]; HPLC=99.28%.

Determination of Equilibrium Dissociation Constants ($K_D$) and Half Maximal Inhibitory Concentrations ($IC_{50}$)

The inhibitors described herein were subjected to surface plasmon resonance ("SPR") to determine their binding constants to the NICD and CSL components of the NTC. In particular, the target protein (NICD1) was immobilized on the dextran surface of the SPR sensor chip. Through a microflow system, a solution with the inhibitor was injected over the immobilized protein layer. The inhibitor bound to the immobilized protein, which led to an increase in SPR signal, indicating association of the ligand to the target protein. After 45 seconds, buffer solution was injected on the microfluidics that dissociated the bound complex between the ligand and the inhibitor. As the inhibitor dissociated from the ligand, a decrease in SPR signal was observed. The equilibrium dissociation constant $K_D$ was determined by plotting the equilibrium response (Req) as a function of the concentration of the ligand, and fitting the data to a 1:1 binding model. The results are listed in Error! Reference source not found.

| Compound ID | $K_D$ (µM) NICD | $K_D$ (µM) CSL | $IC_{50}$ (µM) |
|---|---|---|---|
| 1-134 | 17 ± 5 | 15 ± 3 | 6.0 |
| 1-134-83 | 11 ± 3 | 8 ± 2 | 26.0 |
| 1-134-02 | 2.9 ± 0.6 | 3.6 ± 0.9 | 0.5 |
| NADi-239 | 3.7 ± 0.8 | 13 ± 2 | 0.5 |
| NADi-203 | 5.7 ± 0.9 | 6.4 ± 0.7 | 0.5 |
| NADi-090 | 25 ± 4 | 3.4 ± 0.7 | 0.07 |

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step not specifically disclosed.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference.

We claim:

1. A method of inhibiting the Notch transcriptional activation complex ("NTC") in a cell, comprising contacting the cell with a compound of Formula (I), or a pharmaceutically acceptable salt thereof, in an amount effective to inhibit the NTC:

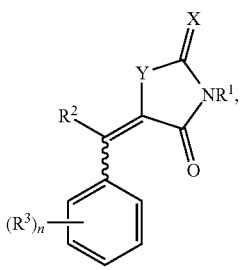
(I)

wherein
~~~ represents a bond that results in the adjacent double bond being in either the E or Z configuration;
n is 0, 1, 2, 3, or 4;
X is O or S;
Y is O, S, NH, or $NC_{1-3}$ alkyl;
$R^1$ is selected from the group consisting of H, $C_{1-6}$ alkyl, $C_{1-6}$ alkenyl, $C_{0-6}$ alkylene—$COR^9$, NH-aryl, NH—(C=O)-aryl, $C_{0-6}$ alkylene-cycloalkyl, $C_{0-6}$ alkylene-heterocycloalkyl, $C_{0-6}$ alkylene-heterocycloalkenyl, $C_{0-6}$ alkylene-aryl, $C_{1-6}$ alkylene—$SO_2R^5$, $C_{1-6}$ alkylene-$R^5$, and $C_{0-6}$ alkylene-heteroaryl;
$R^2$ is H or $C_{1-3}$ alkyl;
each $R^3$ is independently selected from the group consisting of $OR^4$, $COOR^4$, $NO_2$, halo, $SO_2R^5$, $C_{1-6}$ alkyl, $C_{1-6}$ alkenyl, $C_{0-6}$ alkylene-cycloalkyl, $C_{0-6}$ alkylene-aryl, $C_{0-6}$ alkylene-heteroaryl, and (C=O)N($R^7$)$_2$;
$R^4$ is selected from the group consisting of H, $C_{1-6}$ alkyl, $C_{1-6}$ alkenyl, $C_{1-6}$ alkynyl, $C_{0-6}$ alkylene-(C=O)$R^8$, $C_{1-6}$ alkylene-N($R^6$)$_2$, $C_{1-6}$ alkylene-CN, $C_{0-6}$ alkylene-aryl, $C_{0-6}$ alkylene-heteroaryl, $C_{1-6}$ alkylene-O-aryl, $C_{1-6}$ alkylene-S-aryl, $C_{1-6}$ alkylene-$NR^6$-aryl, and $C_{1-6}$ alkylene-$NR^6$-heteroaryl;
$R^5$ is OH, N($R^6$)$_2$, NH(C=O)$C_{1-3}$ alkyl, or NH(C=O) aryl;
each $R^6$ is independently H, $C_{1-3}$ alkyl;
each $R^7$ is independently H, $C_{1-3}$ alkyl, $SO_2H$; or $SO_2$($C_{1-3}$ alkyl);
$R^8$ is $C_{1-6}$ alkyl, aryl, $OC_{1-6}$ alkyl, or N($R^6$)$_2$; and
$R^9$ is OH, N($R^6$)$_2$, $NHSO_2R^6$, $SO_2N(R^6)_2$.

2. The method of claim 1, wherein $R^2$ is H.
3. The method of claim 1, wherein X is S.
4. The method of claim 1, wherein Y is: (a) NH or $NC_{1-3}$ alkyl; or (b) O.
5. The method of claim 1, wherein Y is S.
6. The method of claim 1, wherein the compound comprises Formula (Ia), or a pharmaceutically acceptable salt thereof:

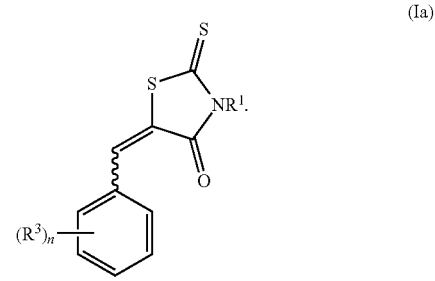
(Ia)

7. The method of claim 1, wherein $R^1$ is $C_{1-6}$ alkyl, $C_{1-6}$ alkenyl, $C_{0-6}$ alkylene-$COR^9$, $C_{0-6}$ alkylene-cycloalkyl, $C_{0-6}$ alkylene-heterocycloalkenyl, $C_{1-6}$ alkylene-$SO_2R^5$, or $C_{1-6}$ alkylene-$R^5$.
8. The method of claim 1, wherein $R^1$ is NH-aryl, NH—(C=O)-aryl, $C_{0-6}$ alkylene-heterocycloalkyl, $C_{0-6}$ alkylene-aryl, or $C_{0-6}$ alkylene-heteroaryl.
9. The method of claim 1, wherein $R^1$ is H.
10. The method of claim 1, wherein n is 1, 2, or 3.
11. The method of claim 1, wherein at least one $R^3$ is $OR^4$; and $R^4$ optionally is: (a) H, $C_{1-6}$ alkyl, $C_{1-6}$ alkenyl, or $C_{1-6}$ alkynyl; (b) $C_{1-6}$ alkylene-(C=O)$R^8$; or (c) $C_{1-6}$ alkylene-N($R^6$)$_2$, $C_{1-6}$ alkylene-CN, $C_{0-6}$ alkylene-cycloalkyl, $C_{0-6}$ alkylene-aryl, $C_{0-6}$ alkylene-heteroaryl, $C_{1-6}$ alkylene-O-aryl, $C_{1-6}$ alkylene-S-aryl, $C_{1-6}$ alkylene-$NR^6$-aryl, or $C_{1-6}$ alkylene-$NR^6$-heteroaryl; and $R^8$ optionally is (a) $C_{1-6}$ alkyl, or aryl; or (b) $OC_{1-6}$ alkyl or N($R^6$)$_2$.
12. The method of claim 1, wherein at least one $R^3$ is (a) selected from the group consisting of halo, $C_{1-6}$ alkyl, $C_{1-6}$ alkenyl, $C_{0-6}$ alkylene-aryl, and $C_{0-6}$ alkylene-heteroaryl; or (b) COOH, $NO_2$, $SO_2R^5$, or (C=O)N($R^7$)$_2$.
13. The method of claim 1, wherein n is 2 or 3, and each $R^3$ is $OR^4$ or halo.
14. The method of claim 13, wherein: (a) one $R^3$ is OH, and one $R^3$ is $OC_{1-6}$ alkyl or halo; or (b) n is 2, one $R^3$ is OH, and the other $R^3$ is $OC_{1-6}$ alkyl.
15. The method of claim 1, wherein the compound comprises Formula (Ib), or a pharmaceutically acceptable salt thereof:

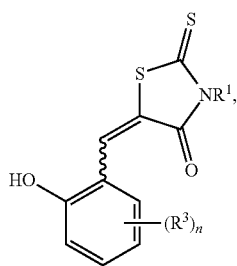
(Ib)
wherein n is 1 or 2; optionally wherein n is 1, $R^3$ is $OC_{1-6}$ alkyl, and $R^3$ is para to the hydroxyl substituent.
16. A method of inhibiting the Notch transcriptional activation complex ("NTC") in a cell, comprising contacting the cell with a compound, or a pharmaceutically acceptable salt thereof, selected from the group consisting of:
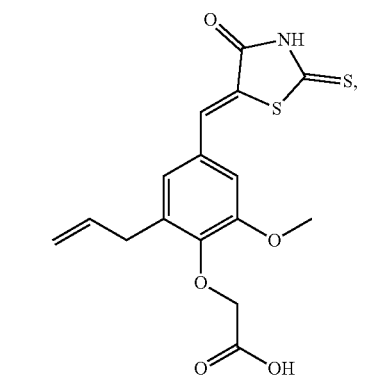
1-134
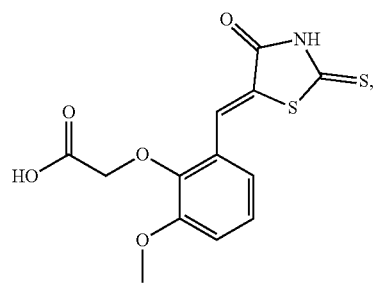
1-134-01
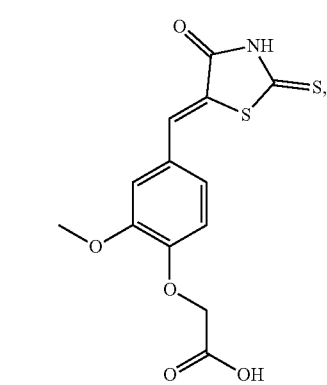
1-134-02
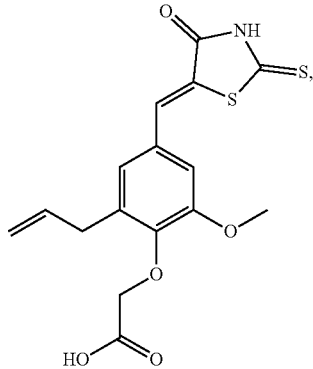
1-134-03
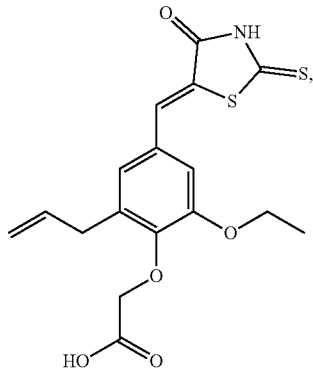
1-134-04
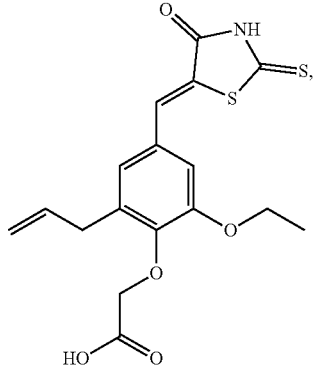
1-134-06
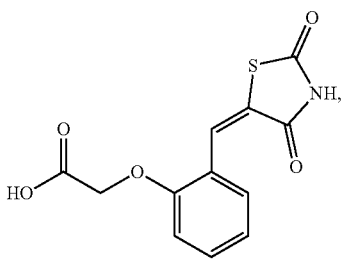
1-134-07
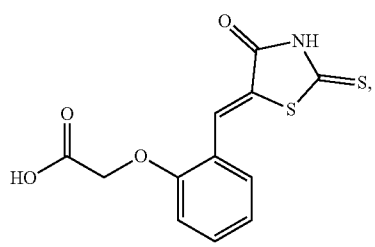
1-134-09

-continued
1-134-10
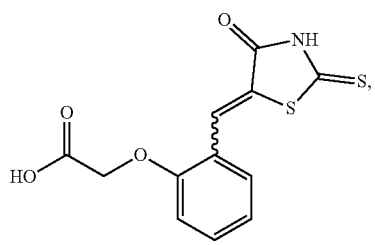
1-134-13
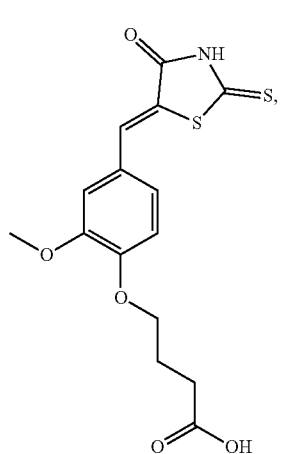
1-134-20
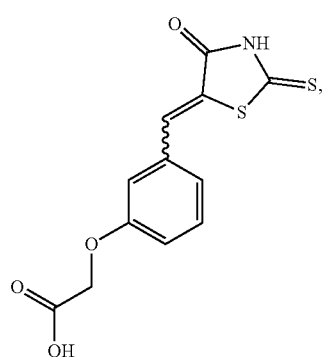
1-134-22
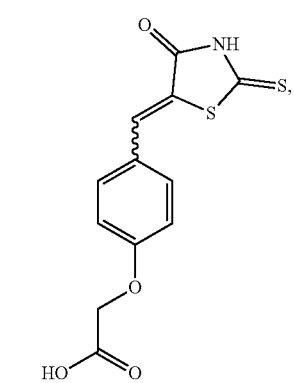
-continued
1-134-24
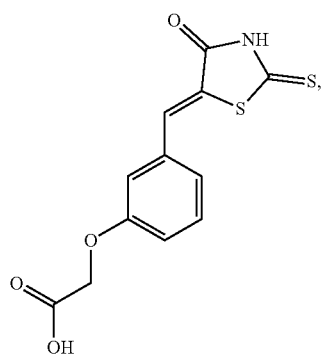
1-134-25
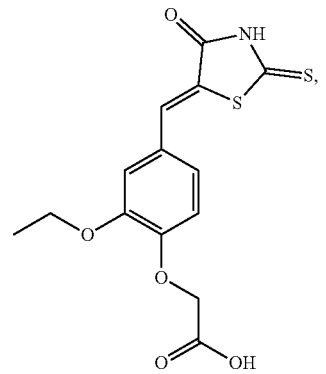
1-134-26
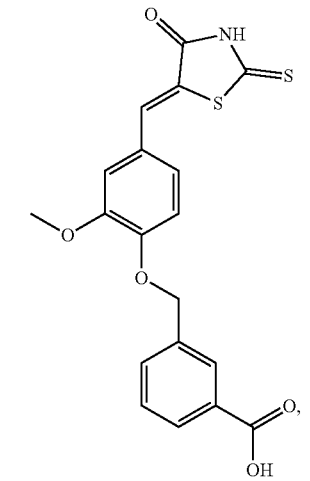
1-134-27
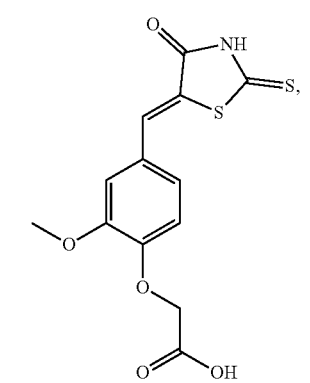

1-134-29
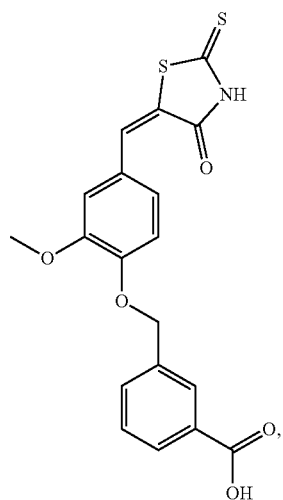
1-134-31
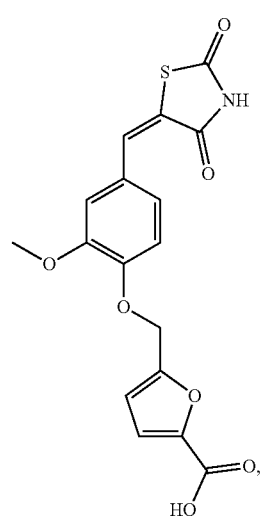
1-134-32
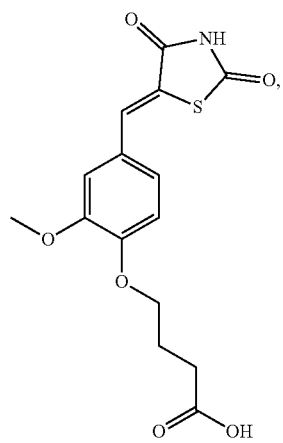
1-134-36
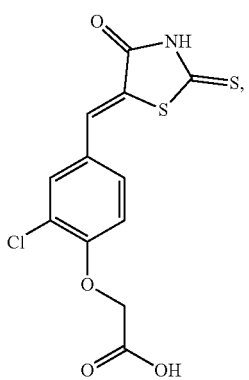
1-134-37
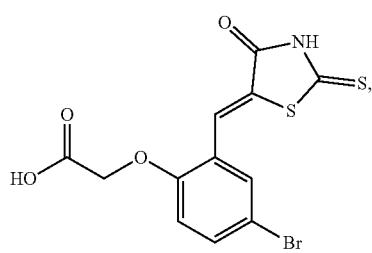
1-134-38
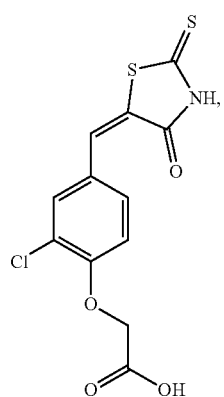
1-134-39
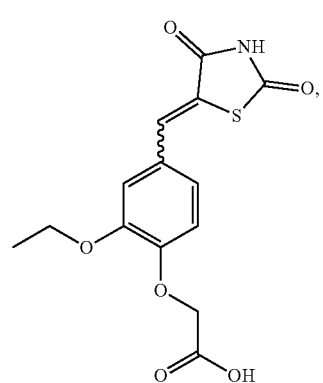

1-134-40
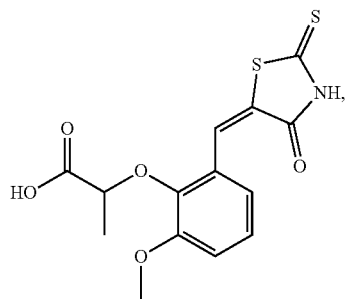
1-134-44
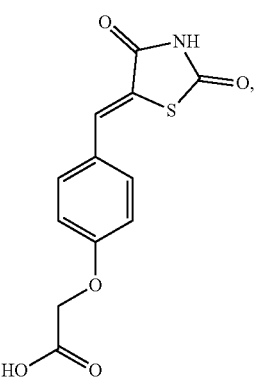
1-134-45
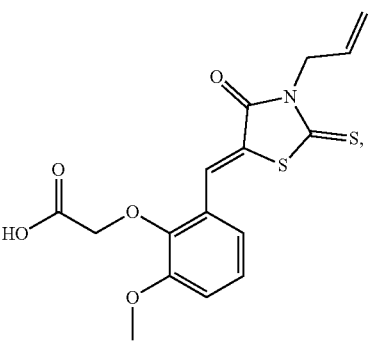
1-134-46
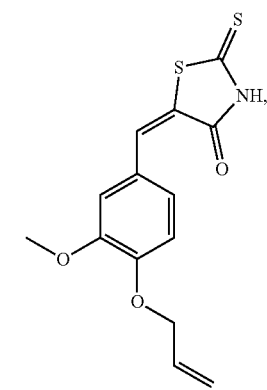
1-134-48
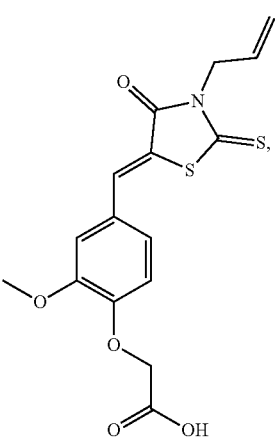
1-134-49
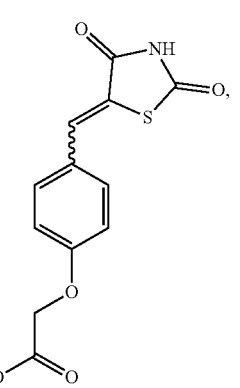
1-134-52
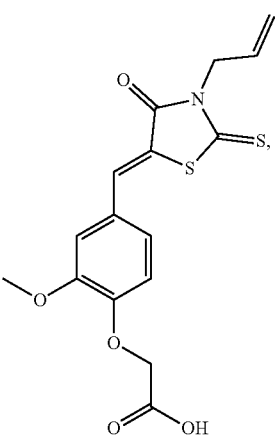
1-134-57
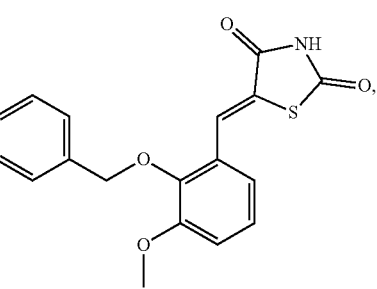

-continued
1-134-59
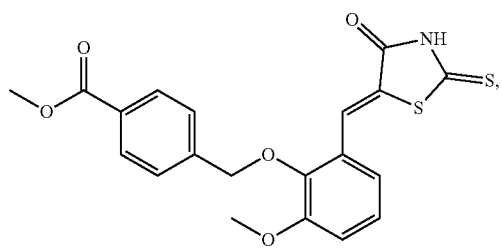
1-134-60
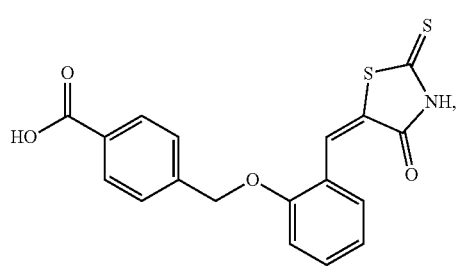
1-134-61
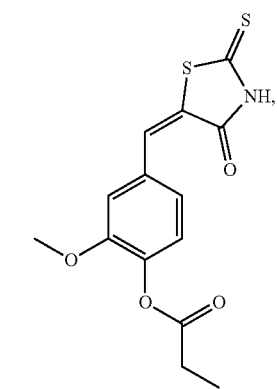
1-134-63
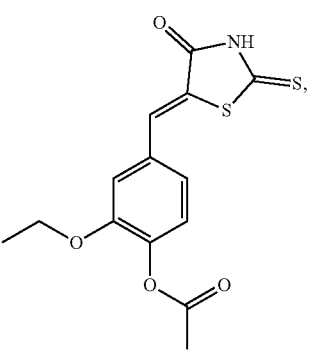
-continued
1-134-64
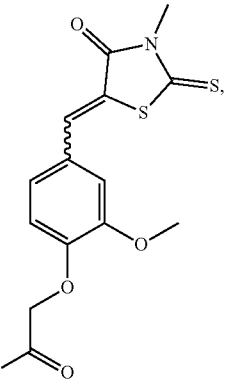
1-134-65
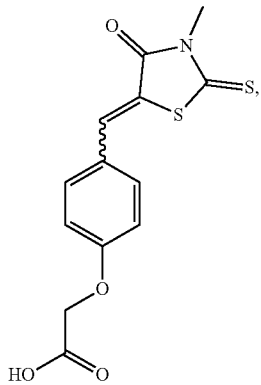
1-134-66
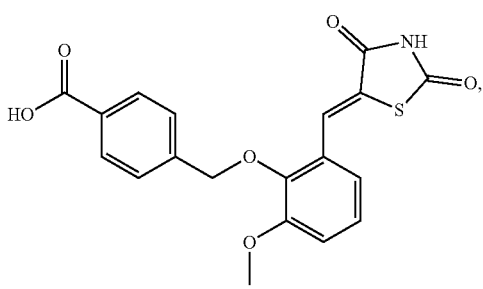
1-134-71
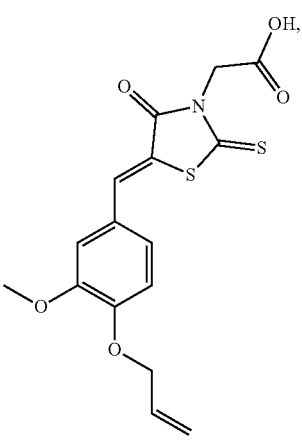

1-134-74
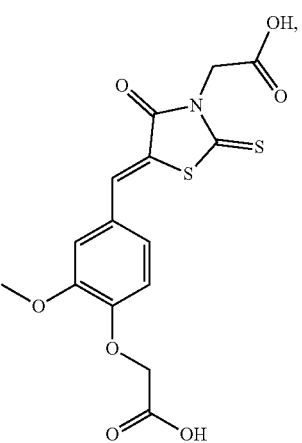
1-134-78
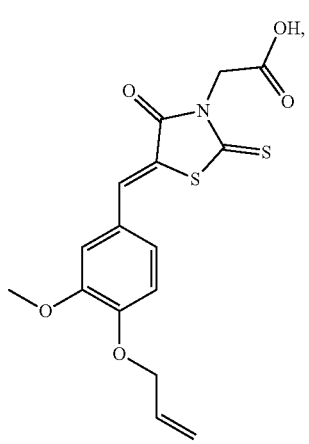
1-134-80
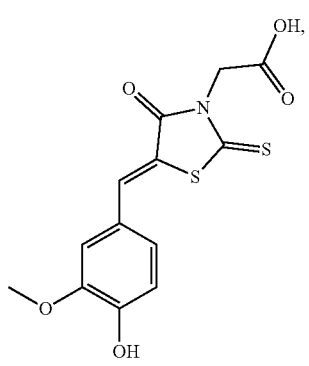
1-134-81
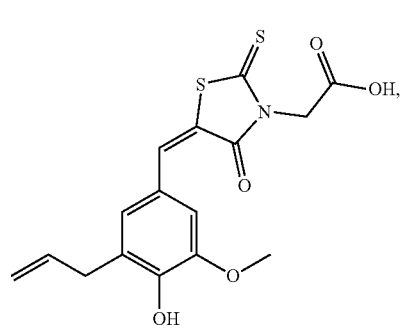
1-134-82
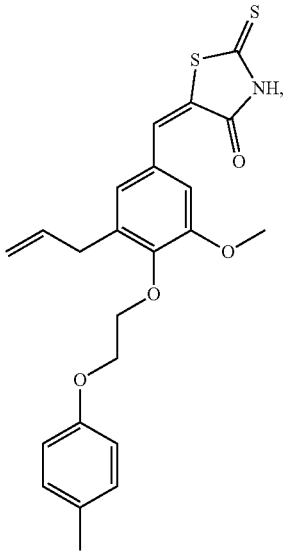
1-134-83
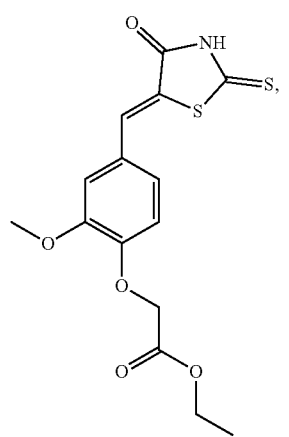
1-134-84
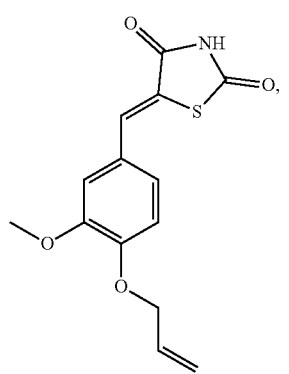

1-134-87
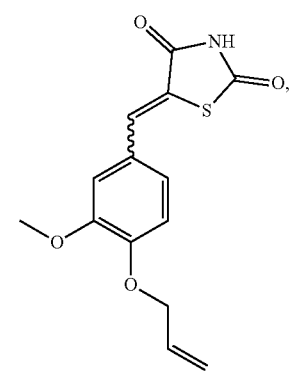
1-134-88
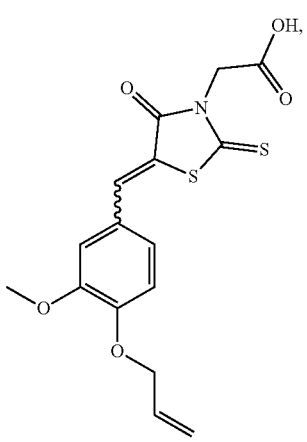
1-134-90
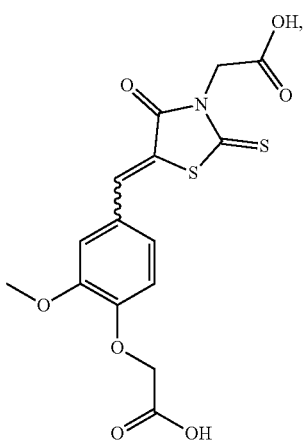
1-134-91
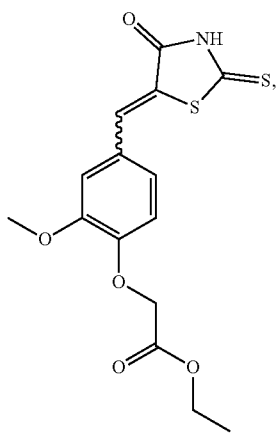
1-134-97
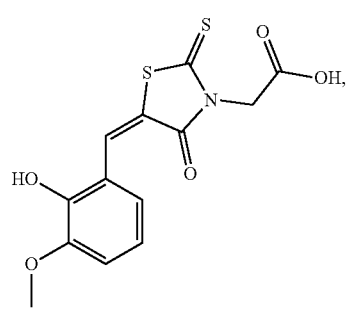
1-134-99
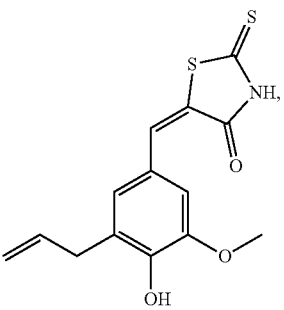
NADi-003
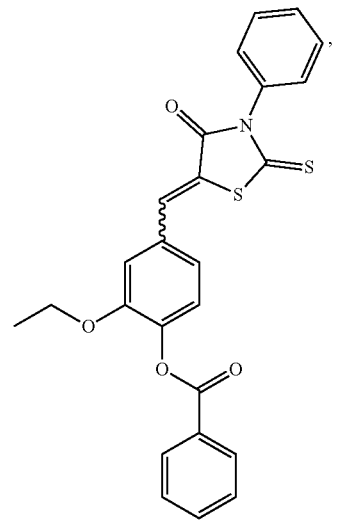

NADi-004
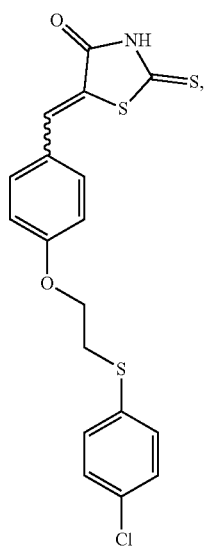
NADi-007
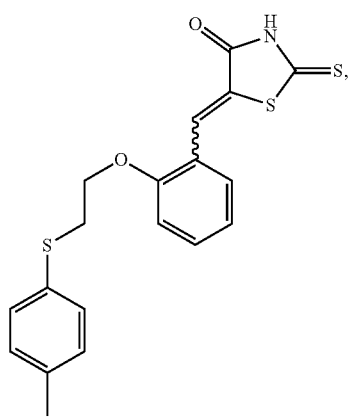
NADi-008
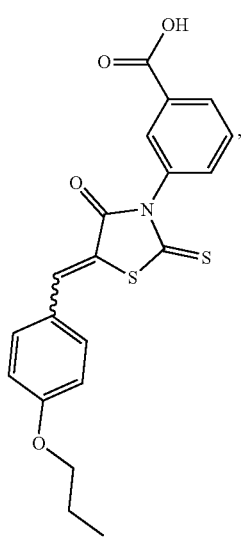
NADi-010
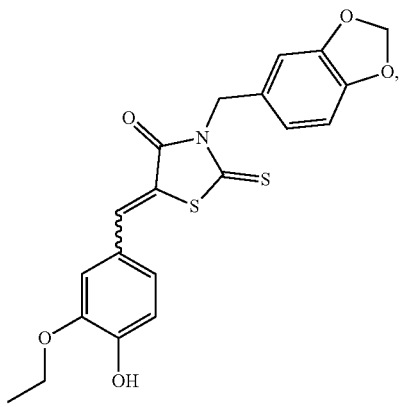
NADi-011
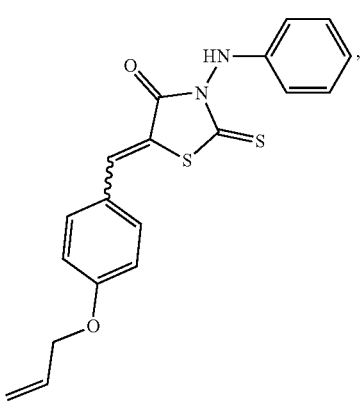
NADi-012
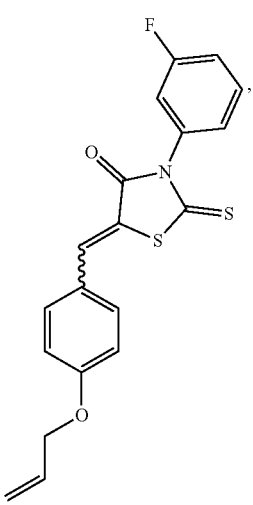

175
-continued
176
-continued
NADi-013
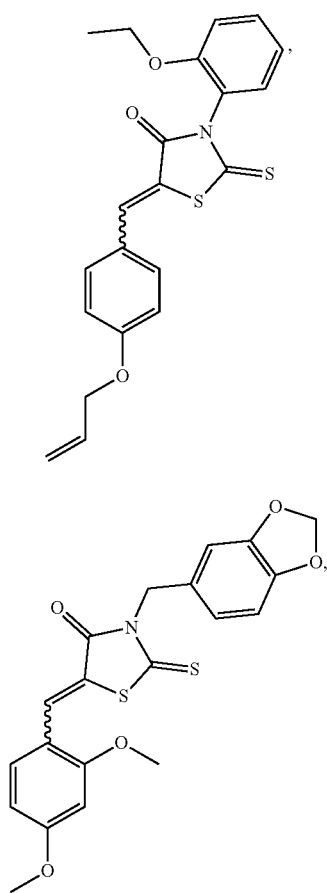
NADi-014
NADi-015
NADi-016
NADi-017
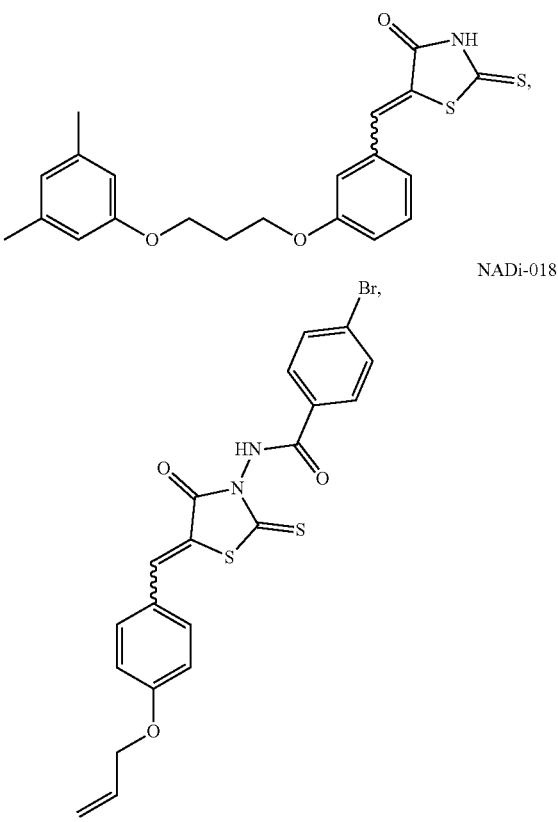
NADi-018
NADi-019
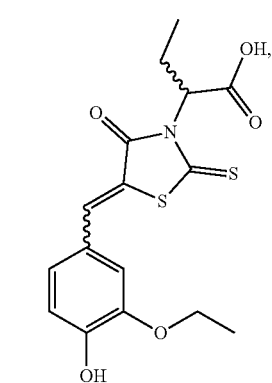
NADi-020
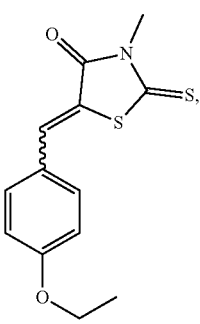

177
-continued
NADi-021
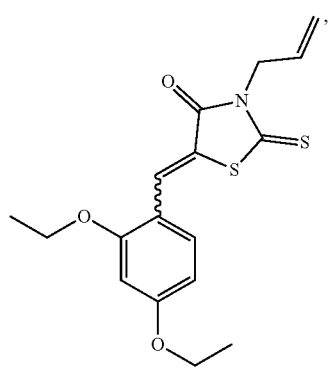
NADi-022
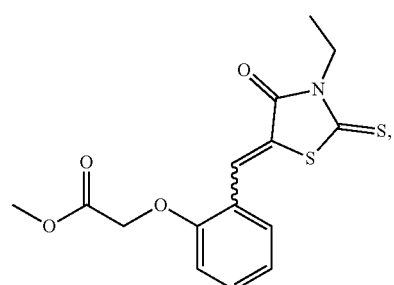
NADi-023
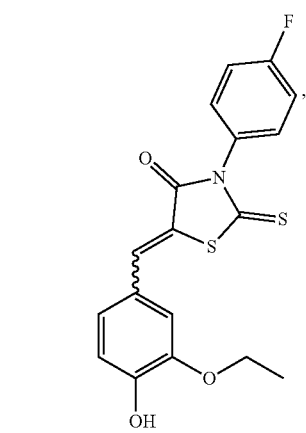
NADi-024
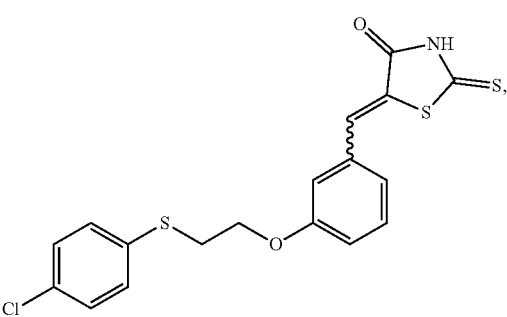
178
-continued
NADi-025
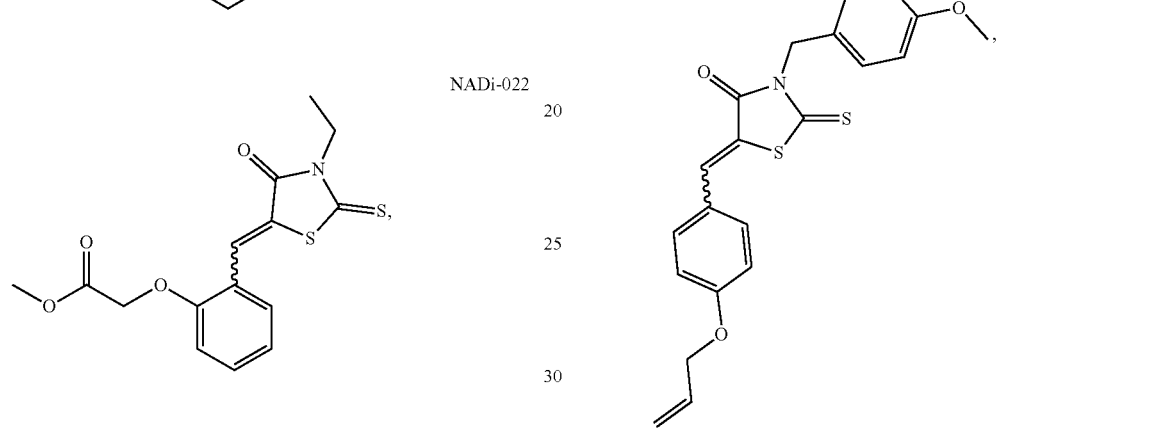
NADi-028
NADi-029
NADi-030
NADi-031

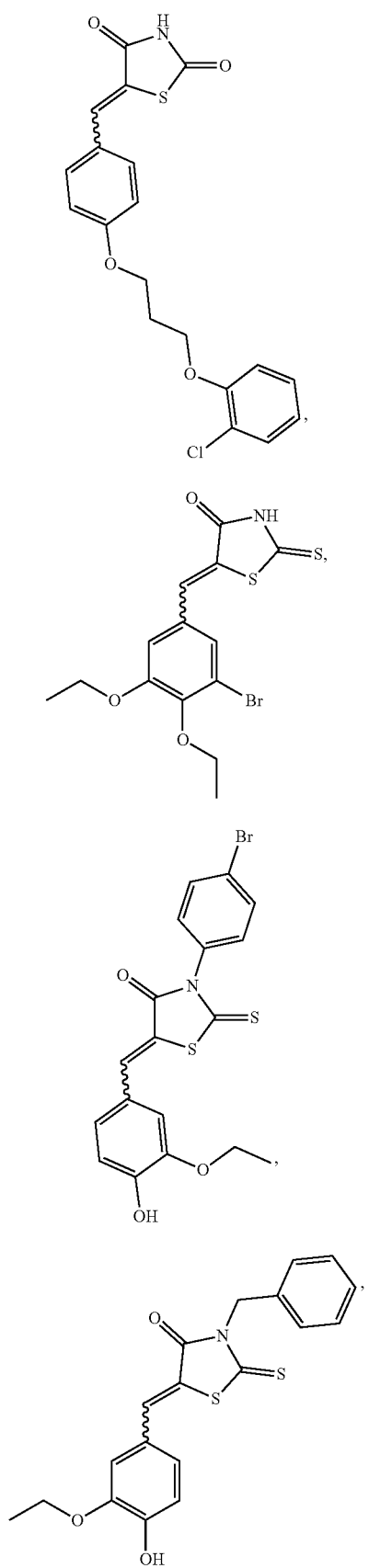
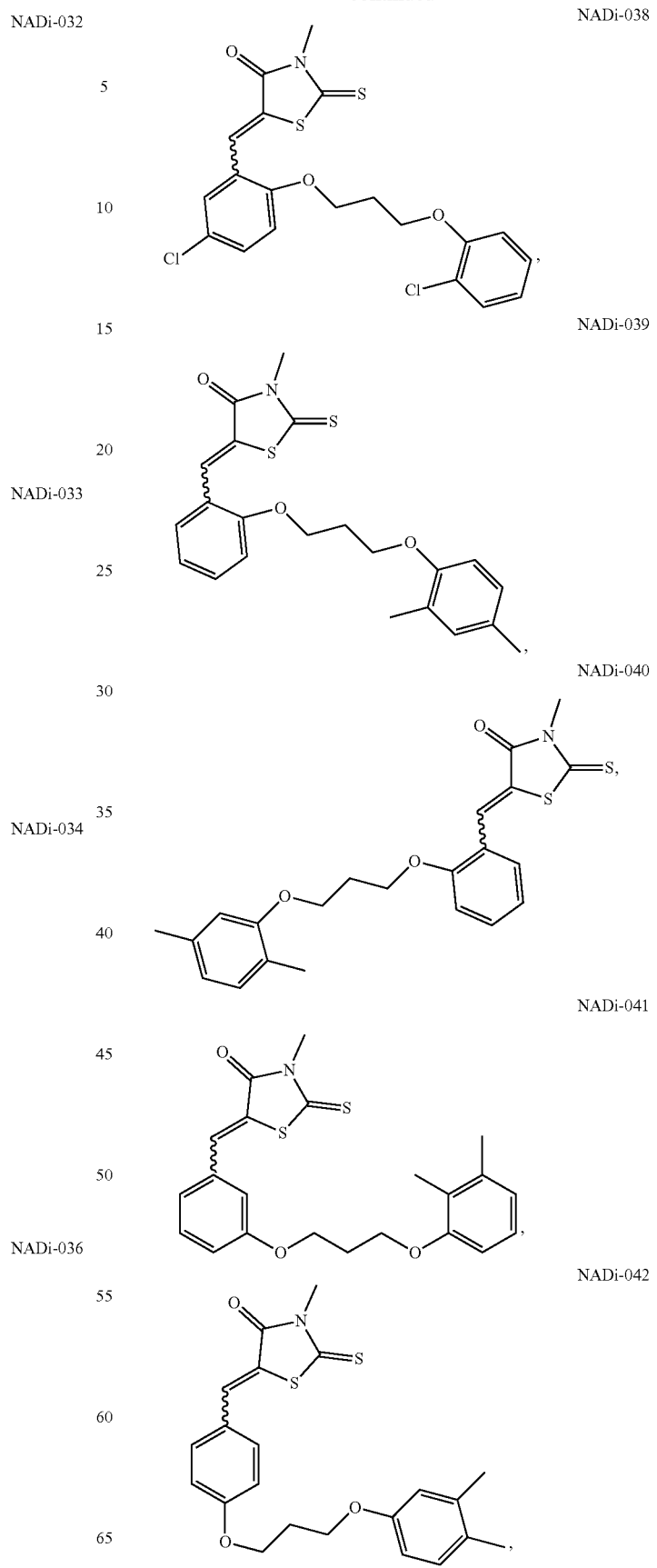

NADi-043
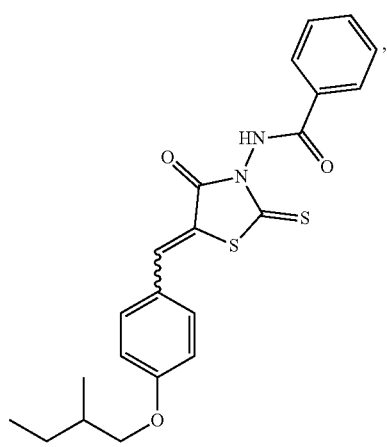
NADi-044
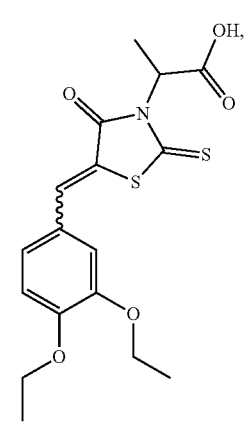
NADi-049
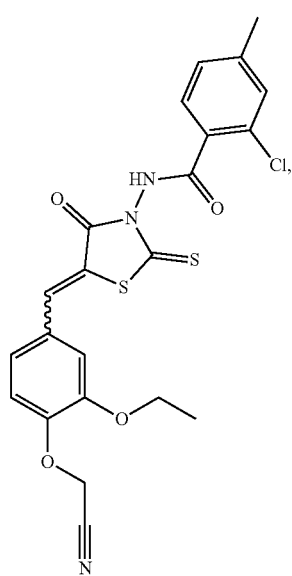
NADi-052
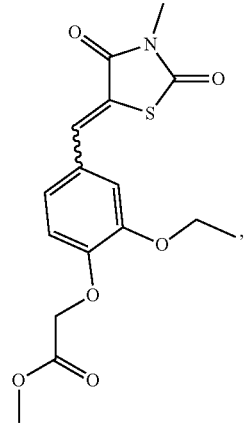
NADi-053
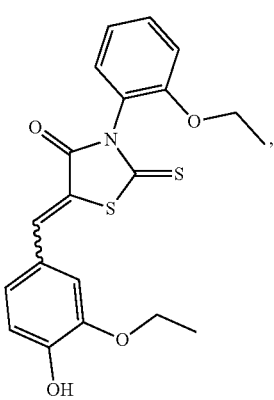
NADi-054
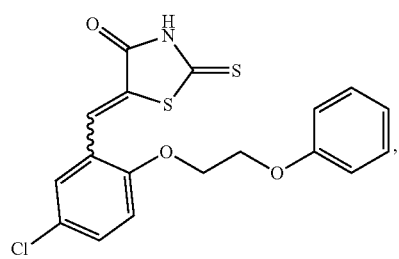
NADi-055
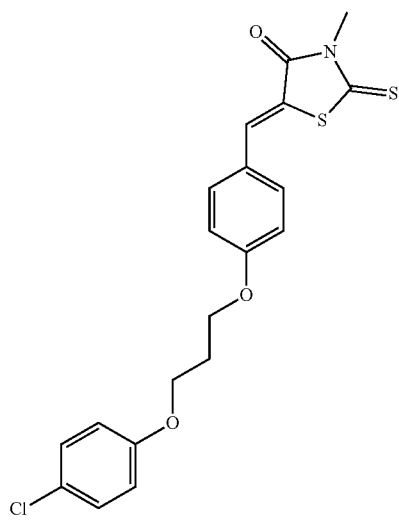

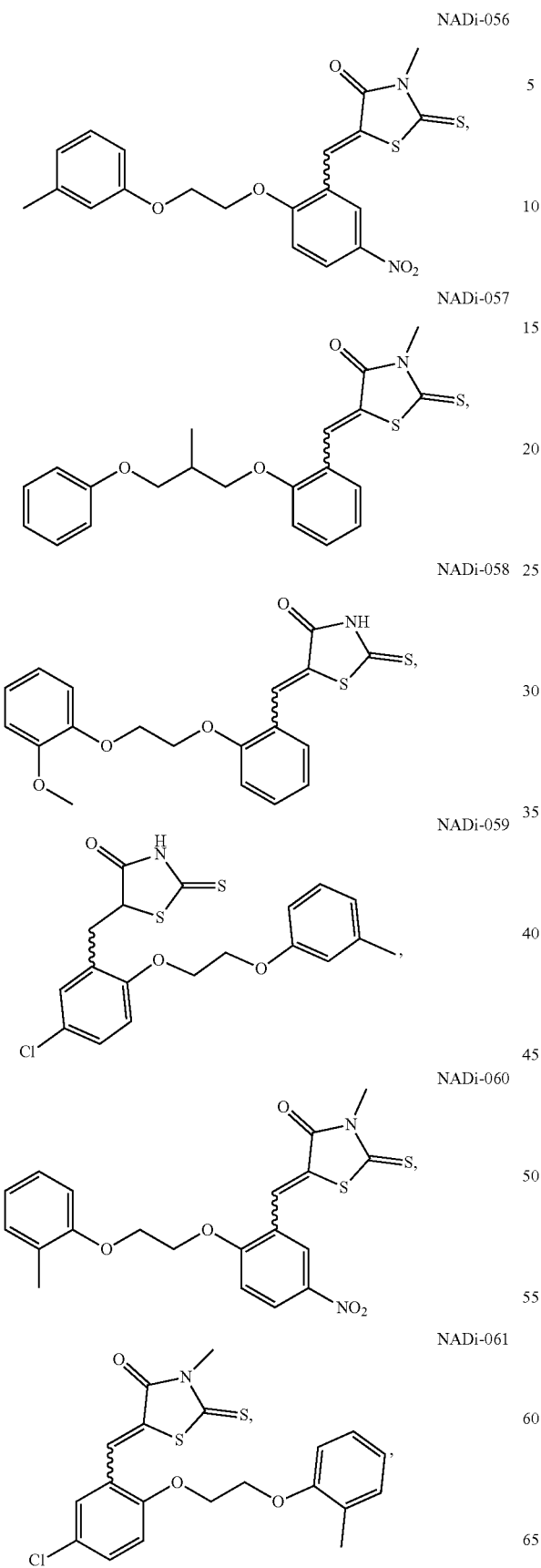
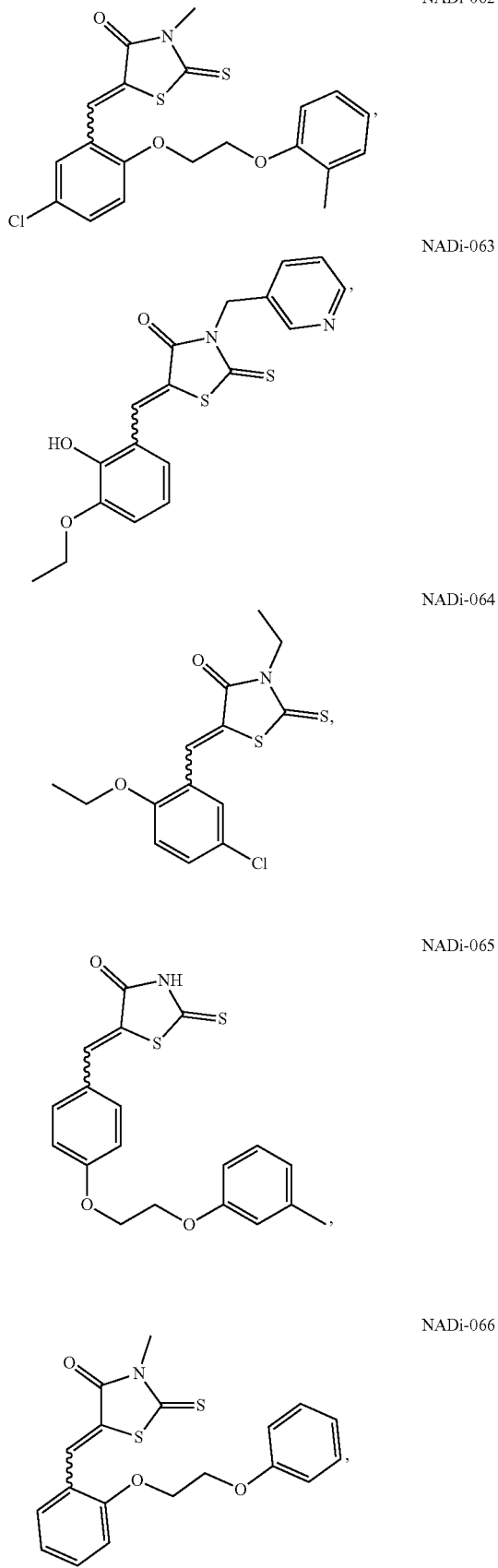

NADi-067
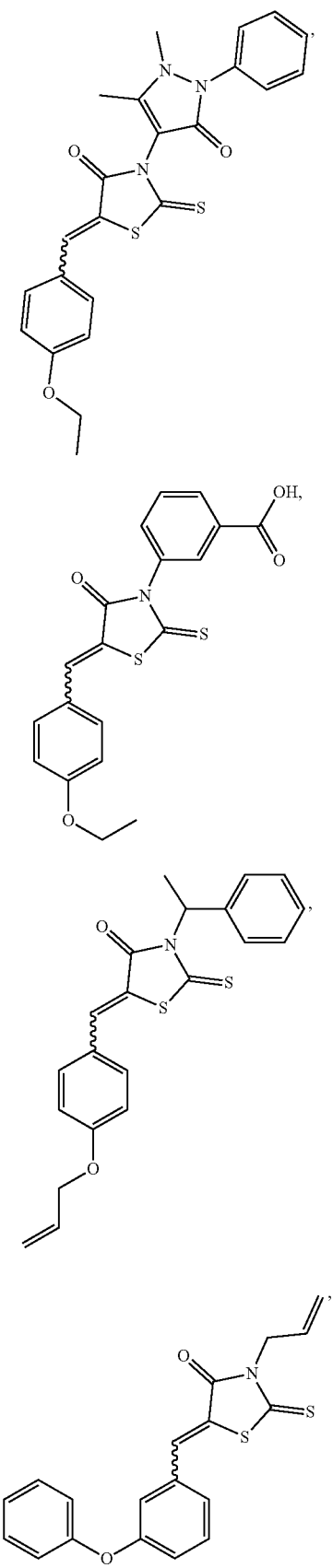
NADi-068
NADi-069
NADi-070
NADi-072
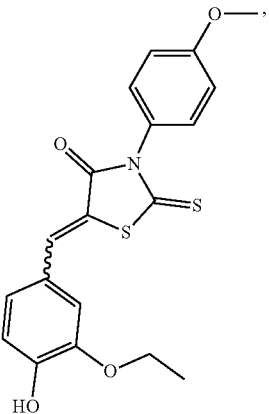
NADi-073
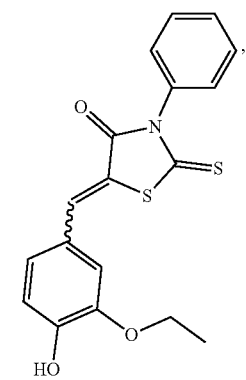
NADi-074
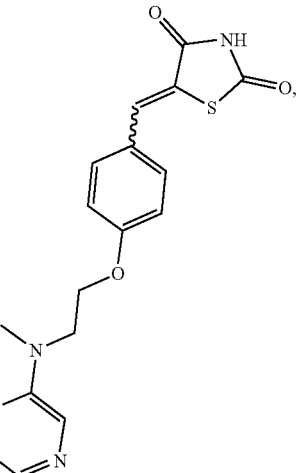
NADi-075
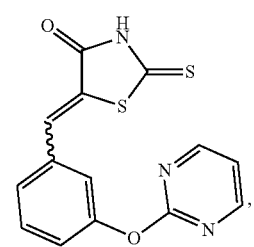

-continued
NADi-077
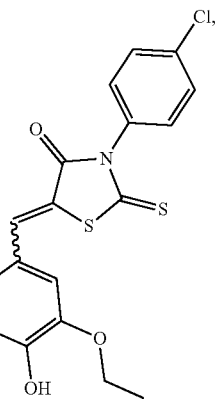
NADi-078
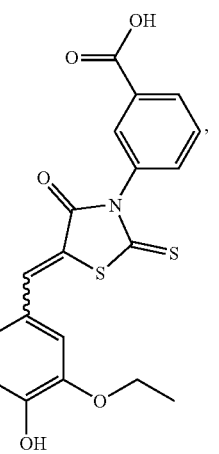
NADi-079
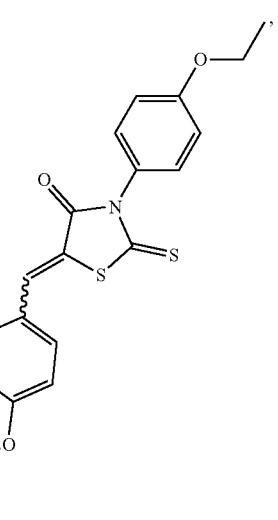
-continued
NADi-080
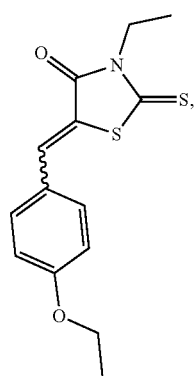
NADi-081
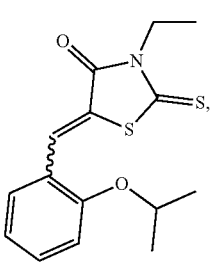
NADi-082
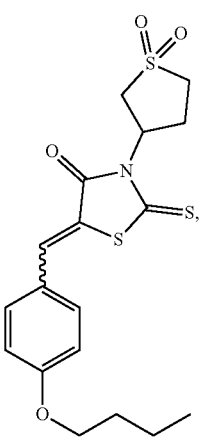
NADi-085
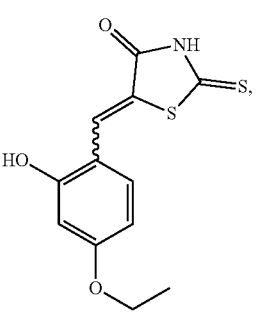
NADi-090
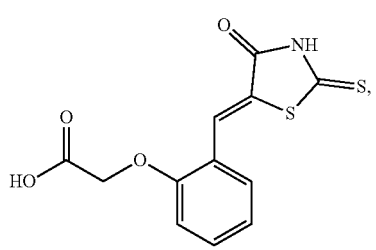

NADi-091
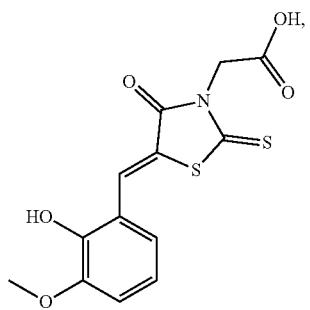
NADi-093
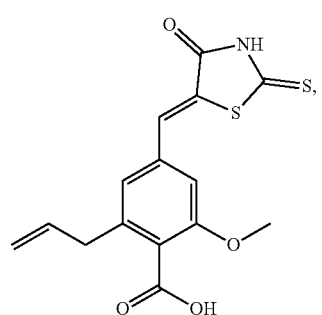
NADi-094
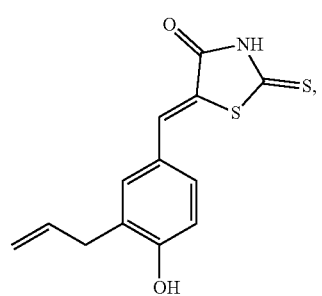
NADi-095
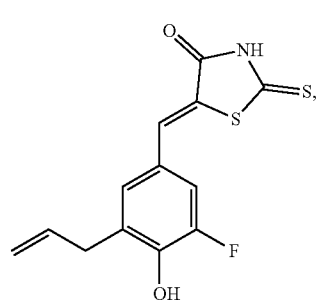
NADi-096
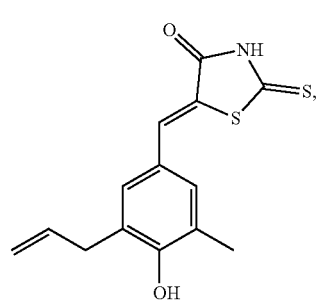
NADi-097
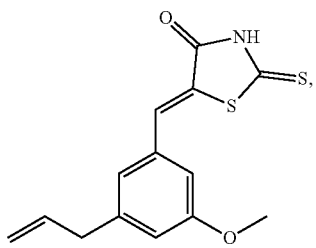
NADi-098
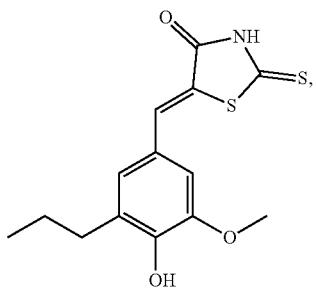
NADi-099
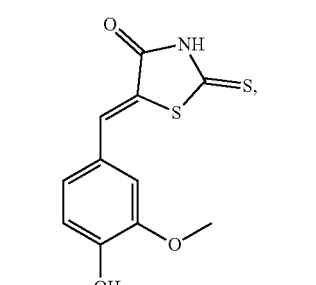
NADi-100
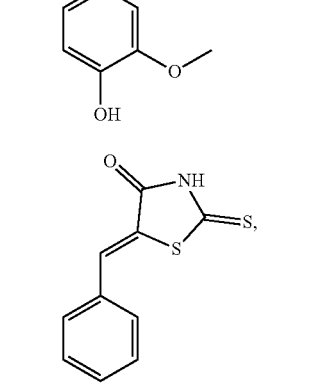
NADi-101
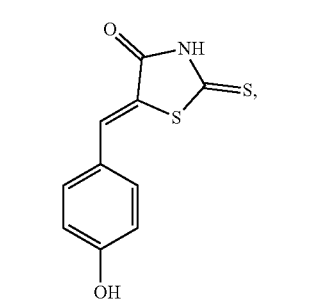
NADi-102
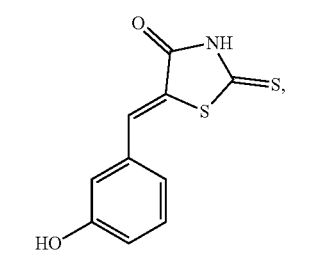

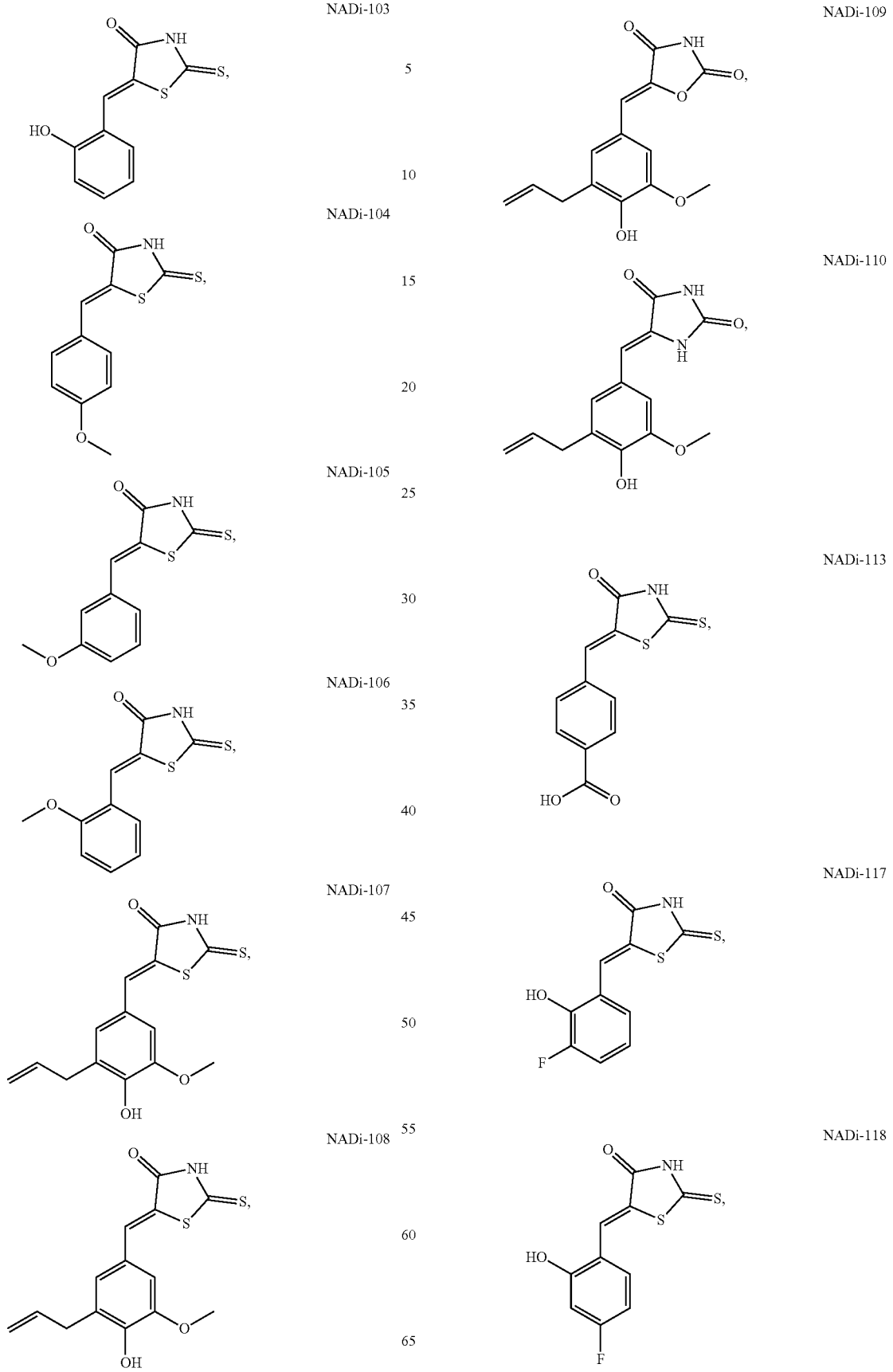

-continued
NADi-119
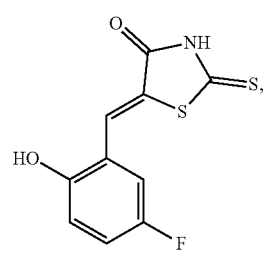
NADi-120
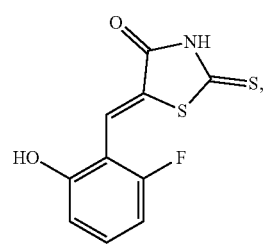
NADi-121
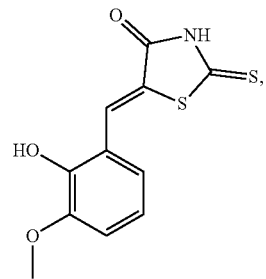
NADi-122
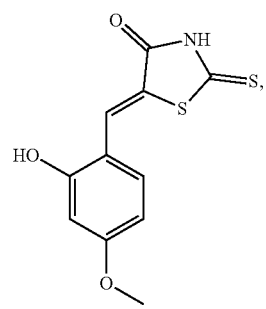
NADi-123
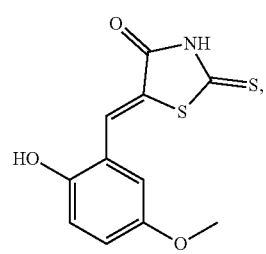
NADi-124
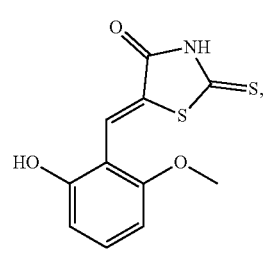
-continued
NADi-125
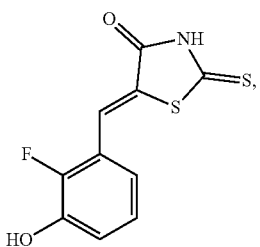
NADi-126
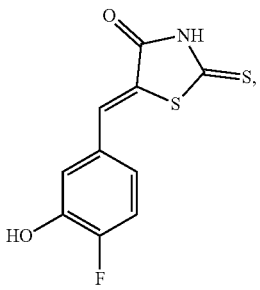
NADi-127
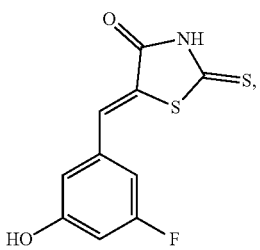
NADi-128
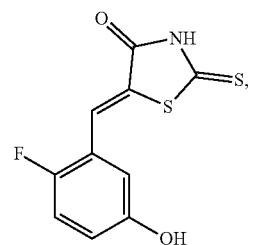
NADi-129
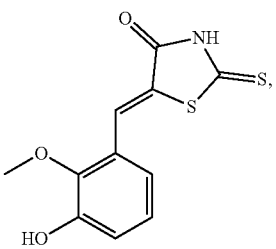
NADi-130
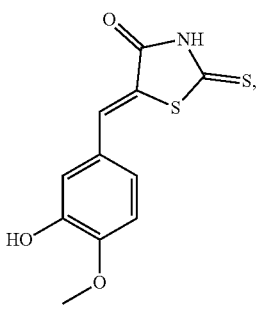

NADi-131
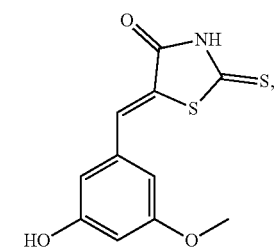
NADi-132
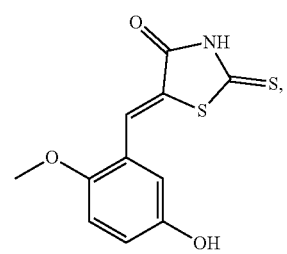
NADi-133
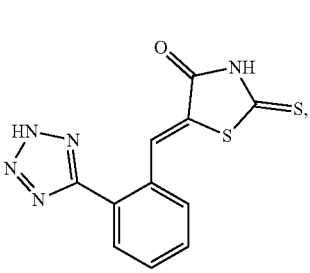
NADi-134
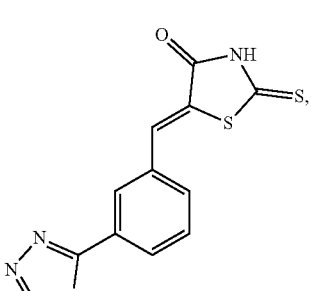
NADi-135
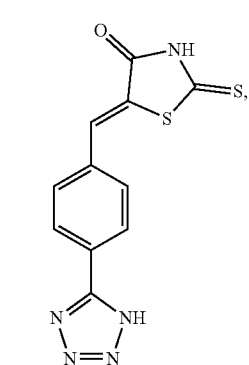
NADi-136
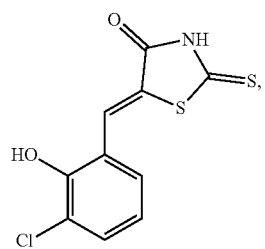
NADi-137
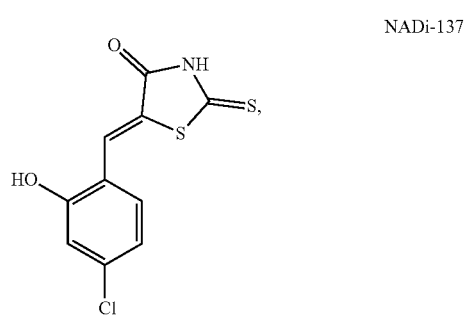
NADi-138
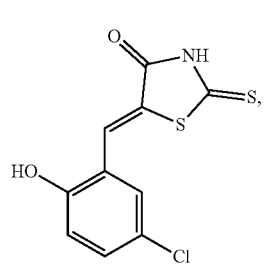
NADi-139
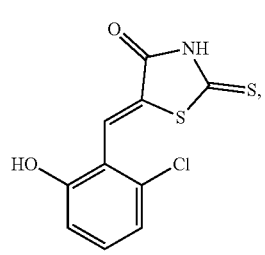
NADi-140
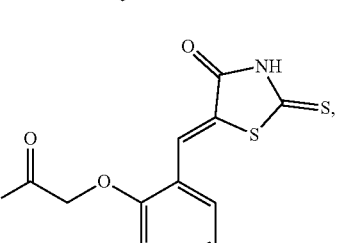
NADi-141
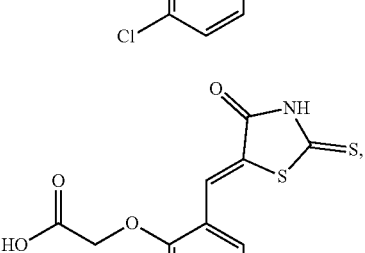

NADi-142
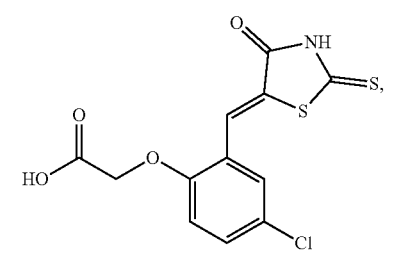
NADi-143
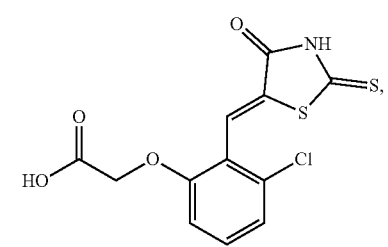
NADi-144
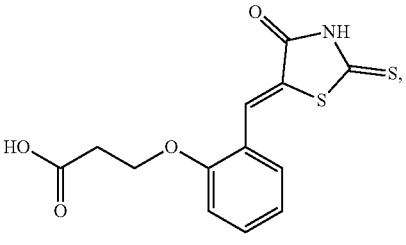
NADi-145
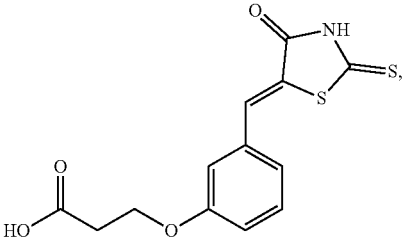
NADi-146
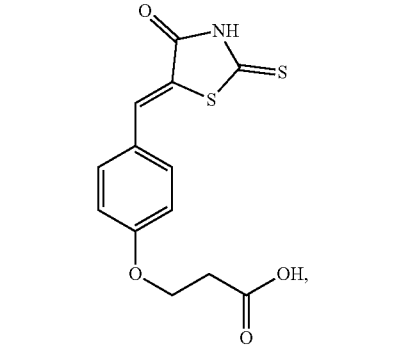
NADi-147
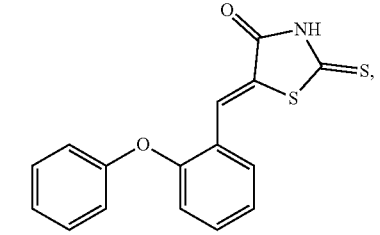
NADi-148
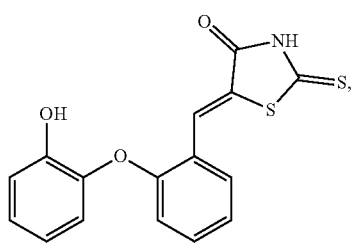
NADi-149
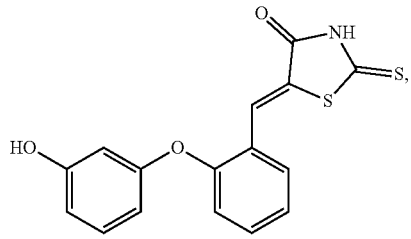
NADi-150
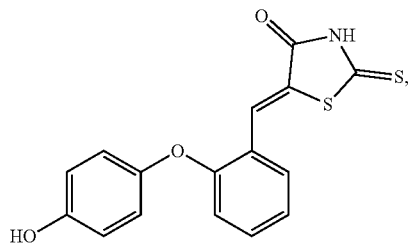
NADi-151
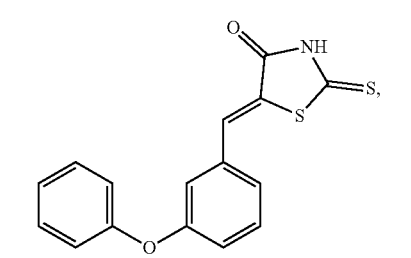
NADi-152
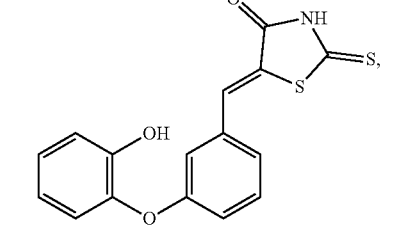
NADi-153
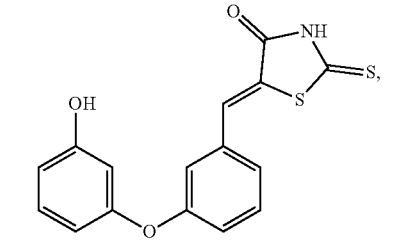

NADi-154
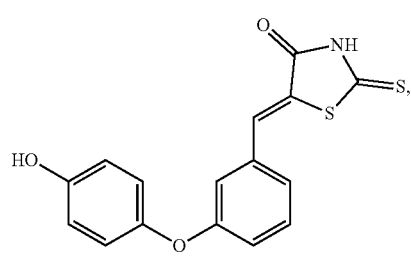
NADi-155
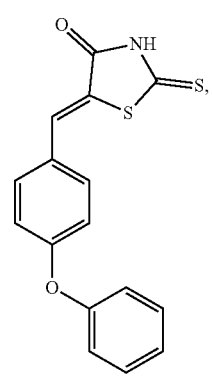
NADi-156
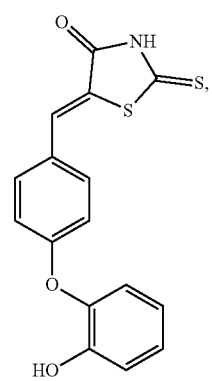
NADi-157
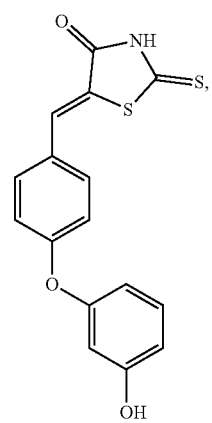
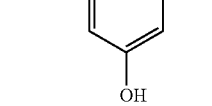
NADi-158
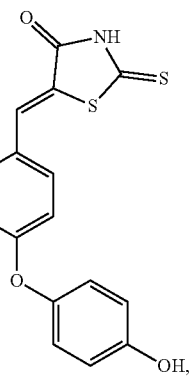
NADi-159
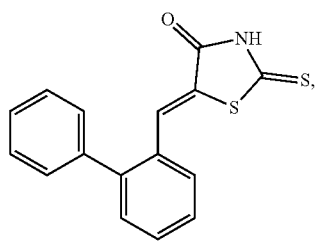
NADi-160
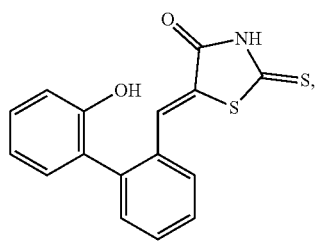
NADi-161
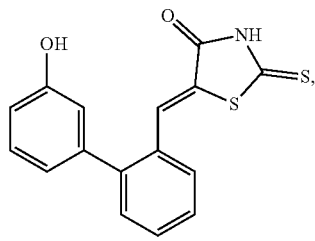
NADi-162
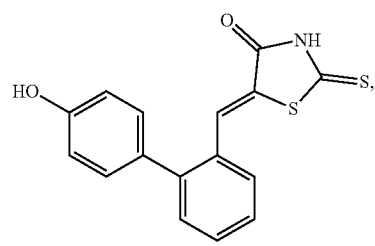

NADi-163
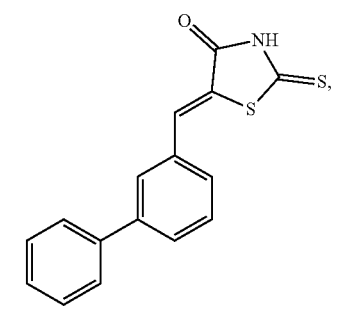
NADi-164
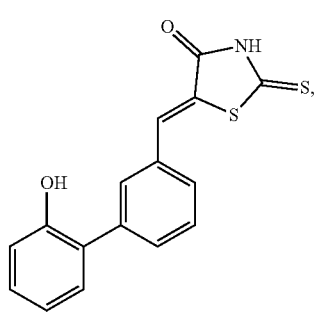
NADi-165
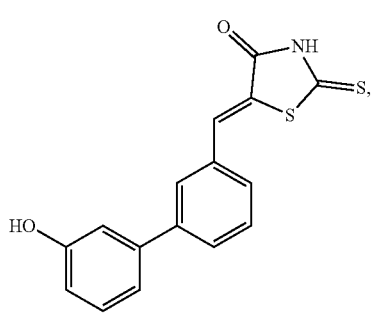
NADi-166
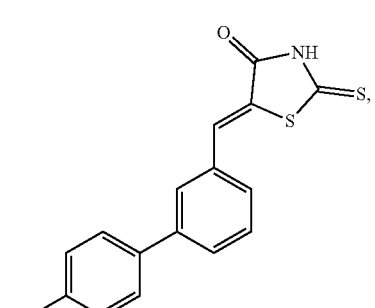
NADi-167
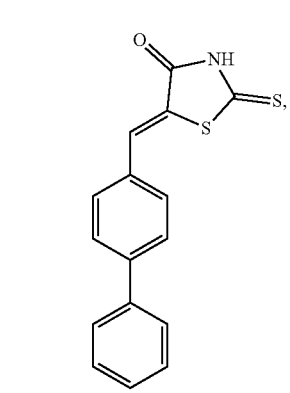
NADi-168
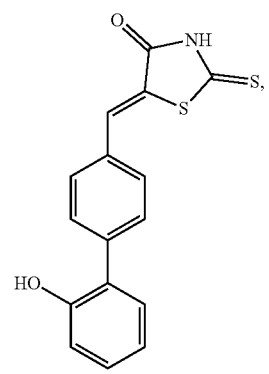
NADi-169
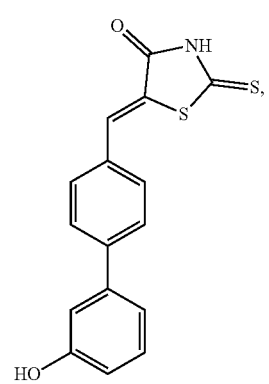
NADi-170
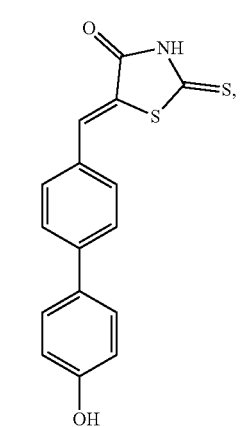
NADi-176
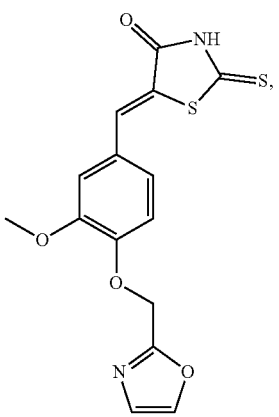

NADi-177
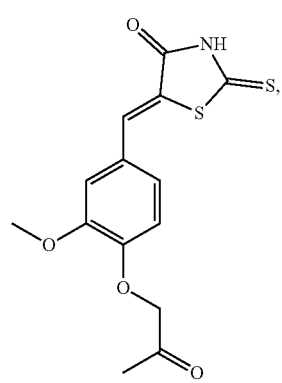
NADi-181
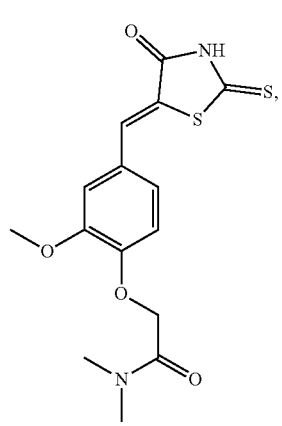
NADi-178
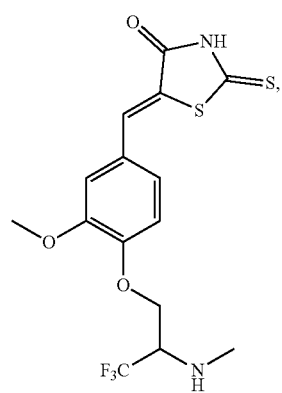
NADi-182
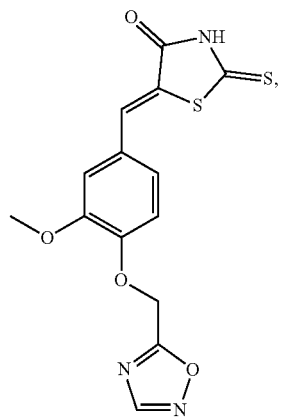
NADi-179
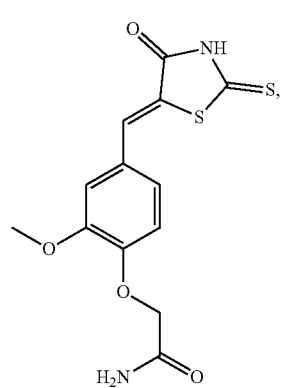
NADi-183
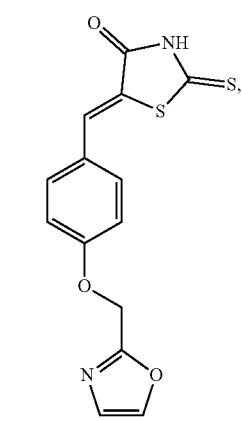
NADi-180
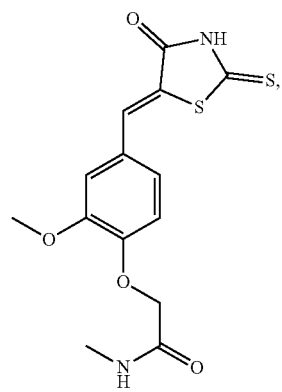
NADi-184
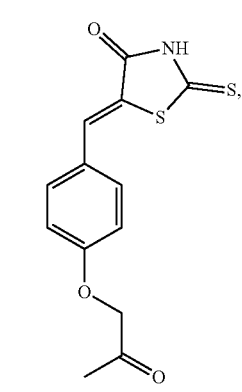

NADi-185
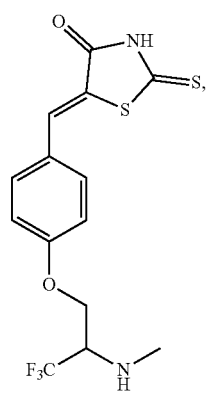
NADi-186
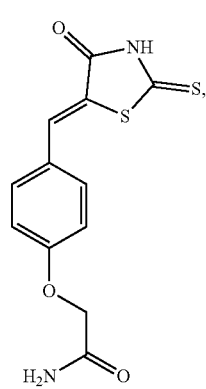
NADi-187
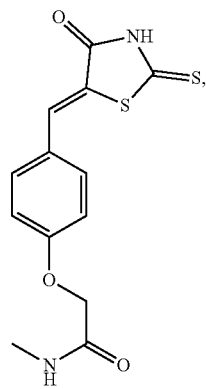
NADi-188
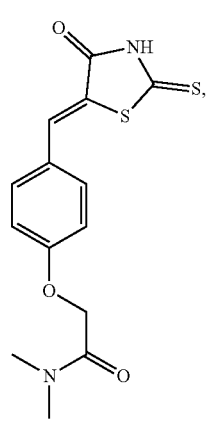
NADi-189
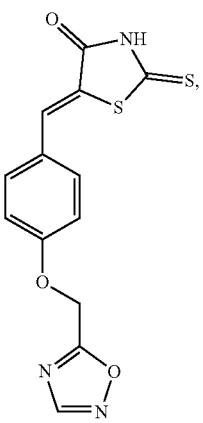
NADi-190
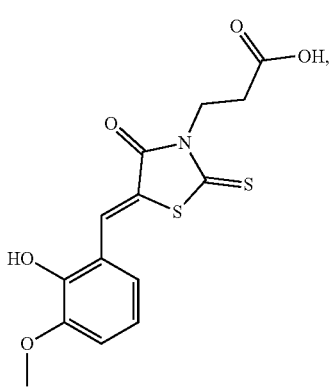
NADi-191
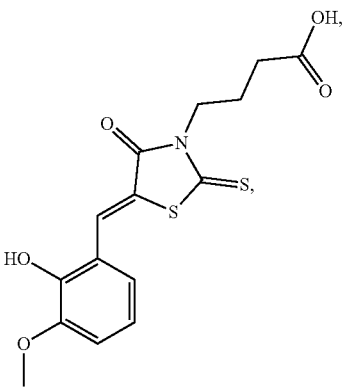
NADi-192
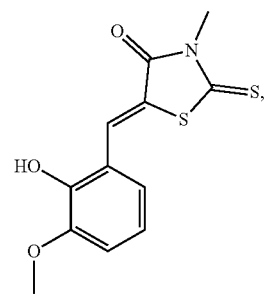

NADi-193
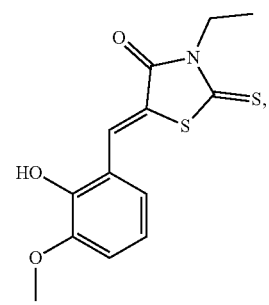
NADi-194
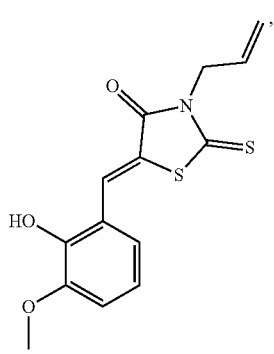
NADi-195
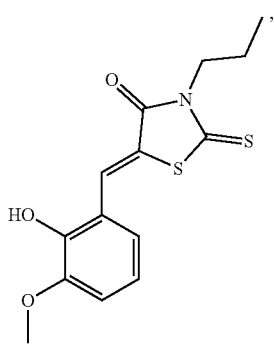
NADi-196
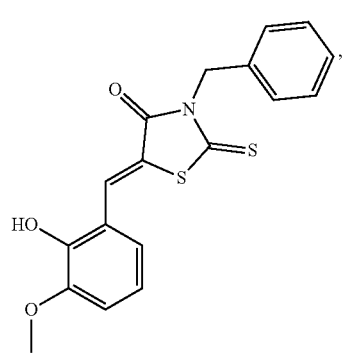
NADi-197
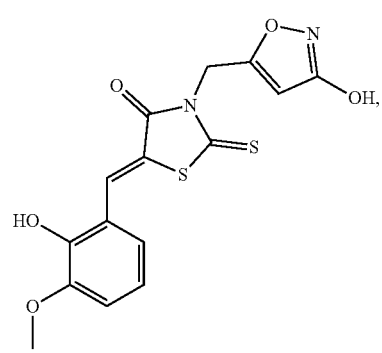
NADi-198
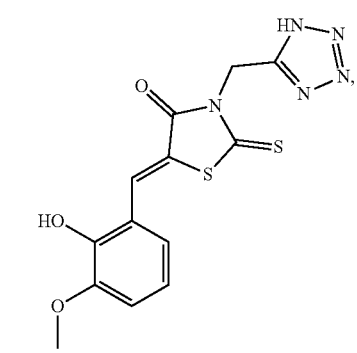
NADi-199
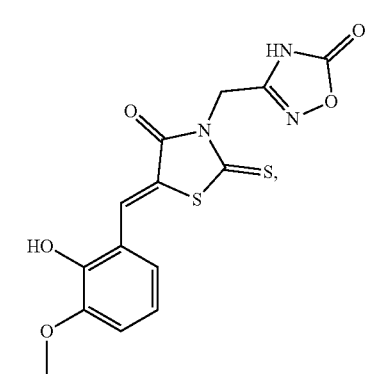
NADi-200
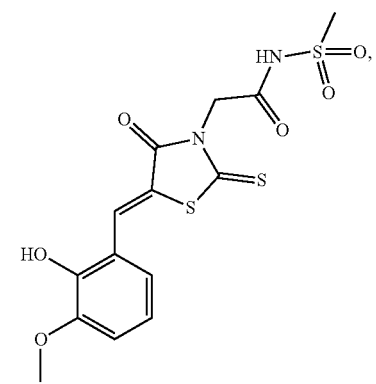

-continued
NADi-201
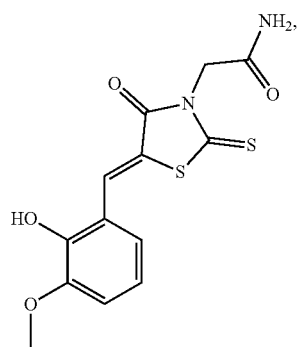
NADi-202
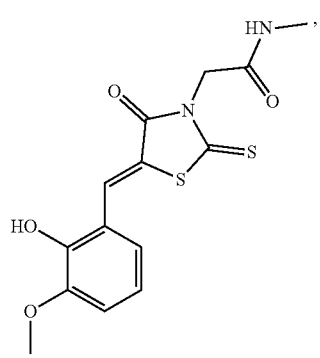
NADi-203
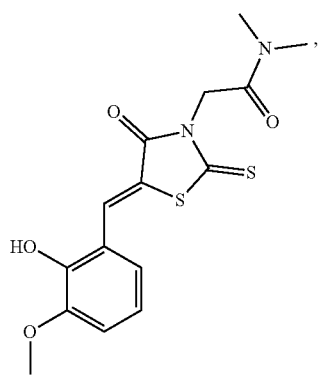
NADi-204
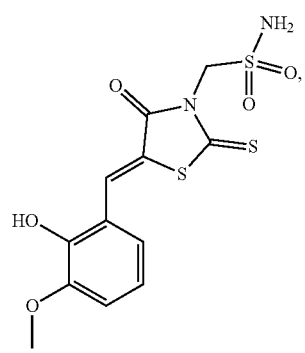
-continued
NADi-205
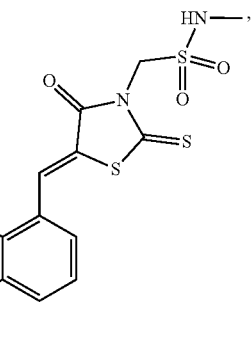
NADi-206
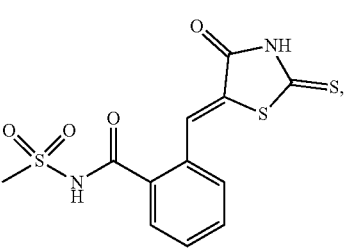
NADi-207
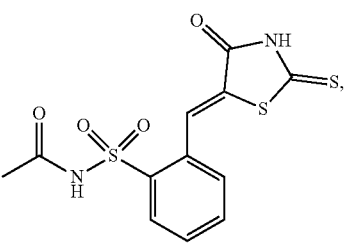
NADi-208
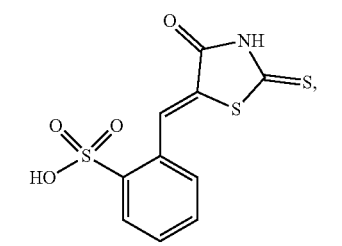
NADi-209
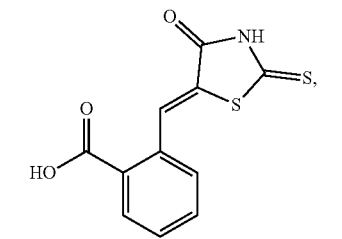
NADi-210
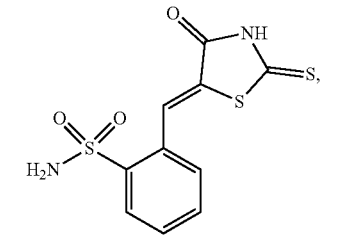

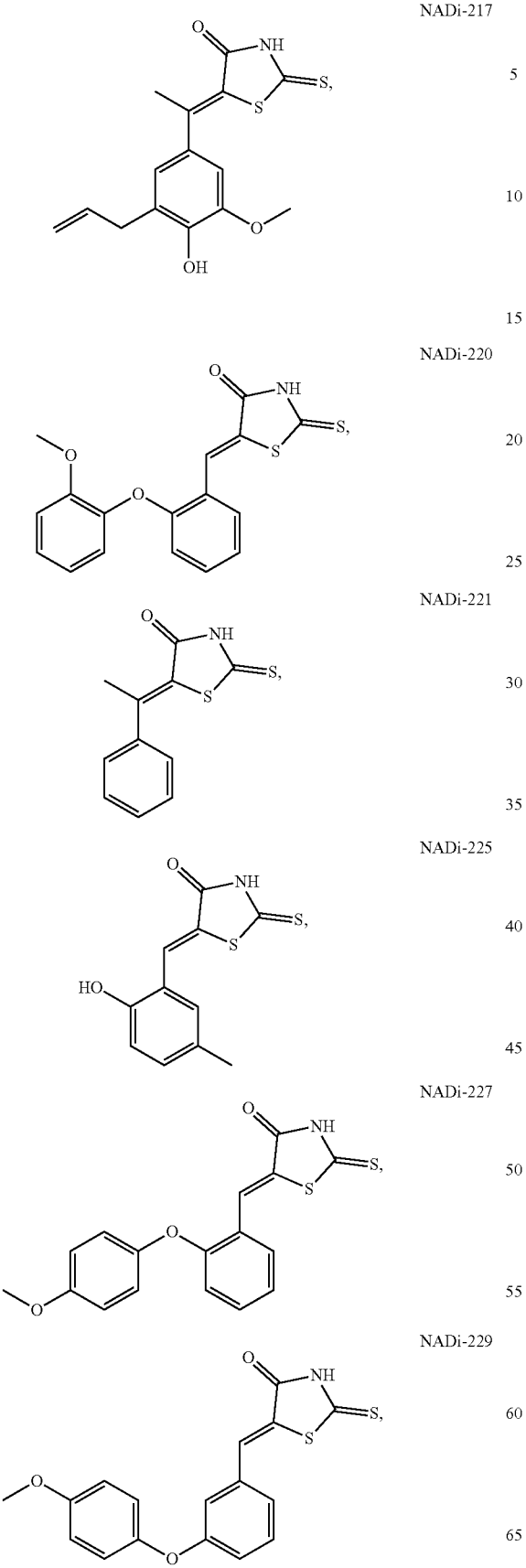
NADi-217
NADi-220
NADi-221
NADi-225
NADi-227
NADi-229
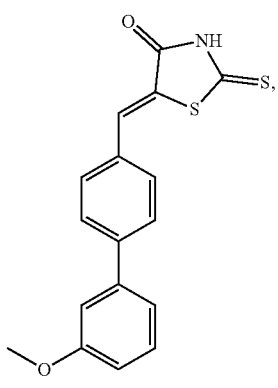
NADi-230
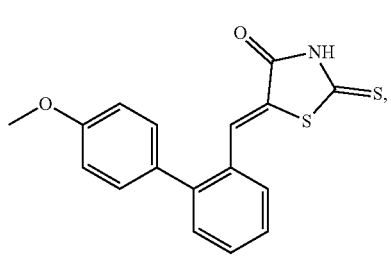
NADi-231
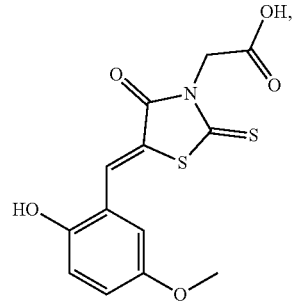
NADi-232
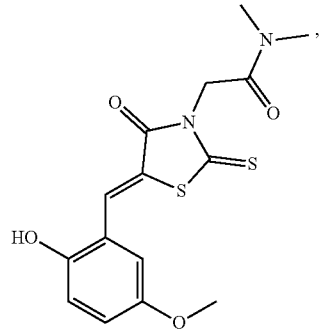
NADi-235
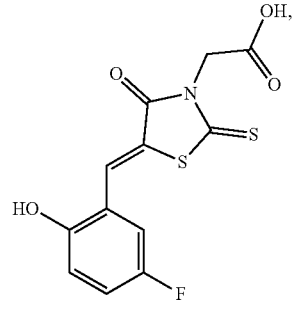
NADi-236

NADi-237
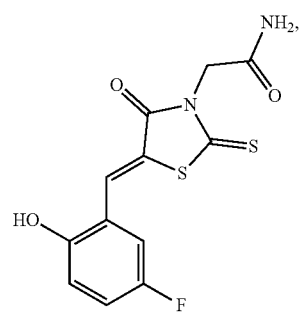
NADi-238
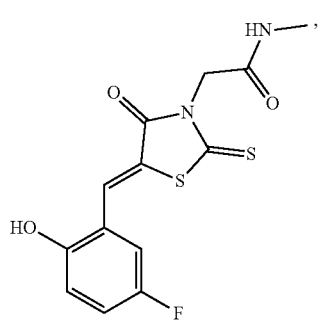
NADi-239
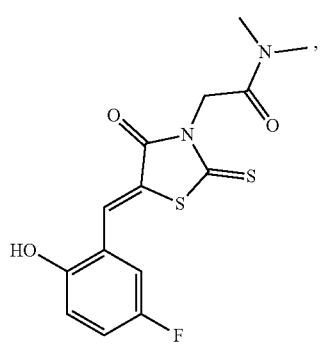
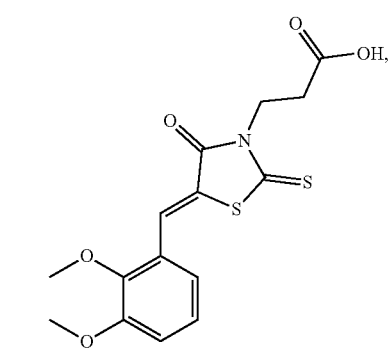
NADi-111
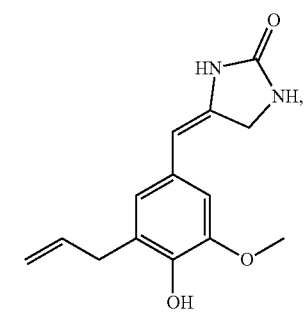
NADi-112
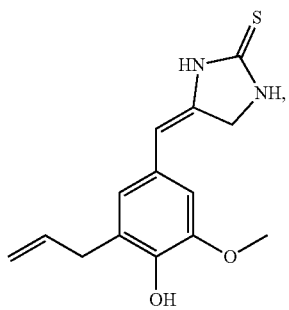
NADi-114
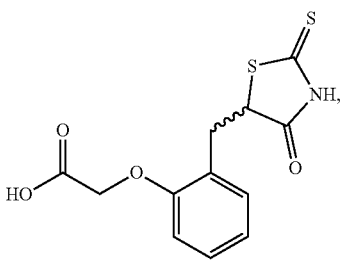
NADi-115
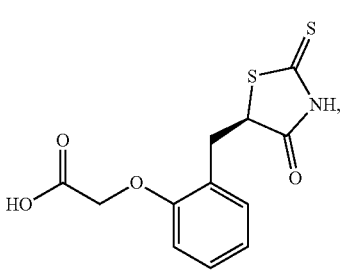
NADi-116
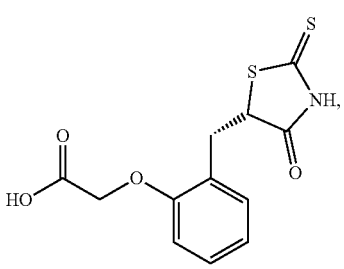
NADi-171
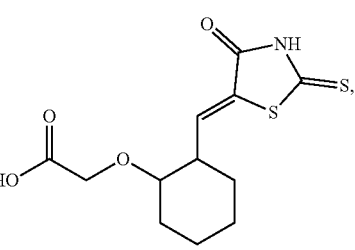
NADi-172
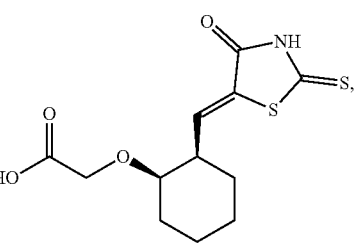

NADi-173
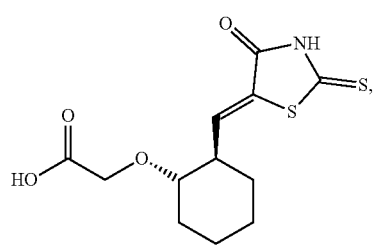
NADi-174
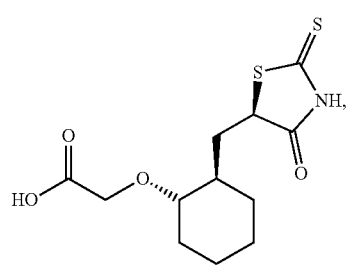
NADi-175
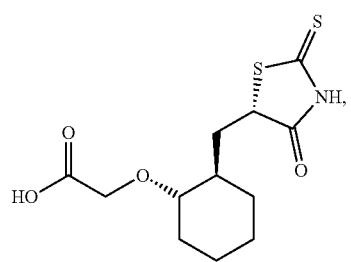
NADi-211
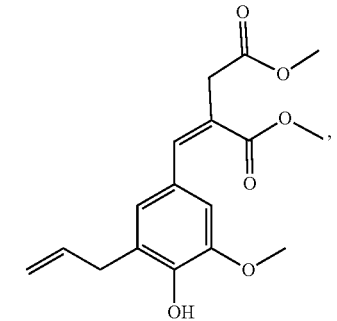
NADi-212
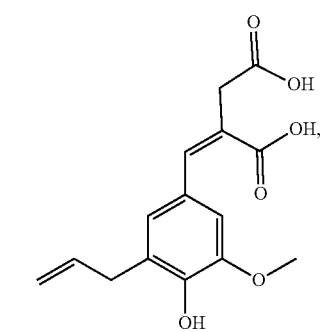
NADi-213
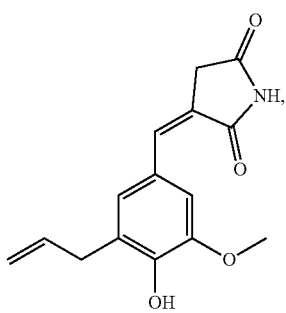
NADi-214
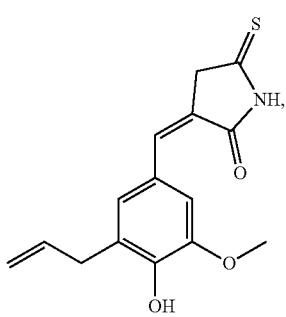
NADi-215
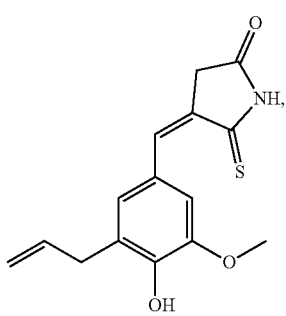
NADi-216
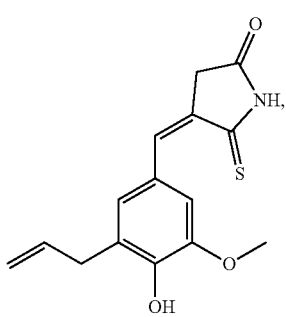
NADi-218
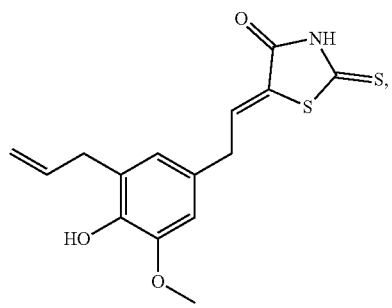

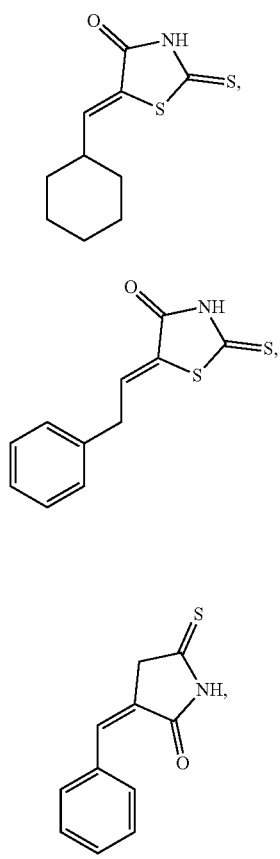
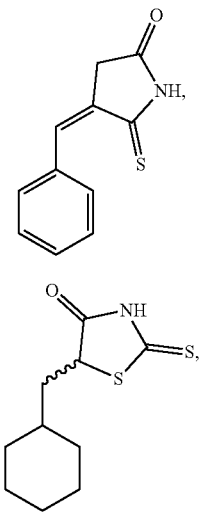
or a mixture thereof, in an amount effective to inhibit the NTC.
* * * * *

UNITED STATES PATENT AND TRADEMARK OFFICE
CERTIFICATE OF CORRECTION

PATENT NO. : 10,501,413 B2
APPLICATION NO. : 15/560743
DATED : December 10, 2019
INVENTOR(S) : Anthony J. Capobianco et al.

Page 1 of 1

It is certified that error appears in the above-identified patent and that said Letters Patent is hereby corrected as shown below:

In the Specification

Column 1, Lines 19-23:
"This invention was made with government support under grant numbers NCI R01CA083736-12A1 and NCI R01CA125044-02, each awarded by the National Institutes of Health. The Government has certain rights in the invention."

Should be:
--This invention was made with government support under grant number CA083736 awarded by the National Institutes of Health. The government has certain rights in the invention.--

Signed and Sealed this
Thirty-first Day of March, 2020

Andrei Iancu
*Director of the United States Patent and Trademark Office*